US011446327B2

(12) United States Patent
Riziq et al.

(10) Patent No.: US 11,446,327 B2
(45) Date of Patent: Sep. 20, 2022

(54) ENCAPSULATED AMORPHOUS CALCIUM CARBONATE COMPOSITIONS

(71) Applicant: AMORPHICAL LTD., Ness Ziona (IL)

(72) Inventors: Ali Abo Riziq, Jatt Village (IL); Sharon Hershkovitz, Lapid (IL); Yosef Ben, Meshek Ben Arava (IL); Yigal Blum, San Jose, CA (US)

(73) Assignee: AMORPHICAL LTD., Ness Ziona (IL)

( * ) Notice: Subject to any disclaimer, the term of this patent is extended or adjusted under 35 U.S.C. 154(b) by 720 days.

(21) Appl. No.: 15/329,664

(22) PCT Filed: Jul. 30, 2015

(86) PCT No.: PCT/IL2015/050784
§ 371 (c)(1),
(2) Date: Jan. 27, 2017

(87) PCT Pub. No.: WO2016/016893
PCT Pub. Date: Feb. 4, 2016

(65) Prior Publication Data
US 2017/0208827 A1 Jul. 27, 2017

Related U.S. Application Data

(60) Provisional application No. 62/031,170, filed on Jul. 31, 2014.

(51) Int. Cl.
| | |
|---|---|
| *A61K 33/10* | (2006.01) |
| *C01F 11/18* | (2006.01) |
| *A23C 9/13* | (2006.01) |
| *A23C 9/152* | (2006.01) |
| *A23C 19/09* | (2006.01) |
| *A23C 19/068* | (2006.01) |
| *A23C 19/076* | (2006.01) |
| *A23L 33/16* | (2016.01) |
| *A61K 9/00* | (2006.01) |
| *A61K 9/10* | (2006.01) |
| *A61K 47/10* | (2017.01) |
| *A61K 47/14* | (2017.01) |
| *A61K 47/26* | (2006.01) |
| *A61K 47/34* | (2017.01) |
| *A61K 47/40* | (2006.01) |
| *A23C 13/12* | (2006.01) |
| *A23C 11/00* | (2006.01) |

(52) U.S. Cl.
CPC ............ *A61K 33/10* (2013.01); *A23C 9/1322* (2013.01); *A23C 9/1522* (2013.01); *A23C 19/0921* (2013.01); *A23L 33/16* (2016.08); *A61K 9/0014* (2013.01); *A61K 9/10* (2013.01); *A61K 47/10* (2013.01); *A61K 47/14* (2013.01); *A61K 47/26* (2013.01); *A61K 47/34* (2013.01); *A61K 47/40* (2013.01); *C01F 11/18* (2013.01); *C01F 11/185* (2013.01); *A23C 11/00* (2013.01); *A23C 13/12* (2013.01); *A23C 19/0684* (2013.01); *A23C 19/0765* (2013.01); *A23V 2002/00* (2013.01); *A23V 2250/032* (2013.01); *A23V 2250/1578* (2013.01); *A23V 2250/1886* (2013.01); *A23V 2250/192* (2013.01); *A23V 2250/5482* (2013.01); *C01P 2002/02* (2013.01); *C01P 2002/72* (2013.01)

(58) Field of Classification Search
CPC ........ A61K 33/10; A61K 47/10; A61K 47/14; A23L 33/16; A23L 27/72; A23C 9/1322; A23C 9/1522; A23C 19/0921; C01F 11/18; C01F 11/185
USPC .................................................. 423/430, 460
See application file for complete search history.

(56) References Cited

U.S. PATENT DOCUMENTS

| | | | |
|---|---|---|---|
| 4,237,147 A | 12/1980 | Merten | |
| 6,468,568 B1* | 10/2002 | Leusner | ................. A23P 10/35 426/103 |
| 2005/0255202 A1* | 11/2005 | Dalziel | .................... B01J 13/04 426/302 |
| 2008/0199540 A1* | 8/2008 | Sagi | ....................... A61K 33/10 424/687 |
| 2010/0221362 A1 | 9/2010 | Bentov | |
| 2010/0310677 A1 | 12/2010 | Bentov | |

FOREIGN PATENT DOCUMENTS

| | | |
|---|---|---|
| CA | 2806131 | 2/2012 |
| CN | 101254448 A | 9/2008 |
| CN | 101580260 | 11/2009 |
| CN | 101969962 | 2/2011 |
| JP | 2008-500332 A | 1/2008 |
| JP | 2009-518322 A | 5/2009 |
| JP | 2011-036239 A | 2/2011 |
| JP | 2012-521757 A | 9/2012 |
| JP | 2013-503611 A | 2/2013 |
| KR | 1020050110119 | 11/2005 |

(Continued)

OTHER PUBLICATIONS

Bentov et al., (2010) Stabilization of amorphous calcium carbonate by phosphate rich organic matrix proteins and by single phosphoamino acids. J Struct Biol 171(2): 207-15.

(Continued)

*Primary Examiner* — Jeffrey P Mornhinweg
(74) *Attorney, Agent, or Firm* — Dorsey & Whitney LLP

(57) ABSTRACT

The present invention provides stable amorphous calcium carbonate (ACC) compositions, and food articles comprising said compositions.

18 Claims, 16 Drawing Sheets

(56) References Cited

FOREIGN PATENT DOCUMENTS

| RU | 2305948 C2 | 9/2007 |
|---|---|---|
| WO | 2004078694 | 9/2004 |
| WO | 2005115414 | 12/2005 |
| WO | 2007065441 | 6/2007 |
| WO | 2008041236 | 4/2008 |
| WO | 2009053967 | 4/2009 |
| WO | 2012149173 | 11/2012 |
| WO | 2013088440 | 6/2013 |
| WO | 2014024191 | 2/2014 |

OTHER PUBLICATIONS

Champagne & Fustier, (2007) Microencapsulation for the improved delivery of bioactive compounds into foods. Current opinion in biotechnology, 18(2), 184-190.

Clarkson et al., (1992) Role of metastable phases in the spontaneous precipitation of calcium carbonate. J Chem Soc, Faraday Trans 88(2): 243-249.

Guéguen & Pointillart, (2000) The bioavailability of dietary calcium. Journal of the American College of Nutrition, 19 (sup2), 119S-136S.

Hecker et al., (2003) Phosphorylation of serine residues is fundamental for the calcium-binding ability of Orchestin, a soluble matrix protein from crustacean calcium storage structures. FEBS Lett 535(1-3): 49-54.

Hu et al., (2010) Strongly bound citrate stabilizes the apatite nanocrystals in bone. Proc Natl Acad Sci USA 107(52): 22425-22429.

Huang et al., (2007) A carbonate controlled-addition method for amorphous calcium carbonate spheres stabilized by poly(acrylic acid)s. Langmuir 23: 12086-12095.

Johnsson et al., (1991) Adsorption and mineralization effects of citrate and phosphocitrate on hydroxyapatite. Calcif Tissue Int 49(2): 134-137.

Koga et al., (1998) Crystallization of amorphous calcium carbonate. Thermochimica Acta 318(1-2): 239-244.

Lee et al., (2005) Fabrication of unusually stable amorphous calcium carbonate in an ethanol medium. Materials Chemistry and Physics 93(2-3): 376-382.

Loste et al., (2003) The role of magnesium in stabilising amorphous calcium carbonate and controlling calcite morphologies. Journal of Crystal Growth 254(1-2): 206-218.

Malkaj and Dalas (2007) The effect of acetaminophen on the crystal growth of calcium carbonate. J Mater Sci Mater Med 18(5): 871-875.

Manoli and Dalas (2002) The effect of sodium alginate on the crystal growth of calcium carbonate. J Mater Sci Mater Med 13(2): 155-158.

Martins et al., (2008) Hydroxyapatite micro- and nanoparticles: nucleation and growth mechanisms in the presence of citrate species. J Colloid Interface Sci 318(2): 210-216.

Maruyama et al., (2011) Synthesizing a composite material of amorphous calcium carbonate and aspartic acid. Materials Letters 65(2): 179-181.

Meiron et al., (2011) Solubility and bioavailability of stabilized amorphous calcium carbonate. Journal of Bone and Mineral Research, 26(2), 364-372.

Multigner et al., (1983) Pancreatic stone protein, a phosphoprotein which inhibits calcium carbonate precipitation from human pancreatic juice. Biochemical And Biophysical Research Communications 110(1): 69-74.

Reddi et al., (1980) Influence of phosphocitrate, a potent inhibitor of hydroxyapatite crystal growth, on mineralization of cartilage and bone. Biochem Biophys Res Commun 97(1): 154-159.

Rodriguez-Blanco et al., (2008) How to make 'stable' ACC: protocol and preliminary structural characterization. Mineralogical Magazine 72(1): 283-286.

Rodriguez-Blanco et al., (2012) The role of pH and Mg on the stability and crystallization of amorphous calcium carbonate. Journal of Alloys and Compounds 536(Supp 1): S477-S479 International Symposium on Metastable, Amorphous and Nanostructured Materials, ISMANAM-2011 (Jun. 26 to Jul. 1, 2011).

Saitoh et al., (1985) Inhibition of calcium-carbonate precipitation by human salivary proline-rich phosphoproteins. Arch Oral Biol 30(8): 641-643.

Sawada (1997) The mechanisms of crystallization and transformation of calcium carbonates. Pure & Appl Chem 69(5): 921-928.

Schneiders et al., (2007) Effect of modification of hydroxyapatite/collagen composites with sodium citrate, phosphoserine, phosphoserine/RGD-peptide and calcium carbonate on bone remodelling. Bone 40(4): 1048-1059.

Shechter et al., (2008) A gastrolith protein serving a dual role in the formation of an amorphous mineral containing extracellular matrix. Proc Natl Acad Sci U S A 105(20): 7129-7134.

Thomas and Birchall (1983) The retarding action of sugars on cement hydration. Cement and Concrete Research 13(6): 830-842.

Vaisanen H "CaCO3 scale inhibition in paper making processes—evaluation of testing methods and inhibitor performance". Master's thesis; Tampere University of Technology, Dec. 2011. 103 pages.

Wang & Xu, (2013) Amorphous calcium carbonate stabilized by a flexible biomimetic polymer inspired by marine mussels. Crystal Growth & Design, 13(5), 1937-1942.

Xurong et al., (2008) Amorphous Calcium Carbonate in Biomineralization. Progress in Chemistry 20(1): 54-59.

\* cited by examiner

ENCAPSULATED AMORPHOUS CALCIUM CARBONATE COMPOSITIONS

FIELD OF THE INVENTION

The present invention relates to edible compositions comprising amorphous calcium carbonate, and to food products comprising these compositions.

BACKGROUND

Calcium is considered to be one of the most important minerals in the human body. It is required for maintaining bone mineral density, is essential for exocytosis of neurotransmitters, takes part in the contraction of muscle cells, replaces sodium as the depolarizing mineral in the heart, and participates in many other physiological functions.

The bioavailability of calcium may be defined as the fraction of dietary calcium that is potentially absorbable by the intestine and can be used for physiological functions, particularly bone mineralization, or to limit bone loss (Gueguen et al., J. Am. Coll. Nutr., 2000, Vol. 19(2), pages 119S-136S). Thus, in order to meet dietary calcium recommendations, the bioavailability and replenishment of calcium from supplemental resources should be considered in addition to the natural calcium content of foods.

Average dietary intakes of calcium in the U.S. are well below the recommended dietary allowance (RDA) for every age and gender group, especially in females. Only about 25% of boys and 10% of girls ages 9 to 17 are estimated to meet the recommendations. Dairy foods provide 75% of the calcium in the American diet. However, it is typically during the most critical period for peak bone mass development that adolescents tend to replace milk with soft drinks.

The UK reference nutrient intake (RNI) for calcium for adults aged over 19 years is 700 mg/day, requirements are higher during childhood, adolescence and during lactation. A high proportion of teenage boys and girls and women aged 19-24 years fail to meet the lower reference nutrient intake (LRNI) for calcium, i.e. their intakes are likely to be inadequate.

A wide number of foods contain calcium, but the amount of calcium, provided per 100 g or per serving, and efficiently absorbed by the body and further transferred to specific needed areas in the body, vary considerably. The major source of calcium in Western diets is milk and milk products, followed by cereals and cereal products. However, the bioavailability of calcium from milk and milk products is in the region of 30% of their calcium content.

The calcium present in food articles, whether obtained from natural sources or synthetic precipitates, may comprise both organic and inorganic calcium salts. Calcium carbonate—an inorganic phase of calcium—is an authorized food additive and the main compound form commercially used in the nutrient supplement market. Calcium carbonate has six known polymorphs, three of which are anhydrous crystalline (i.e., calcite, aragonite, and vaterite), two of which are hydrated (i.e., crystalline monohydrocalcite and ikaite), and one of which is hydrated amorphous, namely, amorphous calcium carbonate (ACC). The most thermodynamically stable of these phases is calcite, whereas the least stable is ACC. ACC is a transient polymorph that precipitates out of a supersaturated solution following Ostwald's step rule. If not stabilized by any element or compound, ACC will crystallize rapidly and completely into one of the five more stable polymorphs within seconds. Solubility studies suggest dramatic differences between the calcium carbonate polymorphs. While crystalline phases are considered poorly soluble, the amorphous polymorph is approximately 120 times more soluble than calcite.

In nature, ACC is utilized by a small number of organisms, mainly crustaceans and other invertebrates that developed capabilities for stabilizing ACC in transient mineral deposition sites. These organisms require an exceptional efficient mineral source for the periodical mobilization, absorption and precipitation of calcium. In some crustaceans, such as the freshwater crayfish, ACC is stored in large quantities in specialized transient storage organs, named gastroliths. Several techniques have been reported for the synthesis and stabilization of synthetic ACC, including using phosphor-amino-acids, which allows stabilizing ACC for more than 4 months under ambient conditions (Meiron et al., J. Bone Min. Res., 2011, Vol. 26(2), pages 364-372).

A highly-bioavailable source of calcium could beneficially be used for example in the food industry, enabling high gastrointestinal (GI) absorption of ionic calcium, which can be readily used by a mammalian organism for physiological functions. Specifically, amorphous calcium carbonate can be used as a food additive to produce food articles having high dietary availability of calcium, provided that the amorphous phase thereof is stable in the foods during manufacture, at storage and/or after exposure to ambient humidity when the food container is opened by the consumer.

WO 2005/115414 discloses, for example, gastrolith organs ground to a fine powder, which is useful as pharmaceutical and nutraceutical calcium compositions. WO 2009/053967 discloses, for example, pharmaceutical and nutraceutical compositions comprising synthetic ACC stabilized by phosphorylated peptides or amino acids. WO 2014/024191 discloses, for example, a method for preparing a stable amorphous calcium carbonate, which can be obtained either in suspension or as a powder. The method comprises stepwise combination of a soluble calcium salt, a soluble carbonate, a first and second stabilizer, and a water miscible organic solvent.

Yet, even stabilized ACC is vulnerable to premature dissolution and/or crystallization due to environmental conditions, such as high moisture or humidity, low pH and/or elevated temperatures. Such destabilization conditions occur, for example, during the processing or storage of various commercial food products. It is therefore a challenge to incorporate ACC into food items so it remains amorphous from the time of production to the time of consumption.

Micro-encapsulation is a useful and widely used tool to improve the delivery of bioactive compounds, particularly probiotics, minerals, vitamins, phytosterols, lutein, fatty acids, lycopene and antioxidants, into foods. Several micro-encapsulation technologies have been developed for use in the food industry and show promise for the production of so called "functional foods". Microencapsulation promotes the delivery of vitamins and minerals to foods mainly by preventing their interaction with other food components, for example, iron bioavailability is severely affected by interactions with certain food ingredients (e.g. tannins, phytates and polyphenols). Additionally, iron catalyzes the oxidative degradation of fatty acids and vitamins. Liposome encapsulation technology is often used to deliver iron into fluid food products, as it reduces the ability of the iron to react with food components. More, by encapsulating calcium lactate in lecithin liposomes, it was possible to fortify soymilk with levels of calcium equivalent to those found in cow's milk, while preventing undesirable calcium-protein reactions (Champagne and Fustier, Current Opinion in Biotechnology, 2007, Vol. 18, pages 184-190).

There are various known processing technology approaches to produce encapsulation and delivery systems: spray-drying, freeze drying and related processes for food ingredient and nutraceutical encapsulation; spray cooling and spray chilling for food ingredient and nutraceutical encapsulation; co-extrusion for food ingredients and nutraceutical encapsulation (Encapsulation Technologies and Delivery Systems for Food Ingredients and Nutraceuticals, Woodhead Publishing, 2012, ISBN: 978-0-85709-124-6).

There remains a need in the field of functional foods, particularly in the field of calcium-enriched foods, for bioavailable, amorphous calcium carbonate formulations.

SUMMARY OF THE INVENTION

The present invention provides encapsulated and stable amorphous calcium carbonate (ACC) compositions, comprising ACC cores and encapsulation matrixes. The compositions may be used in a variety of food products, and are particularly useful as a food additive in foods comprising high water content or acidic pH. Thus, the encapsulated, stable ACC composition may provide the benefits of an amorphous form of calcium carbonate, such as an enhanced bioavailability of calcium. The disclosed encapsulated ACC compositions are stable for long periods of storage even at crystallization-promoting conditions, including, inter alia, high humidity, acidic environment or elevated temperatures.

The present invention provides, in one aspect, an encapsulated amorphous calcium carbonate (ACC) composition, comprising a plurality of ACC particles comprising an ACC core, comprising ACC and at least one agent stabilizing the ACC in amorphous form, and an encapsulation matrix comprising at least one coating layer, wherein the at least one coating layer comprises an encapsulating agent selected from the group consisting of a film forming polymer and a lipid, and wherein the at least one coating layer at least partly coats the ACC core.

In certain embodiments, the ACC substantially remains in amorphous form upon exposure to external temperature of at least 50° C. In certain embodiments, the ACC substantially remains in amorphous form upon exposure to aqueous media. In certain embodiments, the ACC substantially remains in amorphous form upon exposure to water. In certain embodiments, the ACC substantially remains in amorphous form upon exposure to acidic media. In certain embodiments, the ACC substantially remains in amorphous form upon exposure to acidic media, having a pH of about 4 to about 5.

In certain embodiments, the film forming polymer is selected from the group consisting of cellulose, a cellulose derivative, methyl methacrylate, and any combination thereof. Each possibility represents a separate embodiment of the invention. In certain embodiments, the cellulose derivative is selected from the group consisting of ethyl cellulose, methyl cellulose, hydroxypropyl cellulose, hydroxypropyl methyl cellulose, methyl ethyl cellulose, ethyl hydroxyethyl cellulose, carboxymethyl cellulose, and any combination thereof. Each possibility represents a separate embodiment of the invention.

In certain embodiments, the lipid is selected from the group consisting of an edible wax, a fatty acid, a fatty acid ester, an oil, and any combination thereof. In certain embodiments, the edible wax is selected from the group consisting of beeswax, candelilla wax, carnauba wax, Japan wax, soy wax, alfa wax, rice-bran wax, bayberry wax, castor wax, montan wax, microcrystalline wax, paraffin wax, and any combination thereof. In certain embodiments, the fatty acid is selected from the group consisting of stearic acid, oleic acid, palmitic acid, lauric acid, and any combination thereof. In certain embodiments, the fatty acid ester is a glyceride stearate or a sucrose polystearate. In certain embodiments, the oil is selected from the group consisting of a vegetable oil, liquid paraffin, a medium-chain triglyceride oil, and any combination thereof. Each possibility represents a separate embodiment of the invention.

In certain embodiments, the encapsulation matrix further comprises at least one agent selected from a natural resin, a biocompatible polymer, a prolamine protein, an agent stabilizing the ACC, a surfactant, a color and a pigment. Each possibility represents a separate embodiment of the invention. In certain embodiments, the coating layer which comprises a lipid further comprises at least one agent selected from a natural resin, a biocompatible polymer, a prolamine protein, an agent stabilizing the ACC, a surfactant, a color and a pigment. Each possibility represents a separate embodiment of the invention.

In certain embodiments, the natural resin is Shellac. In certain embodiments, the biocompatible polymer is selected from the group consisting of polyvinylpyrrolidone (PVP), polyethylene glycol (PEG), polyvinyl alcohol (PVA), and any combination thereof. In certain embodiments, the prolamine protein is Zein. In certain embodiments, the ACC stabilizing agent is independently at each occurrence selected from the group consisting of an organic acid, a sulfuric ester of a hydroxyl carboxylic acid, a sulfuric ester of a hydroxyl carboxylic acid, an organoamine compound, an organic compound comprising a hydroxyl, an organophosphorous compound or a salt thereof, a bisphosphonate compound, art organophosphate compound, an organophosphonate compound, an inorganic phosphorous acid, a polyphosphate compound, an organic surfactant, a bio-essential inorganic ion, and any combination thereof. In certain embodiments, the surfactant is selected from the group consisting of a polysorbate, a sorbitan ester, a polyoxyethylene fatty acid ester, a sucrose ester of a fatty acid, glycerol monostearate, stearoyl lactylate, lecithin, and any combination thereof. Each possibility represents a separate embodiment of the invention.

In certain embodiments of the compositions described above, the weight ratio between the ACC core and the encapsulation matrix is 1:10 to 10:1. In certain embodiments of the compositions described above, the weight ratio between the ACC core and the encapsulation matrix is 1:5 to 5:1. In certain embodiments of the compositions described above, the weight ratio between the ACC core and the encapsulation matrix is 1:3 to 3:1. In certain embodiments of the compositions described above, the weight ratio between the ACC core and the encapsulation matrix is 1:2 to 2:1. In certain embodiments of the compositions described above, the weight ratio between the ACC core and the encapsulation matrix is 1:1.

In certain embodiments of the compositions described above, the encapsulation matrix comprises at least two coating layers. In certain embodiments, the encapsulation matrix comprises at least two coating layers which comprise a film forming polymer, wherein the film forming polymer in each layer may be the same or different. In certain embodiments, the encapsulation matrix comprises at least one coating layer which comprises a film-forming polymer, and at least one coating layer which comprises a lipid. In certain embodiments, the encapsulation matrix comprises at least two coating layers which comprise a lipid, wherein the lipid in each layer may be the same or different.

In certain embodiments of the compositions described above, the encapsulation matrix comprises at least three coating layers. In certain embodiments, the encapsulation matrix comprises at least one coating layer which comprises a film forming polymer, and at least two coating layers which comprise a lipid, wherein the lipid may be the same or different. In certain embodiments, the encapsulation matrix comprises at least two coating layers which comprise a film forming polymer, wherein the film forming polymer may be the same or different, and at least one coating layer which comprises a lipid.

In certain embodiments of the compositions described above, the ACC core further comprises silica.

In certain embodiments of the compositions described above, the encapsulating matrix completely coats the ACC core.

In certain embodiments of the compositions described above, the composition is inert when mixed with a food article. In certain embodiments of the compositions described above, the composition, when mixed with the food article, does not alter the taste of the food article. In certain embodiments of the compositions described above, the composition, when mixed with the food article, does not alter the color of the food article. In certain embodiments of the compositions described above, the composition, when mixed with the food article, does not alter the pH of the food article.

In certain embodiments of the compositions described above, at least 70% of the calcium carbonate is retained in amorphous form, and remains undissolved, after the composition is exposed to an aqueous medium for at least four days. In certain embodiments of the compositions described above, at least 20% of the calcium carbonate is retained in amorphous form, and remains undissolved, after the composition is exposed to an aqueous medium for at least one week.

In certain embodiments of the compositions described above, at least 20% of the calcium carbonate is retained in amorphous form after the composition is exposed to an acidic medium for at least one week. In certain embodiments of the compositions described above, at least 10% of the calcium carbonate is retained in amorphous form after the composition is exposed to an acidic medium for at least three weeks.

In certain embodiments of the compositions described above, at least 20% of the calcium carbonate is retained in amorphous form after the composition is exposed to an aqueous medium at 95° C. for at least 2 minutes. In certain embodiments of the compositions described above, at least 20% of the calcium carbonate is retained in amorphous form after the composition is exposed to 1,200 Watt microwave radiation for at least 1.5 minutes.

The present invention n further provides, in another aspect, a food product, comprising at least one of the encapsulated ACC compositions described above.

In certain embodiments, the food product is a dairy product. In certain embodiments, the dairy product comprises fermented milk. In certain embodiments, the dairy product is acidic. In certain embodiments, the dairy product is a yogurt. In certain embodiments, the food product requires heating at a temperature of at least 50° C. before consumption. In certain embodiments, the food product is selected from the group consisting of a canned food product, a frozen food product and a powdered food product.

All the above and other characteristics of the invention and of embodiments thereof will be further understood through the following illustrative and non-limitative description of embodiments thereof, with reference to the appended drawings.

DETAILED DESCRIPTION OF THE INVENTION

Figure 1A:
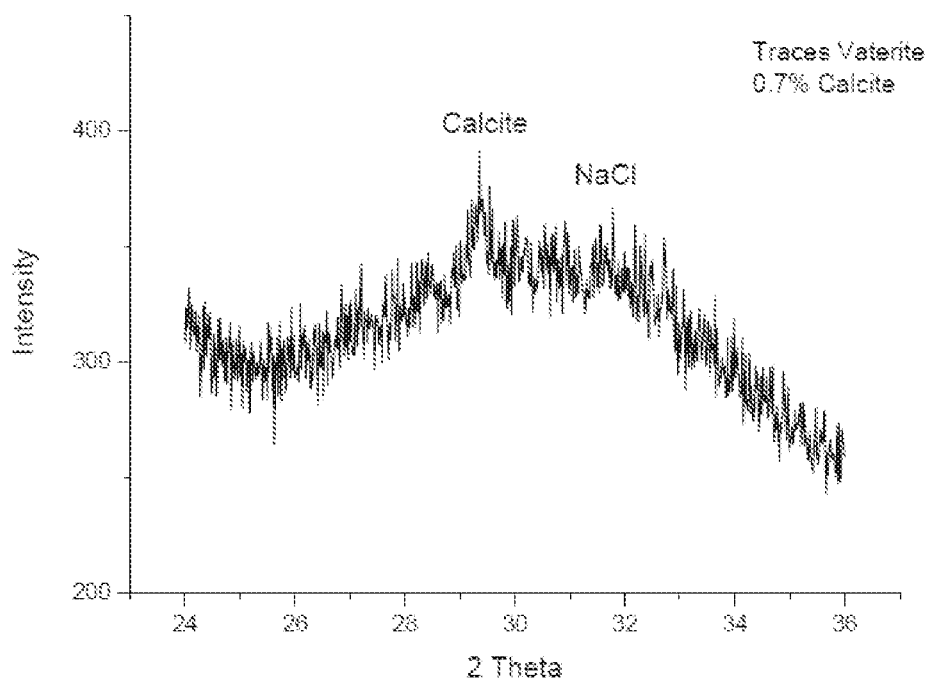
FIG. 1A: X-ray diffraction (XRD) pattern of encapsulated ACC composition (Formulation 5).

Amorphous calcium carbonate was reported to be a more soluble and absorbable source of calcium carbonate in dietary supplements than the crystalline phase of calcium carbonate. However, the present inventors, as well as others, have found that ACC, even if stabilized, has a low stability in aqueous and/or acidic environments. When exposed to such environments. ACC is rapidly converted into crystalline phases of calcium carbonate. One of the major technical challenges in encapsulating ACC is that the carrier material of encapsulates used in food products or processes should be food grade and able to form a barrier between the active agent and its surroundings. However, due to the lack of stability of amorphous calcium carbonate even at normal humidity (about 60% relative humidity, RH), its low bulk density and poor compressibility, the development of encapsulated-ACC products and the effectiveness of such encapsulations are considered very challenging.

The present inventors have found that it is not trivial to microencapsulate ACC, inter alia, because the encapsulation components are required to be approved for the designated use thereof, the encapsulation process requires elevated temperatures, and the final product application, such as food or cosmetic product, may require heating during manufacturing or processing. In addition, the texture characteristics of the final product should not be affected by the addition of the encapsulated ACC thereto. Specifically, the organoleptic characteristics of food products, such as the taste, may be affected by e.g. the encapsulation ingredients, the encapsulation ingredients, a change of pH when some of the ACC is dissolved in the food media (for example for ACC incorporated into yogurt). More, undesired powder buccal feeling may potentially be felt due to the presence of microencapsulated granules. Indeed, all ingredients of the encapsulation formulation or the ACC core should be inert for the final product in which it is incorporated to prevent spoilage of the quality of the final product, during its production, storage or consumption.

The present invention discloses, for the first time, ACC compositions that substantially overcome the technological challenges described above. As further disclosed herein for the first time, the present invention discloses that the formation of one or more ACC-coating layers of different properties, provides commercially-useful encapsulated ACC compositions, which are stable in a water-containing and/or acidic environments, are substantially stable upon exposure to high temperature, and do not alter the look-and-feel of products, including food, into which they are incorporated.

The present invention provides, in one aspect, an encapsulated amorphous calcium carbonate (ACC) composition, comprising a plurality of ACC particles comprising an ACC core, comprising ACC and at least one agent stabilizing the ACC in amorphous form, and an encapsulation matrix comprising at least one coating layer, wherein the at least one coating layer comprises an encapsulating agent selected from the group consisting of a film forming polymer and a lipid, and wherein the at least one coating layer at least partly coats the ACC core.

The term "encapsulated" refers to a process of physically interacting ACC cores with an encapsulation matrix comprising one or more encapsulation layers, without the ACC changing its chemical or structural characteristics. The term "encapsulated" is also intended to include situations in which the ACC is not completely encapsulated within or by the encapsulation matrix, that is, situations in which at least part of the ACC in a composition is not interacting with the encapsulation matrix.

As used herein, the active ingredient comprises or consists of stable ACC. In certain embodiments, the active ingredient further comprises, in addition to ACC, at least one additional active agent intended for human use or consumption. Non limiting examples of such additional active agents include nutraceutical agents, food additives, vitamins, minerals and oils. In certain embodiments, the stable ACC core comprises gastrolith organs, or a portion thereof ground to a fine powder, essentially as described in WO 2005/115414, which is hereby incorporated by reference in its entirety. In certain embodiments, the stable ACC core comprises any other biologically generated ACC harvested from any other natural resource. In certain embodiments, the stable ACC core is produced by chemical synthesis means. In certain embodiments, the stable ACC comprises a combination of harvested natural and synthesized stable ACC.

The active ingredient of the encapsulated stable ACC composition may comprise one or more cosmetic agent, nutraceutical agents or food additives in addition to the stable ACC, for example, Ma, Zn, phosphate, Vitamins B, C, or D, folic acid and/or ATP.

In some embodiments, at least 50% by wt. of the active ingredient is encapsulated within the encapsulation matrix of the encapsulated stable ACC composition. In some embodiments, at least 70% by wt. of the active ingredient is encapsulated within the encapsulation matrix of the encapsulated stable ACC composition. In some embodiments, at least 90% by wt. of the active ingredient is encapsulated within the encapsulation matrix of the encapsulated stable ACC composition.

In some embodiments, the ACC comprises more than about 30% by wt. of the active ingredient. The active ingredient may further include a nutraceutical agent or a food additive. In certain embodiments, the ACC constitutes at least 10% by wt. of the active ingredient. In certain embodiments, the active ingredient of the encapsulated stable ACC composition consists of stable ACC.

The term "encapsulation" as used herein refers to a process to entrap one substance within another substance, thereby producing particles with particle size of a few nanometers (nm) to a few millimeters (mm). As used herein, "particle size" means the longest dimension of a given particle, in any cross section thereof, including, for example a diameter in case of substantially ball shaped particles. The entrapped substance becomes protected or partially protected from external chemicals, and may be referred to as "core material", "fill", "internal phase", or "payload phase". The encapsulating substance may be referred to as "coating", "film", "membrane", "shell", "carrier material", "wall material", "external phase", "external coverage", or "matrix".

According to the principles of the present invention, the encapsulated ACC composition comprises an encapsulation matrix upon the application of which the amorphous form of calcium carbonate is maintained. It is disclosed herein for the first time that encapsulated stable ACC maintained at least about 70% of the amorphous form thereof in aqueous media for at least as long as 4 days.

The terms "amorphous", "amorphous phase", "amorphous form" and "amorphous state" can be used interchangeably, and they indicate a polymorph which is in a phase, form or state which is not in any of the crystalline or dissolved forms of calcium carbonate.

In some embodiments of the invention the encapsulating procedure provides a matrix material, wherein the stable ACC is distributed throughout the encapsulating matrix. In some embodiments, the encapsulating procedure provides a core-shell material, structure wherein the stable ACC is enclosed within a shell of the encapsulating material.

In some embodiments, the active ingredient particles are homogeneously encapsulated within the encapsulation matrix. In some embodiments, the active ingredient particles are agglomerated within the encapsulation matrix. The encapsulated ACC may include particles having a mean particle size of about 0.1-100 μm, such as 0.5-50 μm, 1-10 μm, or 0.1-4 μm. In some embodiments, the particles of the encapsulated stable ACC comprise agglomerates containing smaller particles. The encapsulated ACC may include agglomerates having a mean particle size of about 0.1-1000 μm, such as 0.2-500 μm, 1-100 μm, or 5-50 μm. Each possibility represents a separate embodiment of the invention.

In certain embodiments, the compositions of the present invention comprise particles having a mean particle size of about 0.1-50 μm. In certain embodiments, the compositions of the present invention comprise particle agglomerates having a mean particle size of about 0.2-1000 μm.

In some embodiments, the encapsulated stable ACC composition comprises up to about 15 wt % water. In some embodiments, the encapsulated stable ACC composition forms particles having a mean particle size of about 0.1-100 μm. In some embodiments, the composition comprises particle agglomerates having a mean particle size of about 0.2-1000 μm.

In some embodiments, the stable ACC is present in a weight percent of at least about 8% wt. of the total weight of the encapsulated stable ACC composition. Optionally, the stable ACC is present in a weight percent of at least about 30% of the total weight of the encapsulated stable ACC. In some embodiments, more than about 50% wt. of the stable ACC composition is dispersed and embedded within the encapsulation matrix. In certain embodiments, the compositions of the present invention are substantially free of water.

The term "encapsulation matrix" as used herein encompasses all the coating layers that at least partly coat the ACC core. Thus, in case the encapsulation matrix contains multiple coating layers, these layers together constitute the encapsulation matrix. Since not all coating procedures guarantee full coating of the ACC cores, the term "encapsulation matrix" as used herein further encompasses the excipients used in all the coating steps to coat the ACC cores, regardless of their relative surface coverage of the ACC cores. For the same reason, the term "encapsulation matrix" as used herein encompasses coating layers which fully coat the ACC cores or any coat applied beforehand, as well as partial coating layers which only partly coat the ACC cores and/or any coat applied beforehand.

The term "coating layer" as used herein indicates the layer of material covering at least part of an ACC core or an intermediate coating layer. The coating layers as described herein may be initially applied as a fluid or liquid to allow a degree of self-assembly or relocation of the coating after deposition, e.g. driven by differences in surface energy. After the coating layer achieves a desired patterning, the coating layer may be hardened, e.g. by curing and/or drying. As used herein, the term "coating" is used to indicate the process of applying a layer of material.

The term "film forming polymer" as used herein refers to a polymer capable of forming, by itself or in the presence of an auxiliary film-forming agent, a continuous and adherent film on a support.

The term "film-forming polymer" denotes mainly edible polymers chosen from cellulose derivatives, such as, for example, hydroxypropylmethyl celluloses (HPMC), ethyl celluloses (EC), methyl celluloses (MC), carboxy-methyl celluloses, hydroxypropyl celluloses (HPC) or cellulose acetates or phthalates, carrageenans, sodium, potassium or ammonium alginates, or film-forming modified starch derivatives, such as, for example, dextrins, maltodextrins, guar gum, gum tragacanth, gum arabic or xanthan gum.

The term "lipid" is widely known and used in the art and is used herein to generally refer to any naturally occurring molecule that contains hydrocarbons and is insoluble in water.

In certain embodiments, the ACC substantially remains in amorphous form upon exposure of the encapsulated composition to external temperature of at least 50° C. In certain embodiments, the ACC substantially remains in amorphous form upon exposure of the encapsulated composition to aqueous media. In certain embodiments, the ACC substantially remains in amorphous form upon exposure of the encapsulated composition to water. In certain embodiments, the ACC substantially remains in amorphous form upon exposure of the encapsulated composition to acidic media. In certain embodiments, the ACC substantially remains in amorphous form upon exposure of the encapsulated composition to acidic media, having a pH of about 4 to about 5.

It is to be understood that the present invention encompasses any encapsulating agent or a material, which is capable of providing stabilization of ACC in aqueous conditions for at least one week, for example such that the ACC retains at least 20% of the amorphous phase thereof and/or that the encapsulated composition retains at least 20% of the initial content of the ACC. Each possibility represents a separate embodiment of the invention.

The phrase "substantially stable to external temperatures, humidity or acidity" as used herein generally means that the ACC, upon interaction with the encapsulation matrix, becomes significantly less accessible and/or sensitive to the temperature, to the water content and/or to the pH of the outside environment, e.g. any medium to which the composition may be added.

As used herein, the phrase "increased ACC stability upon exposure of said composition to humidity" relates to the difference in stability upon exposure of the composition to humidity, e.g. to a humid environment, such as water, between naked ACC cores and encapsulated ACC cores. Exemplary, non-limiting methods to determine the stability of ACC composition in aqueous media are provided in the Examples section below. The term "undissolved" as used herein generally means "does not form calcium ions".

As used herein, the phrase "increased ACC stability upon exposure of said composition to acidity" relates to the difference in stability upon exposure of the composition to acidity, e.g. to an acidic environment, such as yogurt, between naked ACC cores and encapsulated ACC cores.

As used herein, the phrase "increased ACC stability upon exposure of said composition to a high temperature" relates to the difference in stability upon exposure of the composition to a temperature above 50° C., e.g. to warm environment or ingredient, such as melted wax during coating, between naked ACC cores and encapsulated ACC cores.

As used herein, the terms "increased ACC stability in aqueous media", "increased ACC stability in acidic media", and "increased ACC thermal stability" relate to the respective stability of the encapsulated ACC composition of the present invention as compared to the non-encapsulated stable forms of ACC. The term "naked ACC cores" as used herein refers to ACC cores, comprising ACC and at least one agent stabilizing the ACC in amorphous form, which are not encapsulated.

In some embodiments, the encapsulated stable ACC compositions retain at least 50% of the amorphous phase of ACC in an aqueous medium for at least one week. In certain embodiments, the encapsulated stable ACC composition retains at least 60% of the amorphous phase of ACC in an aqueous medium for at least one week, optionally at least 70% of the amorphous phase, at least 80% of the amorphous phase, or at least 90% of the amorphous phase, at least 95% of the amorphous phase, or even at least 98% of the amorphous phase of ACC in an aqueous medium for at least one week. Each possibility represents a separate embodiment of the invention. In some preferred embodiments, the ACC, which retains the amorphous phase thereof, is an undissolved ACC.

In some embodiments, the encapsulated stable ACC composition retains at least 40% of the amorphous phase of ACC in an aqueous medium for at least two weeks. Optionally, the encapsulated stable ACC composition retains at least 40% of the amorphous phase of ACC in an aqueous medium for at least three weeks, or even for at least a month or for at least two months. Each possibility represents a separate embodiment of the invention. In some preferred embodiments, the ACC, which retains the amorphous phase thereof, is an undissolved ACC.

In some embodiments, the encapsulated stable ACC composition retains at least 70% of the amorphous phase of ACC in an aqueous medium for at least four days, or at least 80% of the amorphous phase, at least 90% of the amorphous phase, at least 95%, or even at least 98% of the amorphous phase thereof. Each possibility represents a separate embodiment of the invention. In certain preferred embodiments, the ACC, which retains the amorphous phase thereof, is an undissolved ACC.

The aqueous medium may comprise water, solution, dispersion, gel, emulsion or suspension. In some embodiments, the aqueous medium includes a water-containing food article. The aqueous medium may be present during manufacturing of the food when containing the stable ACC. The aqueous medium may be present during the processing of the food when containing encapsulated stable ACC. The aqueous medium may be present during the storage of the food containing encapsulated stable ACC.

In some embodiments, the encapsulated stable ACC composition retains at least 40% of the amorphous phase of ACC in acidic aqueous media for at least one week, such as, for example 50% of the amorphous phase, 60% of the amorphous phase, 70% of the amorphous phase, 80% of the amorphous phase, 90% of the amorphous phase, 95% of the amorphous phase or 98% of the amorphous phase of ACC. Each possibility represents a separate embodiment of the invention. In some preferred embodiments, the ACC, which retains the amorphous phase thereof, is an undissolved ACC.

In some embodiments, the acidic aqueous medium comprises acidic solution, dispersion, gel, emulsion or suspension. Optionally, the aqueous medium includes or consists of a water-containing acidic food article. The pH of the acidic medium may be in a range of about 2-6.5, such as for example, 3-6, 4-5.5 or 4.5-5.

Optionally, the encapsulated stable ACC composition retains at least 40% of the amorphous phase of ACC for at least one week upon exposure to atmospheric humidity, such as, for example 50% of the amorphous phase, 60% of the amorphous phase, 70% of the amorphous phase, 80% of the amorphous phase, 90% of the amorphous phase, 95% of the amorphous phase or 98% of the amorphous phase of ACC. In some embodiments, the encapsulated stable ACC retains at least 40% of the amorphous phase of ACC for at least one week upon exposure to atmospheric humidity, such as, for example for one month, six months, one year or two years or longer.

In certain embodiments of the compositions described above, at least 70% of the calcium carbonate is retained in amorphous form, and remains undissolved, after the composition is exposed to an aqueous medium for at least four days. In certain embodiments of the compositions described above, at least 20% of the calcium carbonate is retained in amorphous form, and remains undissolved, after the composition is exposed to an aqueous medium for at least one week.

In certain embodiments of the compositions described above, at least 20% of the calcium carbonate is retained in amorphous form after the composition is exposed to an acidic medium for at least one week. In certain embodiments of the compositions described above, at least 10% of the calcium carbonate is retained in amorphous form after the composition is exposed to an acidic medium for at least three weeks. Exemplary, non-limiting methods to determine the stability of ACC composition in acidic media are provided in the Examples section below. The term "acidic medium" as used herein generally refers to a medium having a pH<7, <6, <5, <4, <3, or <2, preferably pH of about 4.2-4.5.

In certain embodiments of the compositions described above, at least 20% of the calcium carbonate is retained in amorphous form after the composition is exposed to an aqueous medium at 95° C. for at least 2 minutes. In certain embodiments of the compositions described above, at least 20% of the calcium carbonate is retained in amorphous form after the composition is exposed to 1,200 Watt microwave radiation for at least 1.5 minutes.

In certain embodiments, the film forming polymer is selected from the group consisting of cellulose, a cellulose derivative, methyl methacrylate, and any combination thereof. Each possibility represents a separate embodiment of the invention. In certain embodiments, the cellulose derivative is selected from the group consisting of ethyl cellulose, methyl cellulose, hydroxypropyl cellulose, hydroxypropyl methyl cellulose, methyl ethyl cellulose, ethyl hydroxyethyl cellulose, carboxymethyl cellulose, and any combination thereof. Each possibility represents a separate embodiment of the invention.

In certain embodiments, the lipid is selected from the group consisting of an edible wax, a fatty acid, a fatty acid ester, an oil, and any combination thereof. In certain embodiments, the edible wax is selected from the group consisting of beeswax, candelilla wax, carnauba wax, Japan wax, soy wax, alfa wax, rice-bran wax, bayberry wax, castor wax, montan wax, microcrystalline wax, paraffin wax, and any combination thereof. In certain embodiments, the fatty acid is selected from the group consisting of stearic acid, oleic acid, palmitic acid, lauric acid, and any combination thereof. In certain embodiments, the fatty acid ester is a glyceride stearate or a sucrose polystearate. In certain embodiments, the oil is selected from the group consisting of a vegetable oil, liquid paraffin, a medium-chain triglyceride oil, and any combination thereof. Each possibility represents a separate embodiment of the invention.

In certain embodiments, the encapsulation matrix further comprises at least one agent selected from a natural resin, a biocompatible polymer, a prolamine protein, an agent stabilizing the ACC, a surfactant, a color and a pigment. Each possibility represents a separate embodiment of the invention. In certain embodiments, the coating layer which comprises a lipid further comprises at least one agent selected from a natural resin, a biocompatible polymer, a prolamine protein, an agent stabilizing the ACC, a surfactant, a color and a pigment. Each possibility represents a separate embodiment of the invention.

The term "natural resin" as used herein generally refers to a plant exudate. The non-limiting example of a natural resin is shellac (which has E number E904 when used as a food additive). The encapsulated stable ACC composition may comprise about 2-90% wt. natural resin. Both zein and shellac are used in food industry, inter alia, as glazing agents. In some embodiments, encapsulated stable ACC composition comprises about 2-40% wt. natural resin. In some embodiments, encapsulated stable ACC composition comprises about 5-22% wt. natural resin.

In certain embodiments, the natural resin is Shellac. In certain embodiments, the biocompatible polymer is selected from the group consisting of polyvinylpyrrolidone (PVP), polyethylene glycol (PEG), polyvinyl alcohol (PVA), and any combination thereof. In certain embodiments, the prolamine protein is Zein.

The term "edible wax" as used herein refers to synthetic waxes that are suitable for human consumption, such as food-grade petroleum products, or natural waxes obtained from plants, insects (similar to honey bees) or animals. In some embodiments, the edible wax is selected from the group consisting of beeswax, candelilla wax, carnauba wax, Japan wax, soy wax, alfa wax, rice-bran wax, bayberry wax, castor wax, montan wax, microcrystalline wax, paraffin wax and combinations thereof. Each possibility represents a separate embodiment of the invention. According to some embodiments, the edible wax is selected from the group consisting of candelilla wax, beeswax, paraffin wax and combinations thereof. Each possibility represents a separate embodiment of the invention. In some embodiments, the encapsulated stable ACC composition comprises candelilla wax, or beeswax or a combination thereof. The encapsulated stable ACC composition may comprise about 5-60% wt. edible wax. In some embodiments, the encapsulated stable ACC composition comprises about 5-50% wt. edible wax. In some embodiments, encapsulated stable ACC composition comprises about 15-26% wt. edible wax.

The term "fatty acid" as used herein generally refers to a carboxylic acid with a long aliphatic tail (chain), which is either saturated or unsaturated. The non-limiting examples of suitable fatty acids include most fatty acids, having hydrocarbon chains of 6-24 carbons, or 10-24 carbons, 14-22 carbons, or even 16-20 carbons. In other embodiments, the fatty acid is selected from the group consisting of oleic acid, stearic acid, palmitic acid, and lauric acid. The fatty acid may be saturated or unsaturated. In some preferred embodiments, the fatty acid is saturated. In certain embodiments, the fatty acid comprises stearic acid. The encapsulated stable ACC composition may comprise about 1-60% wt. fatty acid. In some embodiments, encapsulated stable ACC composition comprises about 1-25% wt. fatty acid. In other embodiments, encapsulated stable ACC composition comprises about 1-10% wt. fatty acid.

The term "fatty acid ester" as used herein generally refers to a type of ester that results from the combination of a fatty acid with an alcohol. In some embodiments, the fatty acid ester comprises glycerol monostearate. The encapsulated stable ACC composition may comprise about 5-60% wt. fatty acid ester. In some embodiments, encapsulated stable ACC composition comprises about 2-30% wt. fatty acid ester. In some embodiments, encapsulated stable ACC composition comprises about 5-22% wt. fatty acid ester. In other embodiments, encapsulated stable ACC composition comprises about 1-10% wt. fatty acid ester. In other embodiments, the fatty acid ester is a glyceride stearate or a sucrose polystearate.

The term "oil" as used herein generally refers to a nonpolar chemical substance that is a viscous liquid at ambient temperatures and is both hydrophobic and lipophilic. Optionally, the oil comprises vegetable oils, liquid paraffin, medium chain triglyceride oils or combinations thereof. In some embodiments, the oil comprises a vegetable oil. The non-limiting example of a suitable vegetable oil is a palm oil. In other embodiments, the encapsulated stable ACC comprises a medium-chain triglyceride oil. The encapsulated stable ACC composition may comprise about 10-60% wt. oil. In some embodiments, encapsulated stable ACC composition comprises about 10-30% wt. oil. In certain embodiments, the oil is selected from the group consisting of a vegetable oil, liquid paraffin, a medium-chain triglyceride oil, and any combination thereof. Each possibility represents a separate embodiment of the invention.

A biocompatible polymer suitable for use as the encapsulating agent in the present invention may be biodegradable or non-biodegradable. The non-limiting examples of a biocompatible non-biodegradable polymer include polyethylene glycol (PEG) and polyvinyl alcohol (PVA). The biodegradable polymer may comprise a polyester, such as, for example a polylactic acid, polyglycolic acid or a poly(lactic-co-glycolic acid). The encapsulated stable ACC composition may comprise about 20-60% wt. biocompatible polymer. In some embodiments, encapsulated stable ACC composition comprises about 25-55% wt. biocompatible polymer. In some embodiments, encapsulated stable ACC composition comprises about 30-40% wt. biocompatible polymer. In certain embodiments, the biocompatible polymer is selected from the group consisting of polyvinylpyrrolidone (PVP), polyethylene glycol (PEG), polyvinyl alcohol (PVA), and any combination thereof. Each possibility represents a separate embodiment of the invention.

The proteins useful for encapsulation of the stable ACC may include soy proteins, dairy proteins and/or gelatin. The non-limiting example of a suitable protein is zein. The encapsulated stable ACC composition may comprise about 5-90% wt. protein.

According to some embodiments, the encapsulated stable ACC composition comprises a surfactant or emulsifying agent. The terms "surfactant", or "emulsifying agent" may be used interchangeably. A surfactant may comprise a non-ionic, cationic, anionic, amphoteric surfactant or combinations thereof. According to some embodiments, the surfactant is a non-ionic surfactant.

Non-limiting examples of possible non-ionic organic surfactants include polysorbates, such as polyoxyethylene sorbitan monolaurate (Tween 20), polyoxyethylene sorbitan monopalmitate (Tween 40), polyoxyethylene sorbitan monostearate (Tween 60) and polyoxyethylene sorbitan monooleate (Tween 80); glyceryl stearate; polyoxyethylene (POE) fatty acid esters, such as Myrj 45, Myrj 49, Myrj 52 and Myrj 59; sorbitan fatty acid esters, such as sorbitan monolaurate (Span 20), sorbitan monopalmitate (Span 40), sorbitan monooleate (Span 80), sorbitan monostearate (Span 60); mono/diglycerides of octanoic/dectanoic acids, such as but not limited to Imwitor-742, Imwitor-308; poly(oxyethylene) alkylyl ethers, such as poly(oxyethylene) cetyl ether (Brij 52, Brij 56, Brij 58), poly(oxyethylene) palmityl ether, polyethylene oxide hexadecyl ether, polyethylene glycol cetyl ether, and the like; polyethoxylene castor oil derivatives, such as Cremophor EL, ELP and RH 40; PEG-6 octanoic/decanoic glycerides, such as Softigen 767 and the like; polyoxyethylene glycerol trioleate, such as but not limited to Tagat TO; decaglycerol mono/dioleate, such as Caprol PGE860 and the like; sucrose esters of fatty acids, such as but not limited to a sucrose ester of palm oil; and a combination thereof. Each possibility represents a separate embodiment of the invention.

In certain embodiments, the surfactant is selected from the group consisting of a polysorbate, a sorbitan ester, a polyoxyethylene fatty acid ester, a sucrose ester of a fatty acid, glycerol monostearate, stearoyl lactylate, lecithin, and any combination thereof. Each possibility represents a separate embodiment of the invention.

Non-limiting examples of possible cationic surfactants include phosphatides, such as phosphatidyl choline and the like; quaternary ammonium cationic surfactants, such as hexadecyltrimethyl ammonium bromide and the like; pyrimidinium cationic surfactants, such as, but not limited to dodecyl pyridinium chloride; and a combination thereof.

The anionic surfactants useful in the preparation of the encapsulated stable ACC include sodium alkyl sulfates, such as, but not limited to sodium lauryl sulfate; sodium alkyl sulfonates; sodium alkyl aryl sulfonates, such as sodium dodecyl benzene sulfonate and the like; sodium stearate; dioctyl sodium sulfosuccinate; sodium cholate; and combinations thereof. Each possibility represents a separate embodiment of the invention.

The amphoteric surfactant may include lecithin, N-dodecyl alanine, cocamidopropyl amino betaine or a combination thereof. Each possibility represents a separate embodiment of the invention.

The type and the amount of surfactant may be determined by a person skilled in art so as to obtain the Hydpophile-Liphophile Balance (HLB) of the surfactant or the surfactant mixture suitable for the oil-in-water emulsions. In some embodiments the encapsulated stable ACC composition comprises polysorbates, sorbitan fatty acid esters polyoxyethylene fatty acid esters or combinations thereof. Each possibility represents a separate embodiment of the invention.

Encapsulated stable ACC composition may comprise about 5-60% wt. surfactant. In some embodiments, the encapsulated stable ACC composition comprises about 5-50% wt. surfactant. In some embodiments, the encapsulated stable ACC composition comprises about 25-50% wt. surfactant. In some embodiments, encapsulated stable ACC composition comprises about 13-36% wt. surfactant.

In certain embodiments, the encapsulation matrix further comprises at least one surfactant. The term "surfactant" as used herein generally refers to a compound which lower the surface tension (or interfacial tension) between two liquids or between a liquid and a solid. In certain embodiments, the surfactant is selected from the group consisting of a polysorbate, a sorbitan ester, a polyoxyethylene fatty acid ester, a sucrose ester of a fatty acid, glycerol monostearate, stearoyl lactylate, lecithin, and any combination thereof.

In some embodiments, the encapsulation matrix comprises at least one surfactant, or emulsifying agent. Each possibility represents a separate embodiment of the invention. The surfactant or emulsifying agent according to some embodiments of the invention, are selected from the group consisting of polysorbates, sorbitan esters, polyoxyethylene fatty acid esters, stearoyl lactylate, sucrose esters of fatty acids, glycerol monostearate, lecithin, or any other food grade surfactant approved for medicinal consumption, and combinations thereof. Each possibility represents a separate embodiment of the invention. Optionally, the fatty acid ester comprises glycerol monostearate.

In certain embodiments, encapsulation matrix further comprises a color or a pigment. In certain embodiments, the color or pigment are comprised in the last or external coating layer.

According to the principles of some embodiments of the present invention, it was further surprisingly found that addition of at least one of the stabilizing agents, suitable for stabilization of the ACC in the formulation, to the encapsulating matrix, provides enhanced stability of the encapsulated ACC. Without being bound to any theory or mechanism, it is speculated that the encapsulating matrix stabilizer can replenish its presence at the ACC surface, if breached. In certain embodiments of the compositions described above, the encapsulating matrix further comprises at least one agent stabilizing or capable of stabilizing the ACC. The term "stabilizing the ACC" or "ACC stabilizer" refers to any agent which interacts with the ACC and keeps the ACC in amorphous form. The term "capable of stabilizing the ACC" refers to any agent which does not interact with the ACC, but upon interaction keeps the ACC in amorphous form.

In some embodiments, the at least one ACC stabilizer in the encapsulation matrix is the same ACC stabilizer as the at least one stabilizer in the stable ACC. Alternatively, in some embodiments, the ACC stabilizer(s) in the encapsulation matrix may be different from the one or more stabilizers in the stable ACC. As discussed above, the ACC stabilizer(s) is incorporated into the encapsulation matrix to aid in further stabilizing the ACC, in case the microencapsulation is breached e.g. due to dissolution or physical damage. In this case, the added stabilizing agent can replenish the stabilization of the surface attacked ACC. In some embodiments, the at least one stabilizer in the encapsulation matrix comprises a carboxylic acid. In some embodiments, the at least one stabilizer in the encapsulation matrix comprises a phosphorylated organic compound or a phosphonate compound. In some embodiments, the encapsulation matrix comprises a stabilizer selected from the group consisting of citric acid, lactic acid, phosphoserine, phosphothreonine and combinations thereof. Each possibility represents a separate embodiment of the invention. In certain embodiments, the encapsulation matrix comprises citric acid. In some embodiments, the stabilizer constitutes from about 0.1 to about 15% wt. of the total weight of the encapsulation matrix.

In certain embodiments, the ACC stabilizing agent is independently at each occurrence selected from the group consisting of an organic acid, a sulfuric ester of a hydroxyl carboxylic acid, a sulfuric ester of a hydroxyl carboxylic acid, an organoamine compound, an organic compound comprising a hydroxyl, an organophosphorous compound or a salt thereof, a bisphosphonate compound, an organophosphate compound, an organophosphonate compound, an inorganic phosphorous acid, a polyphosphate compound, an organic surfactant, a bio-essential inorganic ion, and any combination thereof.

The encapsulated stable ACC composition may comprise about 0.1-15% wt. stabilizer. In some embodiments, encapsulated stable ACC composition comprises about 1-10% wt. stabilizer. Optionally, the stabilizer may comprise a molecule having one or more functional groups selected from, but not limited to, hydroxyl, carboxyl, ester, amine, phosphino, phosphono, phosphate, sulfonyl, or sulfino groups. The hydroxy bearing compounds, combined with the hydroxide, optionally also bear other functions like carboxyl, etc. but with the hydroxyl not being esterified. The organic acids may comprise, for example, ascorbic acid or acetic acid, and optionally they include carboxylic acids having at least two carboxylic groups and molecular weight not larger than 250 g/mol, such as citric acid, tartaric acid, malic acid, etc. The organic acid may further include oxalic acid, malonic acid, glutaconic acid, succinic acid, maleic acid, lactic acid, aconitic acid or combinations thereof. The esters may include, for example, phosphoenolpyruvate. In another embodiment, the phosphoric or sulfuric esters of hydroxyl carboxylic acids comprise amino acids, examples of which include phosphoserine, phosphothreonine, sulfoserine, and sulfothreonine. In another embodiment, the stabilizing molecule is a phosphate ester derivative of an amino acid, such as phosphocreatine. The hydroxyl bearing compounds combined with hydroxide may comprise, for example, mono-, di- tri-, oligo-, and polysaccharides like sucrose or other polyols like glycerol. The hydroxyl bearing compounds may further comprise hydroxy acids like citric acid, tartaric acid, malic acid, etc., or hydroxyl-bearing amino acids such as serine or threonine. Each possibility represents a separate embodiment of the present invention.

Some specific unlimited examples for such ACC stabilizers that were approved for food consumption include phytic acid, citric acid, sodium pyrophosphate diabasic, Adenosine 5'-monophosphate (AMP) sodium salt, Adenosine 5'-diphosphate (ADP) sodium salt and Adenosine 5'-triphosphate (ATP) disodium salt hydrate, phosphoserine, phosphorylated amino acids, food grade surfactants, sodium stearoyl lactylate, and combinations thereof. According to some embodiments, the stabilizer comprises at least one component selected from phosphoric or sulfuric esters of hydroxyl carboxylic acids, such as phosphoenolpyruvate, phosphoserine, phosphothreonine, sulfoserine or sulfothreonine and hydroxyl bearing organic compounds, selected from mono-, di-, tri-, oligo- and poly-saccharides, for example, sucrose, mannose, glucose. The hydroxyl bearing compound may further comprise at least one alkali hydroxide, such as sodium hydroxide, potassium hydroxide and the like. The phosphorylated acids may be present in oligopeptides and polypeptides. In other embodiments of the invention, the stabilizer is an organic acid, preferably a carboxylic acid, including a monocarboxylic acid, dicarboxylic acid or tricarboxylic acid. Each possibility represents a separate embodiment of the invention. The organic acid is preferably selected from the group consisting of citric acid, oxalic acid, malonic acid, glutaconic acid, succinic acid, tartaric acid, maleic acid, lactic acid, aconitic acid, malic acid and combinations thereof.

In some embodiments of the invention, the ACC stabilizer is selected from phosphorylated amino acids, polyols and combinations thereof. In some embodiments, the stable ACC comprises a stabilizer comprising of a carboxylic acid or multiple carboxylic acids. In some embodiments, the stable ACC comprises a phosphorylated compound as a stabilizer wherein the phosphorylation is performed on the hydroxyl group of an organic compound. In some embodiments, the stable ACC comprises a stabilizer selected from the group consisting of citric acid, phosphoserine, phosphothreonine and combinations thereof. In certain embodiments, the stable ACC comprises citric acid.

The non-limiting examples of stabilizers containing phosphate, phosphite, phosphonate groups and salts or esters thereof include phytic acid, dimethyl phosphate, trimethyl phosphate, sodium pyrophosphate, tetraethyl pyrophosphate, ribulose bisphosphate, etidronic acid and other medical bisphosphonates, 3-phosphoglyceric acid salt, glyceraldehyde 3-phosphate, 1-deoxy-D-xylulose-5-phosphate sodium salt, diethylene triamine pentakis(methylphosphonic acid), nitrilotri(methylphosphonic acid), 5-phospho-D-ribose 1-diphosphate pentasodium salt, adenosine 5'-diphosphate sodium salt, adenosine 5'-triphosphate disodium salt hydrate, α-D-galactosamine 1-phosphate, 2-phospho-L-ascorbic acid trisodium salt, α-D-galactose 1-phosphate dipotassium salt pentahydrate, α-D-galactosamine 1-phosphate, O-phosphorylethanolamine, disodium salt hydrate, 2,3-diphospho-D-glyceric acid pentasodium salt, phospho (enol)pyruvic acid monosodium salt hydrate, D-glyceraldehyde 3-phosphate, sn-glycerol 3-phosphate lithium salt, D-(−)-3-phosphoglyceric acid disodium salt, D-glucose 6-phosphate sodium salt, phosphatidic acid, ibandronate sodium salt, phosphonoacetic acid, DL-2-amino-3-phosphonopropionic acid or combinations thereof. The bio-essential inorganic ions may include, inter alia, Na, K, Mg, Zn, Fe, P, S, N; P or S in the phase of oxides; or N as ammonia or nitro groups.

The stabilizer may further include phosphonate compounds such as, but not limited to phytic acid or bisphosphonates; polyphosphates, such as, but not limited to pyrophosphate or polyphosphanates or organo polyphosphates, such as, but not limited to, adenosine diphosphate (ADP) or adenosine triphosphate (ATP).

In certain embodiments of the invention, ACC is stabilized by phosphoserine (P-Ser) or phosphothreonine (P-Thr). In some embodiments, stable ACC comprises a combination of sucrose and sodium hydroxide. In some embodiments of the invention, ACC is stabilized by citric acid. Optionally ACC is stabilized by a combination of phosphoserine and citric acid.

The stable ACC may comprise a first stabilizer and a second stabilizer. In some embodiments, the first stabilizer and the second stabilizer are similar. In other embodiments, the first stabilizer and the second stabilizer comprise different stabilizers. The first and/or the second stabilizers can be independently selected from organic acids; phosphoric or sulfuric esters of hydroxyl carboxylic acids; organoamine compounds including amino acids; hydroxyl bearing organic compounds, including carbohydrates; organophosphorous compounds or salts thereof; organophosphates, organophosphonates; inorganic phosphorous acids; polyphosphates; bio-essential inorganic ions; or combinations thereof. The stable ACC can comprise more than two stabilizers, wherein the stabilizers may be same or different.

The stable ACC can comprise more than two stabilizers, wherein one or more stabilizers are added to the ACC during the formation and precipitation of the ACC; hence constituting "internal" stabilizers, and another one or more stabilizers are added at the ACC particle surfaces after their formation; hence, constituting "external" stabilizers. Further examples for stable ACC and the preparation thereof may be found in International Patent Applications Nos. WO 2009/053967 and WO 2014/024191, which are hereby incorporated by reference in their entirety.

The encapsulation matrix and the stable ACC may each comprise one or more stabilizers. At least one stabilizer comprised in an encapsulation matrix may be the same as at least one stabilizer as in the stable ACC. Optionally the stabilizer(s) comprised in the encapsulation matrix are the same as the stabilizer(s) in the stable ACC. Alternatively, the stabilizer may be a different stabilizer. The stabilizer of the encapsulation matrix can comprise any of the stabilizers disclosed hereinabove, including organic acids, phosphorylated organic acids, phosphoric or sulfuric esters of hydroxy carboxylic acids, phosphorylated amino acids and derivatives thereof, hydroxyl bearing organic compounds combined with alkali hydroxides or combinations thereof. The encapsulation matrix may include more than one stabilizer, such as two, three, four or more stabilizers. The stabilizers, comprised in the encapsulation matrix can be independently selected from the list of stabilizers disclosed hereinabove, wherein the stabilizers may be same or different. The encapsulated stable ACC composition may comprise about 0.1-20% wt. stabilizer, wherein the encapsulating matrix may comprise up to about 20% wt. stabilizer and the stable ACC may comprise 0.1-10% wt. stabilizer. Each possibility represents a separate embodiment of the invention The terms "ACC stabilizer" or "ACC stabilizing agent" as used herein are used interchangeably and refer to any substance that contributes to preserving non-encapsulated calcium carbonate in the amorphous state in substantially dry conditions, "Substantially dry conditions" or "dry" refers, in some embodiments, to an ambiance of the stable ACC, containing less than 15% wt. water relatively to the total weight of the stable ACC.

In certain embodiments of the compositions described above, the weight ratio between the ACC core and the encapsulation matrix is 1:10 to 10:1. In certain embodiments of the compositions described above, the weight ratio between the ACC core and the encapsulation matrix is 1:5 to 5:1. In certain embodiments of the compositions described above, the weight ratio between the ACC core and the encapsulation matrix is 1:3 to 3:1. In certain embodiments of the compositions described above, the weight ratio between the ACC core and the encapsulation matrix is 1:2 to 2:1.

The term "thick coating" as used herein generally refers to a layer or more of coating which is heavier than the ACC component. In certain embodiments, the ACC constitutes up to 10% w/w while the coating constitutes at least 90% w/w of the particle. In certain embodiments, the ACC constitutes up to 20% w/w while the coating constitutes at least 80% w/w of the particle. In certain embodiments, the ACC constitutes up to 30% w/w while the coating constitutes at least 70% w/w of the particle. In certain embodiments, the ACC constitutes up to 40% w/w while the coating constitutes at least 60% w/w of the particle. In certain embodiments, the ACC constitutes less than 50% w/w while the coating constitutes more than 50% w/w of the particle.

The term "thin coating" as used herein generally refers to a layer or more of coating which is lighter than the ACC component. In certain embodiments, the ACC constitutes up to 90% w/w while the coating constitutes at least 10% w/w of the particle. In certain embodiments, the ACC constitutes up to 80% w/w while the coating constitutes at least 20% w/w of the particle. In certain embodiments, the ACC constitutes up to 70% w/w while the coating constitutes at least 30% w/w of the particle. In certain embodiments, the ACC constitutes up to 60% w/w while the coating constitutes at least 40% w/w of the particle. In certain embodiments, the ACC constitutes more than 50% w/w while the coating constitutes less than 50% w/w of the particle.

In certain embodiments, thin coating is less favorable and/or changes the taste of an edible product less than a thick coating. In certain embodiments, the reduction or an absence of the silica levels in the core formulation improves the taste of an edible product containing the coated ACC.

For example, the encapsulation experiments showed a correlation between the loading of the active ingredient and efficacy of encapsulation—an increase in the amount of the encapsulating material provides an increase in stabilization of stable ACC under wet conditions. Stable ACC loadings of as high as about 60% wt. were found to be stable in encapsulated form under experimental conditions, as exemplified herein below (see for example Formulation 21 below). In these examples, the active ingredient consisted of stable ACC. Thus, in some embodiments, the encapsulated stable ACC composition comprises at least about 8% wt. of the active ingredient, such as, for example, about 10%, about 15%, about 20%, about 30% or about 40% of the active ingredient. In some embodiments, the encapsulated stable ACC composition comprises at least about 5% wt. of stable ACC, such as, for example, about 10%, about 15%, about 20% wt., about 30% or about 40% of stable ACC. In some embodiments, the encapsulated stable ACC composition comprises more than about 20% wt. of stable ACC, or more than about 30% wt., or even more than about 40% of the stable ACC.

In some embodiments (see for example Formulation 31 below) the encapsulated stable ACC composition comprises at least about 50% of the active ingredient, for example stable ACC. The Inventors showed experimentally that after a week of refrigerated storage about 90% of the encapsulated stable ACC remained encapsulated, after two weeks of such storage, at least about 70% of the encapsulated stable ACC remained encapsulated, and after three weeks of such storage about 50% of the encapsulated stable ACC remained encapsulated, corresponding approximately to a loading of more than 25% of the active ingredient.

In certain embodiments of the compositions described above, the ACC core further comprises silica.

In certain embodiments of the compositions described above, the encapsulating matrix completely coats the ACC core.

The phrase "at least two coating layers" as used herein generally refers to the ACC core being coated in at least two coating steps, wherein the steps may involve a different or a similar coating technique, and wherein in each step a similar or different coating layer is utilized to coat the ACC core (first step) or a pre-coated ACC core (second step).

In some embodiments, the encapsulation matrix comprises a first encapsulating agent and a second encapsulating agent, wherein the first encapsulating agent and the second encapsulating agent are added to the ACC core at different steps of the preparation procedure. The first encapsulating agent and second encapsulating agent may be same or different. In certain embodiments, the first encapsulating agent and the second encapsulating agent are different. The second encapsulating agent can be added in one or more steps. The weight ratio between the first encapsulating agent and the second encapsulating agent may be from about 4:1 to about 1:4. The first encapsulating agent and/or the second encapsulating agent may comprise a combination of distinct encapsulating agents. In some embodiments, the encapsulation can be deposited in a multiple-step process, depositing a multilayer coating over the ACC particles or agglomerates. In such embodiments, the compositions of each layer may vary. In some embodiments, the internal layer formulation can provide more stability during processing of the encapsulation while the external layer provide better protection during shelf life, better stability during home cooking, or a better taste during consumption, and other functional purposes, such as controlled release of ACC upon administration. Each possibility represents a separate embodiment of the invention. In certain embodiments, the internal layer formulation can provide more thermal stability during processing of the encapsulation, while the external layer provide better protection from humidity and/or water.

In some embodiments, the encapsulation matrix is further coated with an external coating. As used herein, an external coating means a substance applied onto encapsulated ACC core after encapsulation without forming an additional matrix layer. For example, such external coating may provide water proof sealing of the encapsulation matrix. Additionally or alternatively, the coating may include one or more excipients, selected from the group consisting of lubricants, glidants, colorants, thickeners, binders, flavoring agents or combinations thereof. Suitable excipients may include, but are not limited to, titanium dioxide, silica, talc or, boric acid and/or sugar. The external coating may comprise an encapsulating agent. The encapsulating agent and the encapsulating agent of the encapsulation matrix may be same or different. In certain embodiments, the coating comprises an encapsulating material which is different from the encapsulating agent of the encapsulation matrix. In certain embodiments, the weight ratio between the encapsulation matrix and the coating may be from about 10:1 to about 1:3.

The phrase "consists of two coating layers" as used herein generally refers to the ACC core being coated in two coating steps, wherein the steps may involve a different or a similar coating technique, and wherein in each step a similar or different coating layer is utilized to coat the ACC core (first step) or a pre-coated ACC core (second step).

In certain embodiments, the encapsulation matrix consists of one coating layer which comprises at least one film-forming polymer. In certain embodiments, the encapsulation matrix consists of one coating layer which comprises at least one lipid.

In certain embodiments of the compositions described above, the encapsulation matrix consists of two coating layers. In certain embodiments, the encapsulation matrix consists of two coating layers which comprise a film forming polymer, wherein the film forming polymer in each layer may be the same or different. In certain embodiments, the encapsulation matrix consists of one coating layer which comprises a film-forming polymer and one coating layer which comprises a lipid. In certain embodiments, the encapsulation matrix consists of two coating layers which comprise a lipid, wherein the lipid in each layer may be the same or different.

According to some embodiments, the encapsulation matrix comprises at least two distinct encapsulating agents. The weight ratio between the two encapsulating agents may be from about 4:1 to about 1:4. In some embodiments, the weight ratio is from about 3:1 to about 1:3, or from about 2:1 to about 1:2. In certain preferred embodiments, the weight ratio is about 1:1.

Specifically, the encapsulation matrix may comprise a natural resin and a protein in a weight ratio of 4:1 to 1:4, or 3:1 to 1:3, or 2:1 to 1:2, or even about 1:1. Each possibility represents a separate embodiment of the invention. In other embodiments, the encapsulation matrix comprises a natural resin and a fatty acid in a weight ratio of 4:1 to 1:4, or 3:1 to 1:3, or 2:1 to 1:2, or even about 1:1. Each possibility represents a separate embodiment of the invention.

In some embodiments, the encapsulation matrix comprises a first encapsulating agent and a second encapsulating agent. Specifically, the first encapsulating agent may comprise a natural resin, a fatty acid or a combination thereof and the second encapsulating agent may comprise oil or a fatty acid ester. In other embodiments, the first encapsulating agent comprises a biocompatible polymer, and the second encapsulating agent comprises oil. In some embodiments, the first encapsulating agent comprises an edible wax, and the second encapsulating agent comprises hydrocolloid. The weight ratio between the first encapsulating agent and the second encapsulating agent may be from about 4:1 to about 1:4.

The term "hydrocolloids" as used herein refers to water soluble polymers, i.e. hydrocolloids that are capable of increasing the viscosity of the composition. In some embodiments, the hydrocolloid comprises cellulose, a cellulose derivative, such as for example, cellulose ethers, cellulose esters, or salts thereof. Cellulose derivatives include, but are not limited to, alkyl and hydroxyalkylcellulose, such as, for example methyl cellulose, ethyl cellulose, hydroxypropyl cellulose, hydroxypropyl methyl cellulose, methyl ethyl cellulose, ethyl hydroxyethyl cellulose; carboxymethyl cellulose, or combinations thereof. Each possibility represents a separate embodiment of the present invention. In some embodiments, the encapsulated stable ACC comprises a hydrocolloid selected from the group consisting of methyl cellulose, ethyl cellulose, hydroxypropyl cellulose, hydroxypropyl methyl cellulose and combinations thereof. Each possibility represents a separate embodiment of the present invention. In some embodiments, the hydrocolloid is ethyl cellulose.

Other suitable hydrocolloids include, but are not limited to, locust bean gum (LBG), guar gum, xanthan gum, gum tragacanth, lambda-carrageenan, gum arabic, gum karaya, tamarind gum, hydrolyzed gelatin, tamarind gum, fenugreek gum, cassia gum, tara gum, agar, agarose, alginate, chitin, chitosan, curdlan, gellan, konjac mannan, pectin, and carrageenan. Each possibility represents a separate embodiment of the present invention. The encapsulated stable ACC composition may comprise about 2-50% wt. hydrocolloid. In some embodiments, encapsulated stable ACC composition comprises about 2-20% wt. hydrocolloid. In some embodiments, encapsulated stable ACC composition comprises about 8-11% wt. hydrocolloid.

In some embodiments, the encapsulation matrix comprises an internal encapsulating formulation and external encapsulating formulation. The internal encapsulating formulation and external encapsulating formulation may be same or different or may comprise one or more shared components. In some preferred embodiments, the internal encapsulating formulation and external encapsulating formulation are different. Specifically, the internal encapsulating formulation may comprise a natural resin or a fatty acid or a combination thereof and the external encapsulating formulation may comprise oil and/or a fatty acid ester. The weight ratio between the internal encapsulating formulation and external encapsulating formulation may be from about 4:1 to about 1:4.

The encapsulation can be built up in more than two steps. Additional layers of encapsulation made of the same or different than the first or the second encapsulation composition can be deposited as additional coatings over the particles. In some embodiments, no more than 5 layers are used and in some embodiments no more than two encapsulation steps are used.

The phrase "at least three coating layers" as used herein generally refers to the ACC core being coated in at least three coating steps, wherein the steps may involve a different or a similar coating technique, and wherein in each step a similar or different coating layer is utilized to coat the ACC core (first step) or a pre-coated ACC core (second and third steps).

The phrase "consists of three coating layers" as used herein generally refers to the ACC core being coated in three coating steps, wherein the steps may involve a different or a similar coating technique, and wherein in each step a similar or different coating layer is utilized to coat the ACC core (first step) or a pre-coated ACC core (second and third steps).

In certain embodiments of the compositions described above, the encapsulation matrix consists of three coating layers. In certain embodiments, the encapsulation matrix consists of one coating layer which comprises a film forming polymer, and two coating layers which comprise a lipid, wherein the lipid may be the same or different. In certain embodiments, the encapsulation matrix consists of two coating layers which comprise a film forming polymer, wherein the film forming polymer may be the same or different, and one coating layer which comprises a lipid.

In certain embodiments of the compositions described above, the encapsulation matrix consists of four coating layers. In certain embodiments, the encapsulation matrix consists of one coating layer which comprises a film forming polymer, and three coating layers which comprise a lipid, wherein the lipid may be the same or different. In certain embodiments, the encapsulation matrix consists of one coating layer which comprises a lipid, and three coating layers which comprise a film forming polymer, wherein the film forming polymer may be the same or different.

In certain embodiments of the compositions described above, the encapsulation matrix consists of five coating layers. In certain embodiments, the encapsulation matrix consists of one coating layer which comprises a film thrilling polymer, and four coating layers which comprise a lipid, wherein the lipid may be the same or different.

In certain embodiments, the at least one coating layer comprises or consists a fatty acid and a resin, preferably stearic acid and shellac. In certain embodiments, the at least one coating layer comprises or consists a fatty acid and a resin, preferably stearic acid and shellac, in a weight ratio of 4:1 to 1:4. In certain embodiments, the at least one coating layer which comprises or consists a fatty acid and a resin, preferably stearic acid and shellac, in a weight ratio of 4:1 to 1:4 is in a weight ratio of 3:1 to 1:1 with the stable ACC. In certain embodiments, the at least one coating layer which comprises or consists a fatty acid and a resin, preferably stearic acid and shellac, in a weight ratio of 4:1 to 1:4 is in a weight ratio of 2:1 with the stable ACC. In certain embodiments, the at least one coating layer further comprises a polymer, preferably PVP. In certain embodiments, the at least one coating layer does not comprises a protein, preferably Zein.

In certain embodiments, the at least one coating layer which comprises or consists a fatty acid and a resin, preferably stearic acid and shellac, in a weight ratio of 4:1 to 1:4 is in a weight ratio of 2:1 with the stable ACC, and further comprises an ACC stabilizer, preferably citric acid. In certain embodiments, the at least one coating layer which comprises or consists a fatty acid and a resin, preferably stearic acid and shellac, in a weight ratio of 4:1 to 1:4 is in a weight ratio of 2:1 with the stable ACC, further comprises an ACC stabilizer, preferably citric acid, in a weight ratio of 1:10 the fatty acid and the resin.

In certain embodiments, the at least one coating layer which comprises or consists a fatty acid and a resin, preferably stearic acid and shellac, in a weight ratio of 4:1 to 1:4 is in a weight ratio of 2:3 with the stable ACC, and further comprises an ACC stabilizer, preferably citric acid. In certain embodiments, the at least one coating layer which comprises or consists a fatty acid and a resin, preferably stearic acid and shellac, in a weight ratio of 4:1 to 1:4 is in a weight ratio of 2:3 with the stable ACC, further comprises an ACC stabilizer, preferably citric acid, in a weight ratio of 1:5 with the fatty acid and the resin. In certain embodiments, the at least one coating layer described above is further coated by a second coating layer comprising an oil, preferably palm oil, or a fatty-acid ester, preferably glyceryl monostearate.

In certain embodiments, the encapsulation matrix comprises or consists of at least two coating layers, wherein each coating layer comprises or consists a hydrocolloid, preferably ethyl cellulose. In certain embodiments, the encapsulation matrix comprises or consists of at least two coating layers, wherein each coating layer comprises or consists a hydrocolloid, preferably ethyl cellulose, and at least one coating layer which comprises or consists a wax and a fatty acid ester, preferably candelilla wax, sorbitan monostearate and glyceryl stearate. In certain embodiments, the encapsulation matrix does not comprise an external coating layer which comprises or consists of a hydrocolloid, preferably ethyl cellulose.

In certain embodiments, the encapsulation matrix comprises or consists of at least three coating layers which comprise or consist of a hydrocolloid, preferably ethyl cellulose, and at least one coating layer which comprises or consists a wax and a fatty acid ester, preferably candelilla wax and glyceride stearate. In certain embodiments, the encapsulation matrix comprises or consists of at least one coating layer which comprises or consist of a hydrocolloid, preferably ethyl cellulose. In certain embodiments, the encapsulation matrix comprises or consists of at least two coating layers which comprise or consist of a hydrocolloid, preferably ethyl cellulose, and Colorcon.

In certain embodiments, the encapsulation matrix comprises or consists of at least two coating layers which comprises or consists a wax, a fatty acid ester and a surfactant, preferably candelilla wax, beeswax, paraffin wax, glyceride stearate and Sisterna. In certain embodiments, the encapsulation matrix comprises or consists of at least one coating layer which comprises or consist of a hydrocolloid, preferably ethyl cellulose, and at least two coating layers which comprise or consists a wax and a fatty acid, preferably beeswax wax and stearic acid.

In certain embodiments, the encapsulation matrix comprises or consists of at least one coating layer which comprises or consists a hydrocolloid, preferably ethyl cellulose, and at least one coating layer which comprises or consists a wax and a fatty acid ester, preferably candelilla wax, sorbitan monostearate and sorbitan tristearate. In certain embodiments, the encapsulation matrix comprises or consists of at least four coating layers, wherein the first (inner) coating layer comprises or consists of a biocompatible polymer, preferably polyethylene glycol (PEG) and polyvinyl alcohol (PVA); the second coating layer comprises or consists of a wax, a fatty acid ester, a hydrocolloid and a fatty acid, preferably beeswax, polyoxyethylene sorbitan monooleate and sorbitan monostearate; the third coating layer comprises or consists of a wax, a fatty acid ester, a hydrocolloid and a fatty acid, preferably beeswax, polyoxyethylene sorbitan monooleate, sorbitan monostearate, methyl cellulose, and stearic acid; and the fourth (outer) coating layer comprises or consists of a wax, a fatty acid ester, a hydrocolloid and a fatty acid, preferably beeswax, polyoxyethylene sorbitan monooleate and sorbitan monostearate. In certain embodiments, the encapsulation matrix comprises or consists of at least one coating layer which comprises or consists a hydrocolloid, preferably ethyl cellulose, at least one coating layer which comprises or consists a wax and a fatty acid ester, preferably candelilla wax, sorbitan monostearate and sorbitan tristearate, and at least one coating layer which comprises or consists a wax and a fatty acid ester, preferably beeswax, sorbitan monostearate and sorbitan tristearate.

In certain embodiments, the encapsulation matrix comprises or consists of at least one coating layer which comprises or consists a hydrocolloid, preferably ethyl cellulose and Colorcon.

In certain embodiments, the ACC core comprises silica, and the encapsulation matrix comprises or consists of at least one coating layer which comprises or consists a hydrocolloid, preferably ethyl cellulose, and at least two coating layers which comprise or consist a wax, preferably carnauba wax and candelilla wax.

In certain embodiments, the ACC core comprises silica, and the encapsulation matrix comprises or consists of at least four coating layers, wherein the first (inner) coating layer comprises or consists of a hydrocolloid, preferably ethyl cellulose; and at least three coating layers which each comprises or consists of a wax, preferably rice bran wax and carnauba wax.

In certain embodiments, the ACC core comprises silica, and the encapsulation matrix comprises or consists of at least two coating layers, wherein each coating layer comprises or consists a wax, preferably carnauba wax and candelilla wax.

In certain embodiments, the ACC core comprises silica, and the encapsulation matrix comprises or consists of at least four coating layers, wherein the first (inner) coating layer comprises or consists of a hydrocolloid, preferably ethyl cellulose; the second and third coating layers each comprises or consists of a wax and a fatty acid ester, preferably candelilla wax, sorbitan monostearate and sorbitan tristearate; and the fourth (outer) coating layer comprises or consists of a wax, preferably beeswax and candelilla wax.

In certain embodiments, the ACC core comprises silica, and the encapsulation matrix comprises or consists of at least four coating layers, wherein the first (inner) coating layer comprises or consists of a hydrocolloid, preferably ethyl cellulose; and at least three coating layers which comprise or consist a wax, preferably carnauba wax and beeswax wax, and a surfactant, preferably Span 65 and Span 60.

In certain embodiments, the encapsulation matrix comprises or consists of at least four coating layers, wherein the first (inner) coating layer comprises or consists of a hydrocolloid, preferably ethyl cellulose; and at least three coating layers which comprise or consist a wax, preferably carnauba wax and beeswax wax, and a surfactant, preferably Span 65 and Span 60.

In certain embodiments, the ACC core comprises silica, and the encapsulation matrix comprises or consists of at least five coating layers, wherein the first (inner) coating layer comprises or consists of a hydrocolloid, preferably ethyl cellulose; and at least four coating layers which comprise or consist a wax, preferably carnauba wax and beeswax wax, and a surfactant, preferably Span 65 and Span 60.

In certain embodiments, the encapsulated stable ACC composition comprises about 5-75% wt. stable ACC; about 5-40% wt. natural resin; about 5-40% wt. fatty acid; and about 0.1-15% wt. stabilizer. Optionally, the encapsulated stable ACC composition comprises about 42-62% wt. stable ACC; about 2-22% wt. natural resin; about 5-22% wt. fatty acid or fatty acid ester; about 1-10% wt. stabilizer; and about 10-30% wt. oil.

In some embodiments, the encapsulated stable ACC composition comprises about 20-70% wt. stable ACC; about 2-20% wt. hydrocolloid; about 5-50% wt. edible wax; and about 5-50% wt. surfactant. Optionally, the encapsulated stable ACC composition comprises about 20-70% wt. stable ACC; about 2-20% wt. hydrocolloid; about 5-50% wt. edible wax; about 5-50% wt. surfactant and about 2-25% wt. fatty acid or fatty acid ester. In some embodiments, the encapsulated stable ACC composition comprises about 5-30% wt. stable ACC; about 25-55% wt. biocompatible polymer; about 10-30% wt. oil; about 1-10% wt. fatty acid ester; and about 25-55% wt. surfactant.

In certain embodiments of the compositions described above, the composition is inert when mixed with a food article. In certain embodiments of the compositions described above, the composition, when mixed with the food article, does not alter the taste of the food article. In certain embodiments of the compositions described above, the composition, when mixed with the food article, does not alter the color of the food article. In certain embodiments of the compositions described above, the composition, when mixed with the food article, does not alter the pH of the food article.

The present invention further provides, in another aspect, a food product, comprising at least one of the encapsulated ACC compositions described above.

For certain food products or applications, the average particle size is restricted to be below 150 μm to prevent unpleasant feeling during consumption. In some embodiments, the average particle size should be in the range of between about 100-200 μm.

In certain embodiments, the encapsulation matrix of the present invention is configured to control the release of the ACC during food digestion. As detailed herein, various formulations of encapsulated ACC, when incorporated into liquid or soft dairy products, showed stability both in terms of maintaining the amorphous structure and lack of dissolution into calcium ions. In some embodiments, the encapsulation provides controlled release of calcium in the gastrointestinal (GI) tract. In some embodiments, the encapsulation matrix is configured to provide release of stable ACC in the GI tract. In some embodiments, the encapsulation matrix is configured to provide release of the stable ACC at a pH of between 6.5 and 7.5. In some embodiments, the encapsulation matrix is configured to provide release of the stable ACC at a pH of below about 2. Optionally, the encapsulation matrix is configured to provide controlled release of the stable ACC, for example in the GI tract. Controlled release, as used herein, may be taken to mean the release of stable ACC in response to stimulation and/or time. For example, the encapsulation matrix may be configured to provide slow release along the GI tract or delayed release (e.g. to a part of the GI tract).

In some embodiments, the encapsulation matrix is configured to provide controlled release of the stable ACC. In some embodiments, the encapsulation matrix is configured to provide release of the stable ACC in the GI tract. In some embodiments, the encapsulation matrix is configured to provide release of the stable ACC at the pH of below about 2. In certain embodiments, the encapsulation matrix is configured to provide release of the stable ACC at the pH of below about 3. Optionally, the encapsulation matrix is configured to provide release of the stable ACC at the pH of below about 4.

In certain embodiments, the food product is a dairy product. In certain embodiments, the dairy product comprises fermented milk. In certain embodiments, the dairy product is acidic. In certain embodiments, the dairy product is a yogurt. In certain embodiments, the food product requires heating at a temperature of at least 50° C. before consumption. In certain embodiments, the food product is selected from the group consisting of a canned food product, a frozen food product and a powdered food product.

The present invention further provides, in another aspect, a food article comprising any one of the encapsulated ACC compositions described above.

The encapsulated stable ACC of the present invention can be incorporated in various food articles as a food additive. Specifically, the encapsulated stable ACC composition can be incorporated into food articles, containing water. The water contents of the food articles may be in a range of 5-98% of the total weight of the food article. In some embodiments, the food product containing water is acidic. In certain embodiments the encapsulated stable ACC composition incorporated into a food article remains stable upon exposure of the food article to atmospheric humidity, as further detailed herein.

In some embodiments, the encapsulated stable ACC composition incorporated into a food article remains stable throughout the shelf life of the food article. In certain embodiments, the encapsulated stable ACC composition incorporated into a food article remains stable throughout the processing of the food article. Optionally, the encapsulated stable ACC composition incorporated into a food article remains stable throughout the post-processing of the food article by a consumer (e.g. by adding milk or water or the like). The encapsulated stable ACC composition incorporated into a food article remains stable upon exposure to atmospheric humidity during storage. In these embodiments the term "remains stable" for any duration refers to retaining at least 40% of the amorphous phase of ACC, such as, for example, 50%, 60%, 70%, 80%, 90%, 95% or 98% of the amorphous phase at the end of the stated duration as compared to the amount in the same product at the beginning thereof. In some preferred embodiments, the ACC, which retains the amorphous phase thereof, is an undissolved ACC.

In some embodiments, the encapsulated stable ACC composition incorporated into a food article remains stable when the food article is stored at a temperature of about 10° C. to 25° C., such as, for example, −5° C. to 20° C. or 0° C. to 10° C.

The encapsulated stable ACC composition of the present invention can be incorporated into a dairy food article, such as, but not limited to, yogurt, milk, cream, drinks based on yogurt, milk and/or cream, including chocolate milk, flavored milk and ice coffee, sour cream, sour milk, soft cheese, cottage cheese, spread cheese, whipped cream, flavored yogurts, puddings and any other dairy product comprising at least 5% wt. water and any vegetarian or vegan substitute thereof, including for example soy based substitutes.

In certain embodiments, the food article contains water. In certain embodiments, the water content of the food article is from about 5 to about 98% wt. In certain embodiments, the pH of the food article is acidic. In certain embodiments, the food article is frozen or heated during production, storage and/or consumption. In certain embodiments, the food article is exposed to microwave radiation during production, storage and/or consumption.

According to some embodiments, there is provided a food article comprising an encapsulated stable ACC composition as disclosed herein. According to some embodiments, the encapsulated stable ACC composition retains at least 20% of the calcium carbonate or at least 30% or even at least 40% in the amorphous form thereof once consumed in a food article. According to certain embodiments, the encapsulated stable ACC composition retains at least 20% of the ACC content once consumed in a food article or at least 30% or even at least 40% of the ACC content. In some embodiments, the term "ACC content" may refer to the stable ACC, which remains undissolved. The food article may be a food article containing water. The water content of the food article may be from about 5% to about 98% wt. Optionally, the food article comprising the encapsulated stable ACC composition is stored in dry form, and liquid is added before consumption to reach a water content from about 5% to about 98% wt, and the food article may then be further stored after adding liquid for a prolonged period of time (e.g. up to 4 days or even more).

In some embodiments, the encapsulated stable ACC composition retains at least 20% of the calcium carbonate in the amorphous phase thereof after a pre-market preparation of a food article comprising the composition, in the presence of water. Optionally during such pre-market preparation, the encapsulated stable ACC is exposed to an environment having water content from about 5% to about 98% wt. for a period of at least 24 hours. Optionally, during storage of such food articles the encapsulated stable ACC is exposed to water content of less than 50% wt., or even less than 20% wt.

In some embodiments, the food article is a dairy product. In certain embodiments, the food article is an acidic dairy product. In particular embodiments, the dairy product is yogurt. Other dairy products can be milk, cream, drinks based on yogurt, milk and/or cream, including chocolate milk, flavored milk and ice coffee, sour cream, sour milk, soft cheese, cottage cheese, spread cheese, whipped cream, flavored yogurts, puddings and any other dairy product and any vegetarian or vegan substitute thereof, including for example soy based substitutes comprising at least 5% wt. water. Optionally the dairy product or its substitute comprises more than 15% wt. water and in some embodiments it comprises 50% wt. or more water.

In certain embodiments, the present invention provides a water-containing food article comprising stable ACC, wherein the ACC retains at least 20% of the amorphous phase thereof or at least 30% or even at least 40%, for at least 4 days or even at least 1 week. In some embodiments, the food article retains at least 20% of the ACC content for at least one week or at least 30% or event at least 40%. In certain embodiments, the stable ACC comprises a stabilizer. Optionally, the stable ACC comprises an encapsulating agent. In some embodiments, the stable ACC comprises a combination of a stabilizer and an encapsulating agent.

In certain embodiments, the food article is a dairy food article. In certain embodiments, the dairy food article is selected from the group consisting of a yogurt, milk, cheese, ice cream and cream. Each possibility represents a separate embodiment of the invention. In certain embodiments, the dairy food article yogurt. In certain embodiments, the thin layer coating does not effect on the taste of yogurt, the color of the yogurt, or the pH of the yogurt. In certain embodiments, the thin layer coating does not effect on the taste of yogurt, the color of the yogurt, and the pH of the yogurt.

The present invention further provides, in another aspect, a one-step method for preparing the encapsulated ACC composition described above, comprising a step selected from the group consisting of spray-drying or pan coating.

The present invention further provides, in another aspect, a multi-step method for preparing the encapsulated ACC composition described above, comprising at least two steps, each step independently selected from the group consisting of spray-drying, fluid-bed coating, pan coating, and emulsification.

The present invention further provides methods of preparation of the encapsulated stable ACC composition. In some embodiments, the method comprises providing an active ingredient comprising stable ACC and encapsulating the stable ACC within an encapsulation matrix comprising at least one encapsulating agent. Encapsulation of the active ingredient may be performed according to any known encapsulation technique, such as, but not limited spray-drying, fluid-bed coating, solution coating, pan coating, spray cooling, ultrasonic spraying, melt injection, melt extrusion, emulsification, coacervation, extrusion, co-extrusion, inclusion complexation, encapsulation by rapid expansion of supercritical fluid (RESS), freeze- or vacuum drying, preparation of nanoparticles and combinations thereof. In certain embodiments, the encapsulation technique is selected from spray-drying, fluid-bed coating, emulsification and combinations thereof. In some embodiments, encapsulation of the active ingredient is a one-step process. In other embodiments, the encapsulation procedure is a multi-step process. In particular embodiments, the encapsulation procedure is a two-step process. Each of the steps of the encapsulation procedure may include application of the encapsulation techniques listed hereinabove.

In certain embodiments, the compositions described above are produced by a one-step encapsulation process. In certain embodiments, the encapsulation process comprises spray-drying or pan coating. In certain embodiments, the compositions described above are produced by a multi-step encapsulation process. In certain embodiments, the multi-step encapsulation process comprises at least two steps independently selected from the group consisting of spray-drying, fluid-bed coating, pan coating, and emulsification. In certain embodiments, the multi-step encapsulation process comprises encapsulating the stable ACC by at least two layers which are the same or different in their composition or formulation.

In some embodiments, the method of preparation of the encapsulated ACC composition includes spray-drying. Spray-drying of active agent is commonly achieved by dissolving, emulsifying, or dispersing the active ingredient in an aqueous solution of carrier material, followed by atomization and spraying of the mixture into a hot chamber. Optionally, one may also spray-dry active agent in organic solutions.

In certain processes, especially those requiring high temperature steps which make the stable ACC vulnerable toward crystallization, it would be preferable to use organic solvents instead of water to maximize the stability of the ACC during the process and drying. In such cases the presence of water can be completely eliminated to levels, for example, below 1 wt %, 5 wt %, 10 wt %, 20 wt % or 50 wt % or 80 wt % of the solvent composition. In some embodiments any of the encapsulation processes can be performed, with encapsulation agents that are soluble in organic solvents including mixtures of organic solvents like ethanol, acetone, propane, butane, butyl acetate, butan-1-ol, butan-2-ol, methyl-propan-1-ol, methyl-propan-2-ol methyl acetate, cyclohexane, dichloromethane, hexane, ethylmethylketone, isobutene, or diethyl ether.

In some embodiments of the invention, the encapsulation procedure includes a solution comprising an aqueous phase, an organic phase or a combination thereof where the water and the organic solvents are either miscible, partially miscible or no miscible (hence forming an emulsion). Each possibility represents a separate embodiment of the invention. The organic phase may comprise ethanol, acetone or a combination thereof. The aqueous phase to organic phase weight ratio may be from about 1:8 to about 1:99 water to organic solvent. In certain embodiments, the weight ratio between the aqueous phase and the organic phase of the spray-drying solution is 1:11.5. According to some preferred embodiments, the spray-drying solution comprises a solvent consisting essentially of like ethanol, acetone, propane, butane, butyl acetate, butan-1-ol, butan-2-ol, methyl-propan-1-ol, methyl-propan-2-ol methyl acetate, cyclohexane, dichloromethane, hexane, ethylmethylketone, isobutene, diethyl ether, isopropyl-alcohol or combinations thereof.

In certain embodiments, the encapsulation process solution is essentially devoid of water due to the solubility parameters of hydrophobic encapsulation agents.

In some embodiments, the method of preparation of the encapsulated stable ACC composition includes spray-dry or fluidized-bed coating. In some embodiments, the method includes a two step encapsulation process, including spray-drying and fluidized-bed coating.

Fluidized bed coating is a technique in which a coating is applied onto powder particles in a batch process or a continuous set-up. The powder particles are suspended by an air stream at a specific temperature and sprayed with an atomized, coating material. With time, each particle will be gradually covered every time it is in the spraying zone. The coating material must have an acceptable viscosity to enable pumping and atomizing, must be thermally stable and should be able to phase a film over a particle surface. The coating material may include an aqueous solution of hydrocolloids or proteins. Alternatively, a molten lipid can be used as a coating material which can be either applied from the bottom or the top. Examples of lipids used are hydrogenated vegetable oils, fatty acids, fatty acid esters, surfactants and/or waxes. In some preferred embodiments of the invention, the fluid-bed coating material comprises a molten lipid, such, but not limited to an oil or a fatty acid ester.

According to some embodiments, the method of preparation of the encapsulated stable ACC composition involves emulsification. Emulsification procedure of a hydrophilic active ingredient may include forming a water-in-oil emulsion comprising an oil and an aqueous solution of the active ingredient; adding an encapsulating agent and, optionally, a surfactant; and collapsing the aqueous phase of the water-in-oil emulsion to phase the encapsulated active ingredient. The encapsulating agents suitable for the encapsulation by emulsification include biocompatible polymers and fatty acid esters. Oils forming an oil phase of the water-in-oil emulsion can include liquid paraffin, vegetable oils or medium chain triglyceride oils.

In some embodiments of the invention the encapsulating procedure provides a matrix material, wherein the stable ACC is distributed throughout the encapsulating matrix. In other embodiments, the encapsulating procedure provides a core-shell material, wherein the stable ACC is enclosed in a core within a shell of encapsulating material. Optionally the encapsulating procedure provides a core-shell material having ACC distributed in the encapsulating matrix. Optionally, the encapsulating procedure provides this core-shell material, being enclosed within a coating over the encapsulating material.

In certain embodiments, the ratio between the ACC powder formulation and the solvent of the coating composition is up to 1:1 to minimize crystallization of ACC. In certain embodiments, the core ACC composition is sub-coated prior to encapsulation. In some embodiments such sub-coating material comprises a hydrocolloid selected from the group consisting of methyl cellulose, ethyl cellulose, hydroxypropyl cellulose, hydroxypropyl methyl cellulose and combinations thereof. In certain embodiments the encapsulation process involves heating; in some embodiments such heating may reach 80-120° C. In certain embodiments the encapsulation is carried in a non-aqueous environment. In some embodiments the matrix composition comprises a solvent consisting essentially of ethanol, acetone, propanol, propane, butane, butyl acetate, butan-1-ol, butan-2-ol, methyl-propan-1-ol, methyl-propan-2-ol methyl acetate, cyclohexane, dichloromethane, hexane, ethylmethylketone, isobutane, diethyl ether, isopropyl-alcohol or combinations thereof. According to some embodiments, the encapsulated stable ACC composition is produced by an encapsulation procedure including either a one-step or a multi-step process. The encapsulation procedure can be selected from the group consisting of spray-drying, fluid-bed coating, solution coating, pan coating, spray cooling, ultrasonic spraying, melt injection, melt extrusion, emulsification, coacervation, extrusion, co-extrusion, inclusion complexation, encapsulation by rapid expansion of supercritical fluid (RESS), freeze- or vacuum drying, preparation of nanoparticles or combinations thereof.

According to certain embodiments, the encapsulation procedure of the encapsulated stable ACC composition is selected from the group consisting of spray-drying, fluid-bed coating, emulsification or combinations thereof.

As used herein, the term "about", when referring to a measurable value such as an amount, a temporal duration, and the like, is meant to encompass variations of +/−10%, or +/−5%, +/−1%, or even +/−0.1% from the specified value.

Having now generally described the invention, the same will be more readily understood through reference to the following examples, which are provided by way of illustration and are not intended to be limiting of the present invention.

EXAMPLES

Example 1

One-Step (Spray-Drying) Preparation of Encapsulated Stable ACC (Formulations 1-10)

Materials: The materials used were obtained as follows: stabilized ACC material from Amorphical; PVP K90 from Acros, lot AO206330001; Glycerine Distearate (Precitol ATO 5) from Gattefosse, lot 131343; Stearic acid from Merck, lot K36786561 716; Zein from Sigma, lot SLBB1867V; Shellac wax free from Fluka, lot BCBJ2843V, absolute Ethanol from J. T. Baker, lot 1104004002; Acetone from J. T. Baker, lot 1101810004; compressed nitrogen (200 atm) 99,995 purity from Maxima.

In order to encapsulate ACC, the compositions summarized in Tables 1 and 2 below were produced using spray-drying. The overall procedure for preparation of spray-dried encapsulated ACC included the following steps: (1) dissolution of the encapsulating chemicals in an organic/water solution, (2) dispersion of fine ACC agglomerates, and (3) spray-drying in a conventional lab scale spray-dryer.

The following procedure is representative for all the assessed compositions. A mixture of zein:shellac was dissolved in a mixture of ethanol:water or acetone:water or ethanol:acetone at about 40° C. Then all other inactive ingredients were dissolved in the solution. The obtained clear solution was cooled down to room temperature.

The appropriate amount of ACC was sieved through 450 micron mesh. The fraction of ≤450 micron was dispersed in pure ethanol or acetone and homogenized in a lab scale homogenizer at 10,500 rpm. The ACC dispersion was added to the encapsulating excipient solution and the obtained dispersion was spray-dried under continues stirring, inlet temperature was kept at 100-110° C., outlet temperature was kept at 75-82° C., drying gas was nitrogen, yielding granulated powder particles.

The following Tables 1 and 2 represent a variety of formulations and solvent mixtures used for assessing appropriate encapsulation formulations.

TABLE 1

Encapsulated ACC Formulations Spray-dried from Ethanol/Water.

| Ingredient (g) | 1 | 2 | 3 | 4 | 5 | 6 | 7 |
|---|---|---|---|---|---|---|---|
| Ethanol | 92 | 92 | 92 | 92 | 92 | 92 | 92 |
| Water | 8 | 8 | 8 | 8 | 8 | 8 | 8 |
| Zein | 2 |  | 1 | 1.5 |  | 1.5 | 1 |
| Zein + Shellac = 1:1 |  | 1 + 1 |  |  | 0.75 + 0.75 |  |  |
| Glyceride Stearate |  |  | 1 | 0.5 | 0.5 |  |  |
| Stearic acid |  |  |  |  |  | 0.5 | 1 |
| PVP K90 |  |  |  |  |  |  | 0.2 |
| ACC | 3 | 3 | 3 | 3 | 3 | 3 | 3 |

TABLE 2

Encapsulated ACC Formulations Spray-dried from Acetone/Water.

| Ingredient (g) | 8 | 9 | 10 |
|---|---|---|---|
| Acetone | 92 | 92 | 92 |
| Water | 8 | 8 | 8 |
| Zein | 2 |  | 1 |
| Zein + Shellac = 1:1 |  | 1 + 1 |  |
| Stearic acid |  |  | 1 |
| PVP K90 |  |  | 0.2 |
| ACC | 3 | 3 | 3 |

Formulations 5, 7, 9 and 10 were analyzed using X-ray prior to the water testing, and the XRD patterns demonstrated that the amorphous structure was mostly preserved and the spray-drying process has not caused any significant crystallization. For example, Formulation 5 showed only traces of vaterite and 0.7% of calcite (FIG. 1A).

Figure 1B:
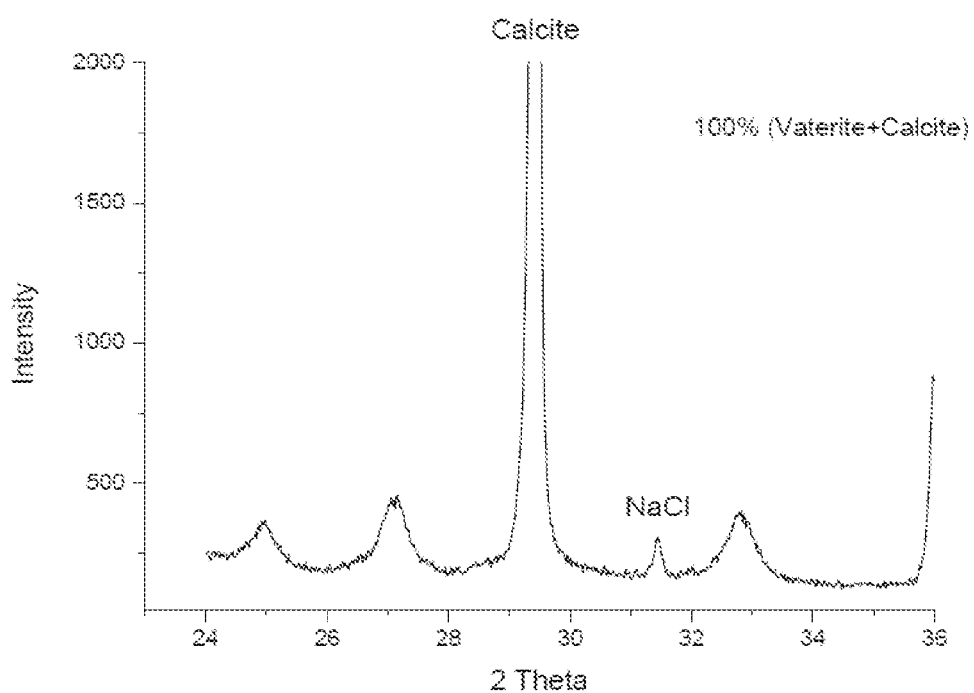
FIG. 1B: XRD pattern of encapsulated ACC composition (Formulation 5), after 30 min immersion in water.
Figure 2A:
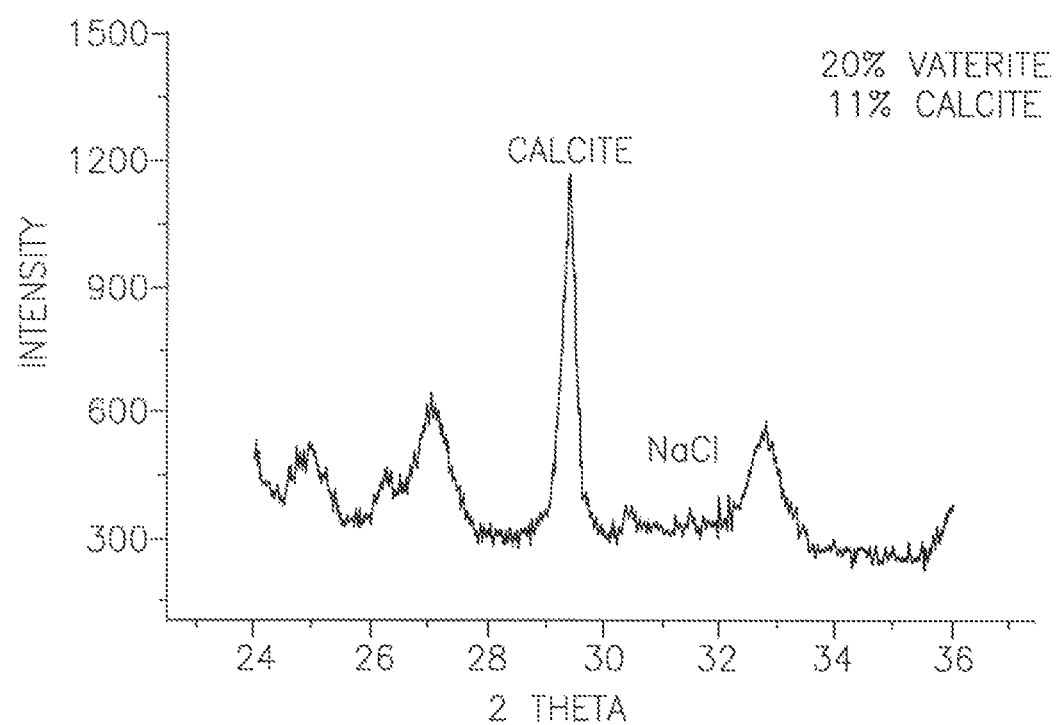
FIG. 2A: XRD pattern of encapsulated ACC composition (Formulation 11), after 30 min immersion in water.
Figure 2B:
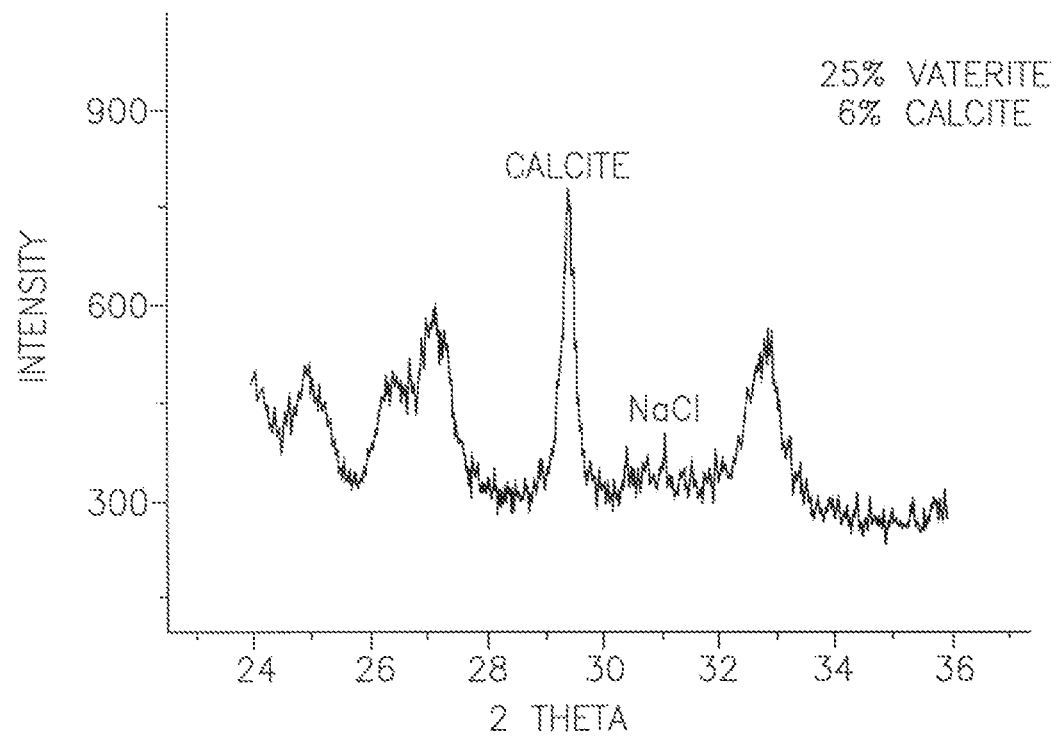
FIG. 2B: XRD pattern of encapsulated ACC composition (Formulation 12), after 30 min immersion in water.
Figure 2C:
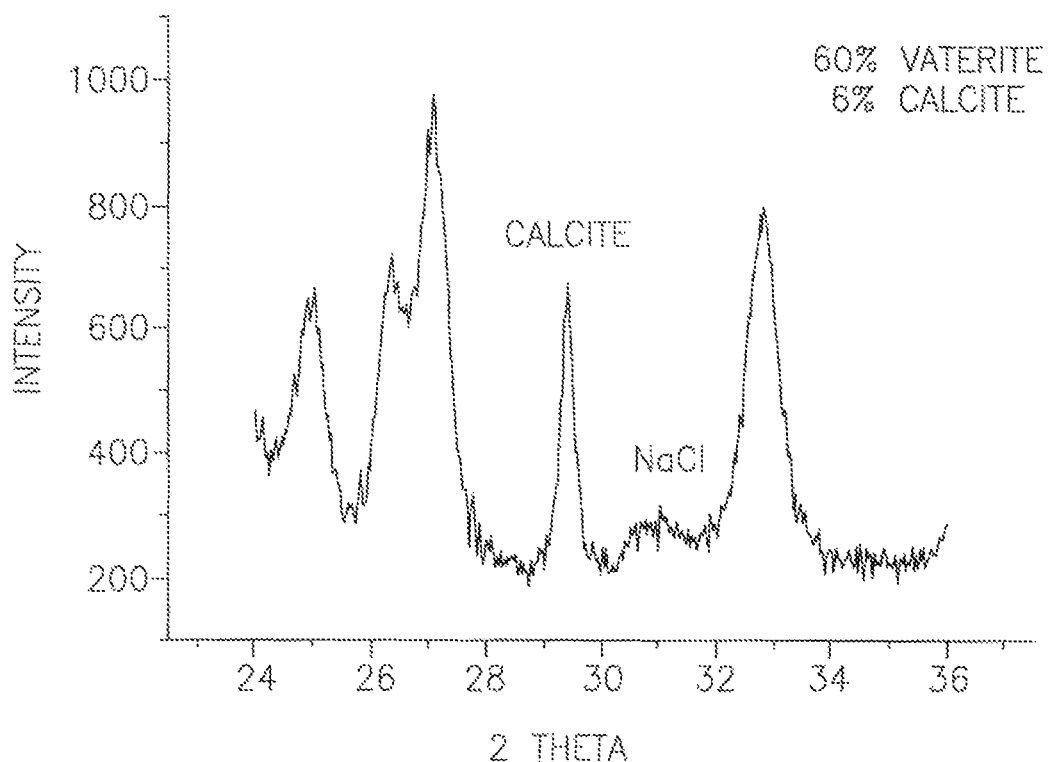
FIG. 2C: XRD pattern of encapsulated ACC composition (Formulation 13), after 30 min immersion in water.
Figure 2D:
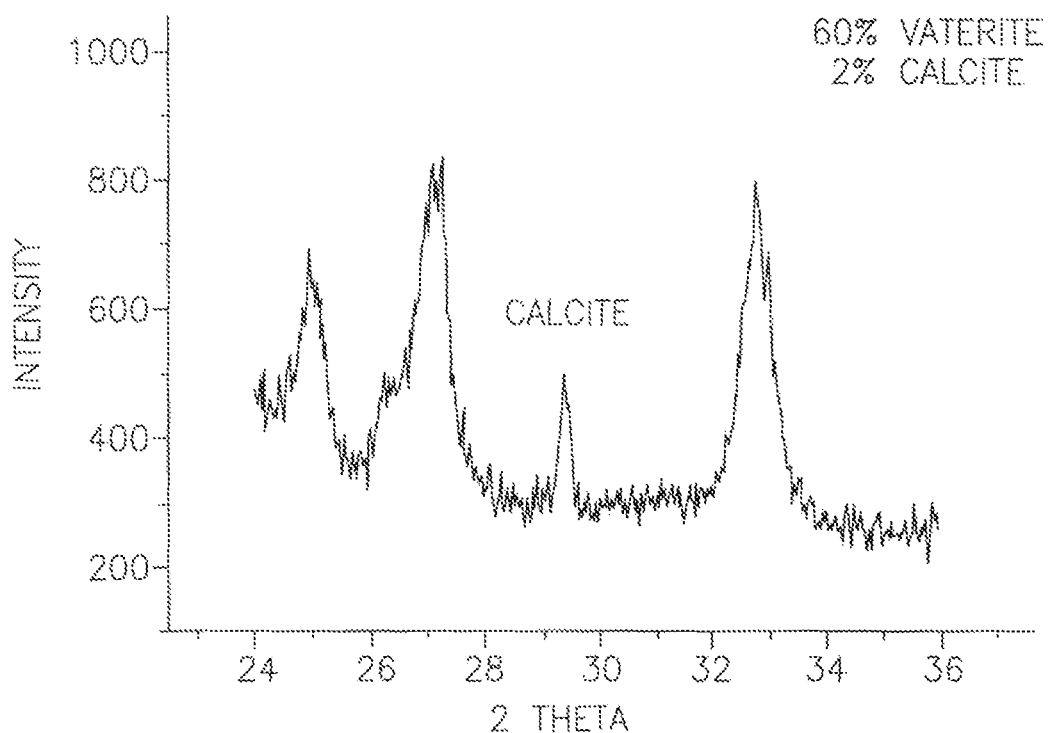
FIG. 2D: XRD pattern of encapsulated ACC composition (Formulation 14), after 30 min immersion in water.
Figure 2E:
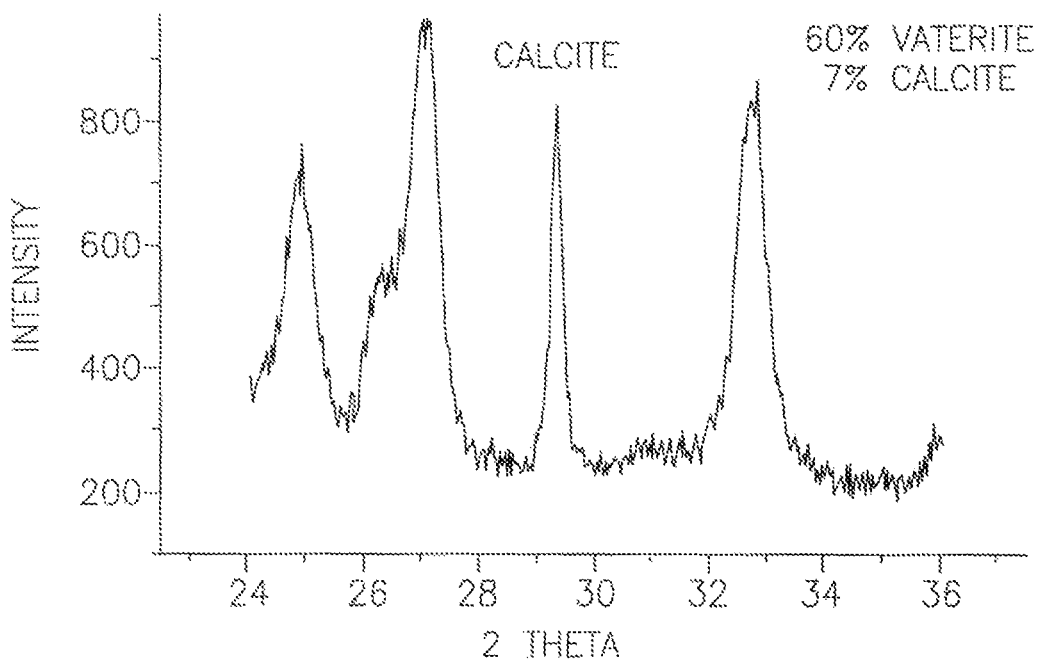
FIG. 2E: XRD pattern of encapsulated ACC composition (Formulation 15), after 30 min immersion in water.
Figure 2F:
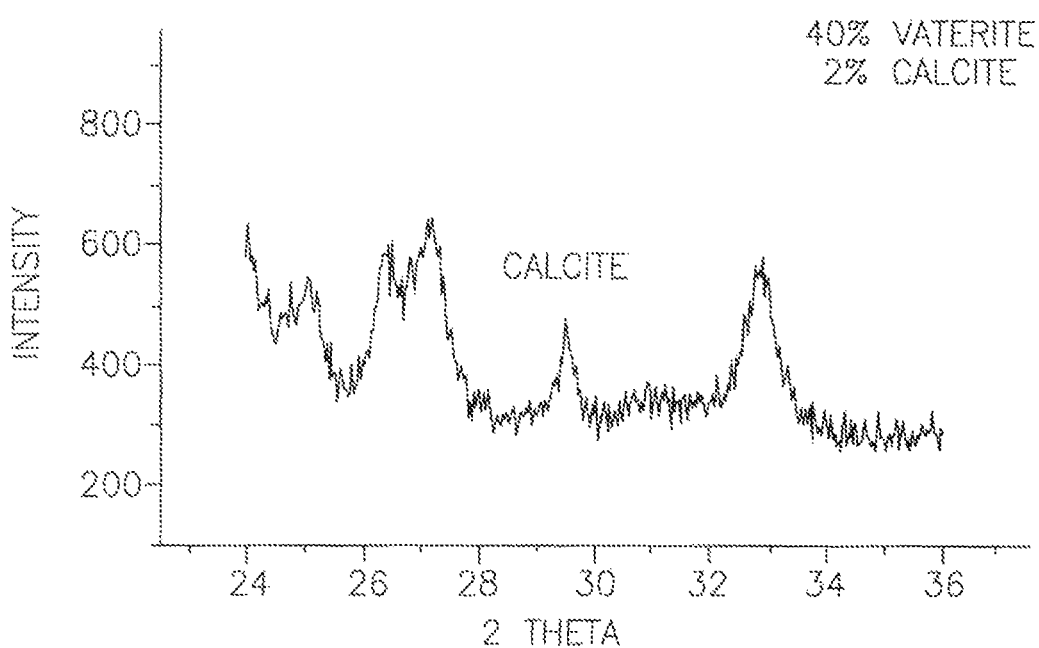
FIG. 2F: XRD pattern of encapsulated ACC composition (Formulation 16), after 30 min immersion in water.

Spray-dried batches were further tested by mixing them with water for ~30 min, filtering the powder over 0.8 µm cellulose acetate membrane and drying in vacuum oven overnight, and reanalyzed using X-ray. The XRD patterns of the water-immersed powders were completely different from the non-hydrated, spray-dried powders. The immersed powders were completely crystallized (mostly to calcite), as can be seen, for example, from the XRD pattern of FIG. 1B. Without being limited to any theory or mechanism, it is speculated that the exposure to water have caused the crystallization of the ACC.

Formulations screened by scanning electron microscopy (SEM) revealed agglomerates of ACC randomly mixed with the encapsulation material. The formed granules had irregular shape with typical particle size in the range of 5 to 20 microns. Fine ACC particles and agglomerates were detected also at the surface of the encapsulating materials. Without wishing to being bound by any specific theory or mechanism of action, this could serve an indication that at least a certain fraction of the ACC is exposed to water either at the external surface of the agglomerates or at internal surfaces formed during drying formulations in which voids are formed in the agglomerated particles.

Example 2

One-Step (Spray-Drying) Preparation of Encapsulated Stable ACC, without Use of Aqueous Media (Formulations 11-16)

To overcome the crystallization problem observed with Formulations 1-10, additional formulations were prepared (Table 3) based on zein, shellac, stearic acid and polyvinylpyrrolidone (PVP) excipients. To obtain efficient encapsulation, the weight percent of ACC was decreased from 60% to 30-35%, and use of aqueous media (water) was eliminated during the procedure. Formulations 11-16 were tested in water for 30 minutes, then filtered and dried in vacuum. The obtained powders showed significantly better stability to water penetration than Formulations 1-10. Thus, it may be concluded that shells comprising fatty acids (stearic acid) and resins (shellac) provide ACC particle with water resistance. It has also been found that the weight ratios between the fatty acids and the resins (e.g. 1:1, 0.5:1.5 or 1.5:0.5 mixtures) may be used to carefully manipulate and predetermine the degree of water resistance. The XRD results of the water immersed Formulations 11-16 are presented in Table 4 below and in FIGS. 2A-2F. The results further indicate that the absence of aqueous media in the compositions have a significantly positive effect on the degree of preventing crystallization and crystalline phases.

TABLE 3

Encapsulated ACC Formulations Spray-dried from Acetone/Ethanol mixture.

| | Form. # | | | | | |
|---|---|---|---|---|---|---|
| Ingredient (g) | 11 | 12 | 13 | 14 | 15 | 16 |
| Acetone | 30 | 30 | 30 | 31 | 32 | 33 |
| Ethanol | 70 | 70 | 70 | 69 | 68 | 67 |
| Zein | | | | | 0.5 | 0.2 |
| Shellac | 1 | 1 | 0.5 | 1.5 | 0.5 | 0.8 |
| Stearic acid | 1 | 1 | 1.5 | 0.5 | 1 | 1.5 |

TABLE 3-continued

Encapsulated ACC Formulations Spray-dried from Acetone/Ethanol mixture.

| | Form. # | | | | | |
|---|---|---|---|---|---|---|
| Ingredient (g) | 11 | 12 | 13 | 14 | 15 | 16 |
| PVP K90 | | 0.2 | 0.2 | 0.2 | 0.2 | 0.5 |
| ACC | 1 | 1 | 1.15 | 1.15 | 1.15 | 1.15 |

TABLE 4

XRD data for ACC Formulations 11-16 incubated in water 30 minutes.

| | Formulation # | | | | | |
|---|---|---|---|---|---|---|
| | 11 | 12 | 13 | 14 | 15 | 16 |
| Vaterite (%) | 20 | 25 | 60 | 60 | 60 | 40 |
| Calcite (%) | 11 | 6 | 6 | 2 | 7 | 2 |

Figure 3A:
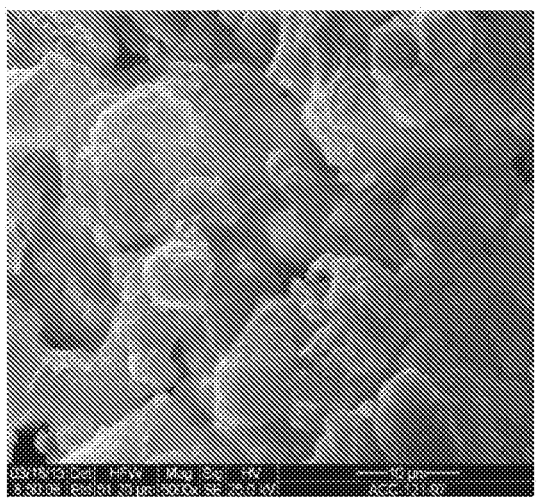
FIG. 3A: Scanning electron microscope (SEM) image of encapsulated ACC composition (Formulation 11), ×5000 magnification.
Figure 3B:
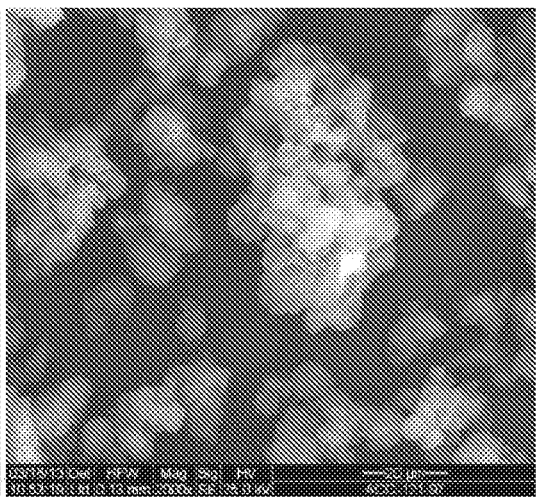
FIG. 3B: SEM image of encapsulated ACC composition (Formulation 11), ×2000 magnification.
Figure 3C:
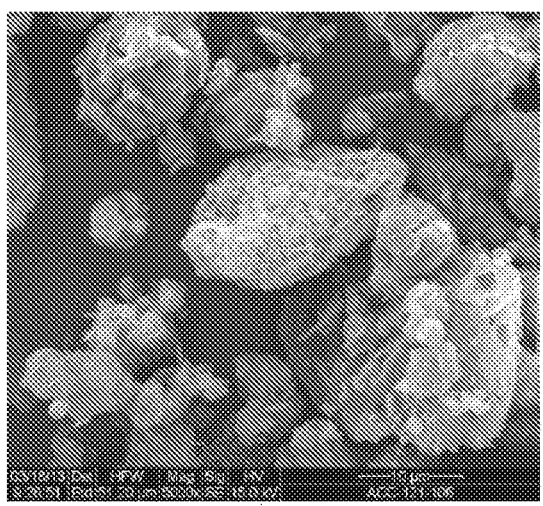
FIG. 3C: SEM image of encapsulated ACC composition (Formulation 15), ×5000 magnification.
Figure 3D:
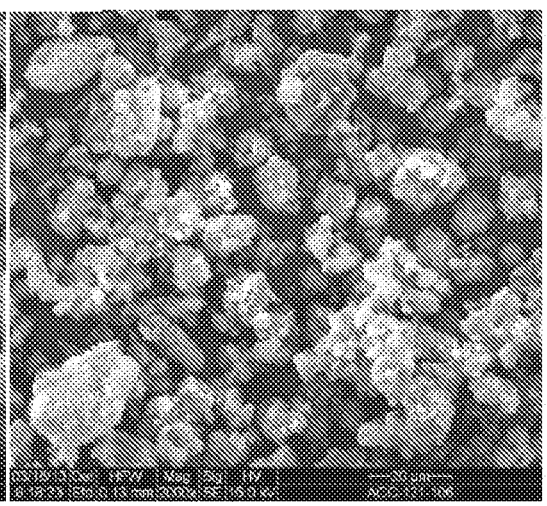
FIG. 3D: SEM image of encapsulated ACC composition (Formulation 15), ×2000 magnification.
Figure 3E:
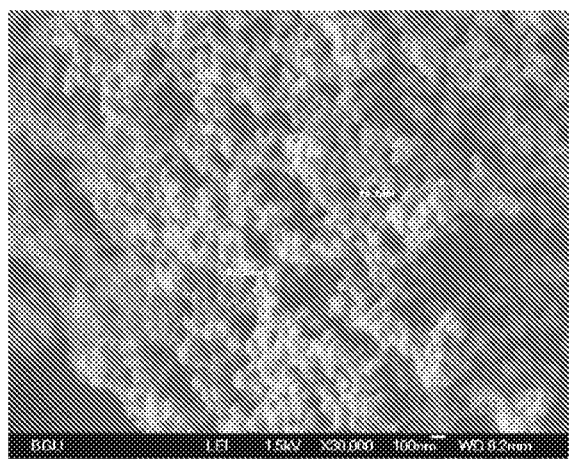
FIG. 3E: SEM image of non-encapsulated ACC, ×30,000 magnification.
Figure 4A:
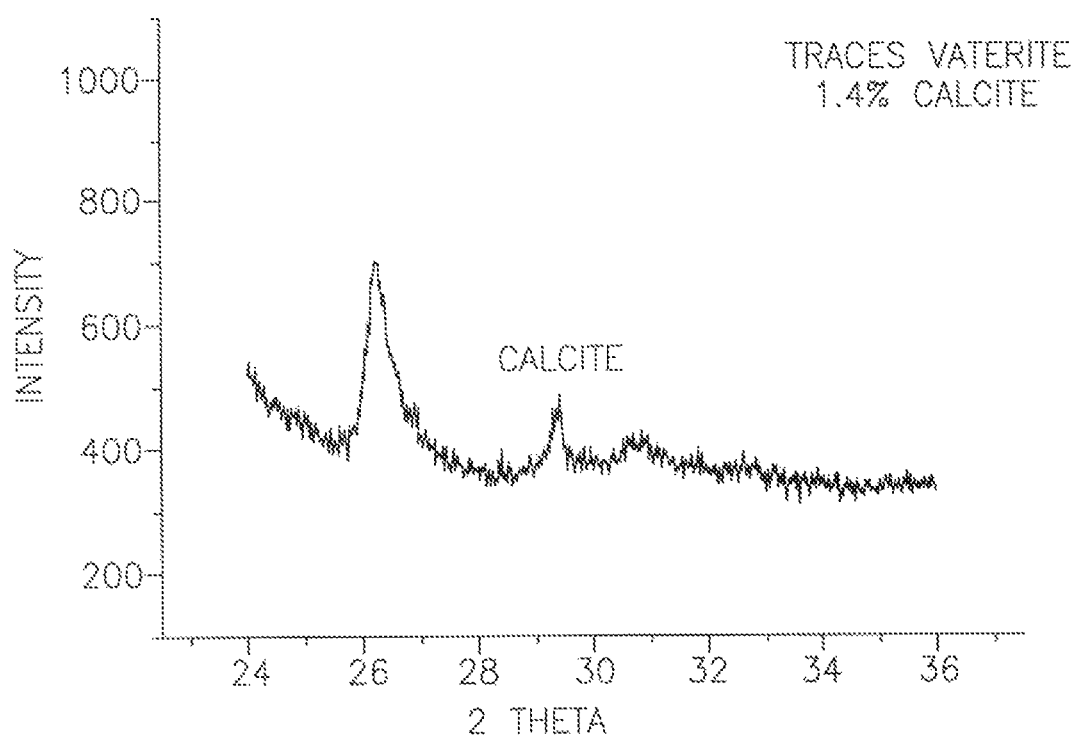
FIG. 4A: XRD pattern of encapsulated ACC composition (Formulation 17), after 30 min immersion in water.
Figure 4B:
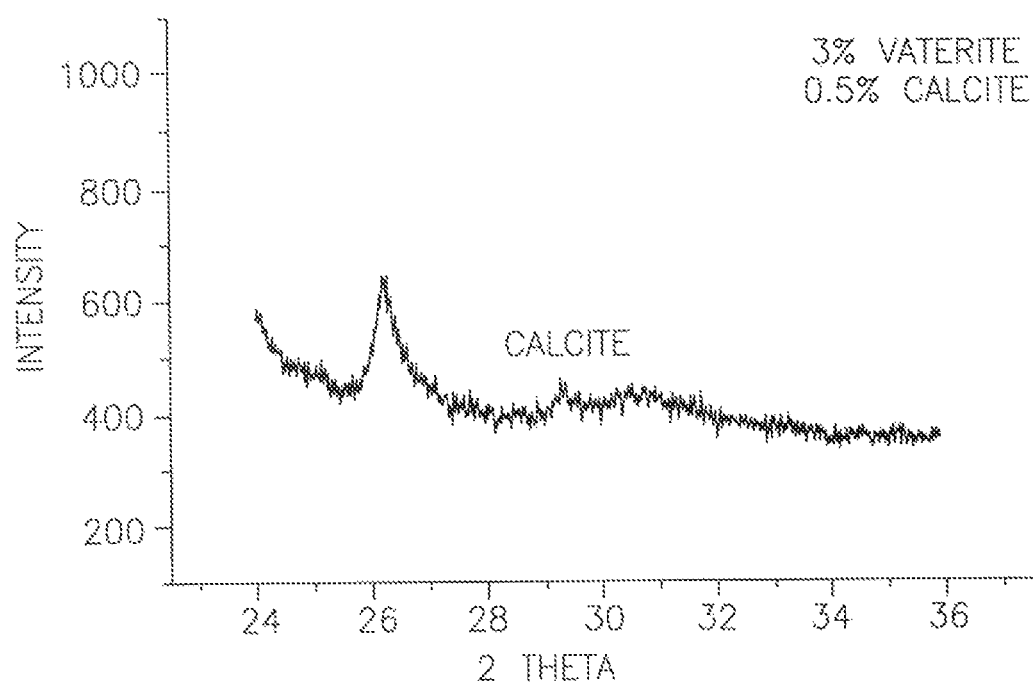
FIG. 4B: XRD pattern of encapsulated ACC composition (Formulation 18), after 30 min immersion in water.
Figure 4C:
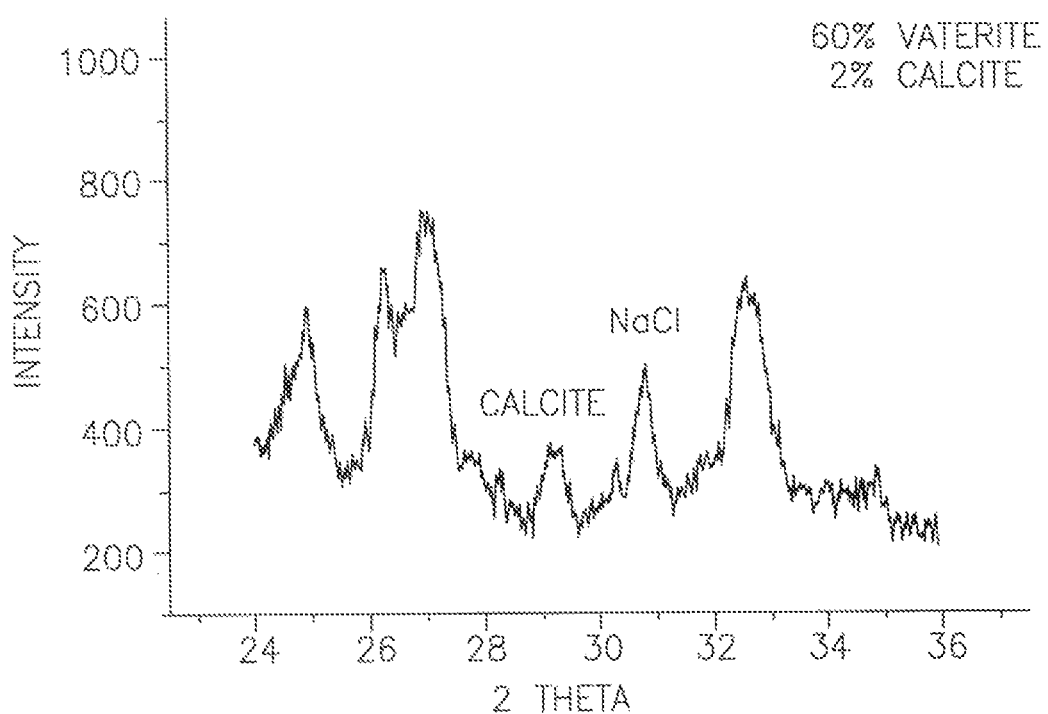
FIG. 4C: XRD pattern of encapsulated ACC composition (Formulation 19), after 30 min immersion in water.
Figure 4D:
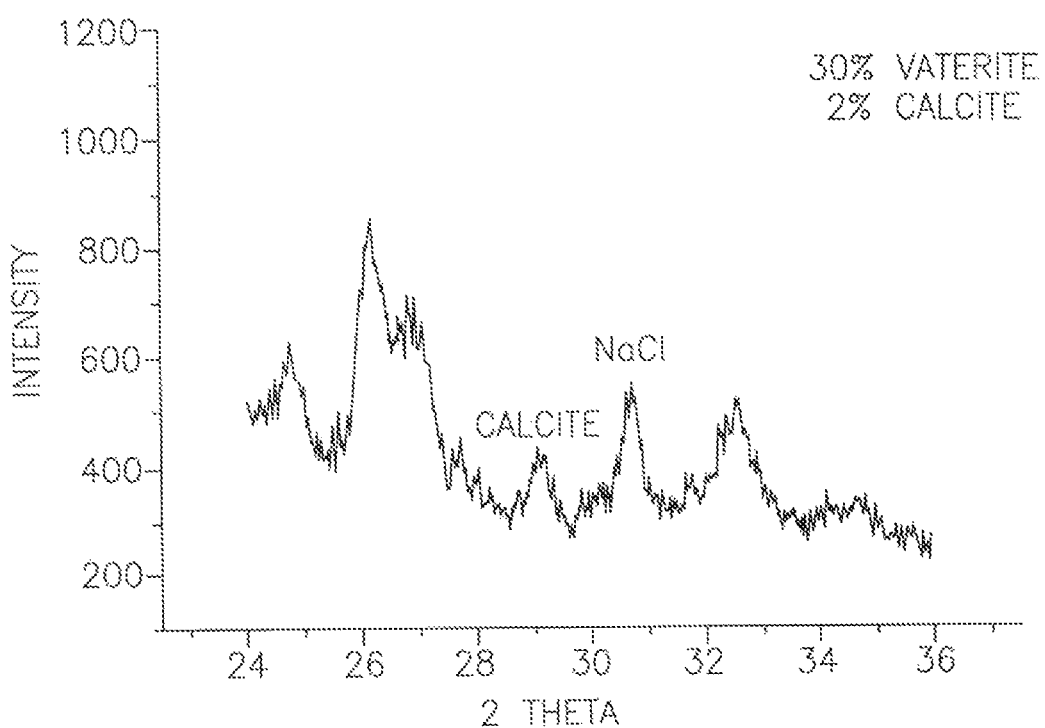
FIG. 4D: XRD pattern of encapsulated ACC composition (Formulation 20), after 30 min immersion in water.

Formulations 11 (only 31% crystallization) and 15 (67% crystallization) were SEM-analyzed to better understand ACC-Resin-Fatty acid interactions. Round shaped 3-8 micron particles and their aggregates are seen (FIGS. 3A and 3B) for Formulation 11 (ACC-33%; Stearic acid-33%; Shellac-33%). In contrast, very irregular shaped particles are observed (FIGS. 3C and 3D) for Formulation 15 (ACC-34%; Stearic acid-30%; Shellac-15%; PVP-6%; Zein-15%), which is evidence of the ingredients incompatibility and phase separation. FIG. 3E shows a comparative SEM image of non-encapsulated ACC.

Example 3

One-Step (Spray-Drying) Preparation of Encapsulated Stable ACC with Addition of a Stabilizing Agent (Formulations 17-20)

An additional spray-drying encapsulation procedure was based on the addition of 4-6% of the ACC stabilizer citric acid (CA) to the stable composition of Formulation 11. The additional compositions (Formulations 17-20) are shown in Table 5. Without wishing to being bound by a specific theory or mechanism of action, it is contemplated that the citric acid reacts with the surface of the ACC and further prevents its crystallization. However, it may also be possible that the deposition of citric acid at the surface of the ACC increases its compatibility to the adhesion of the encapsulation formulation, to form a more hermetically-sealed shell.

TABLE 5

Encapsulated ACC formulations spray-dried with addition of citric acid.

| | Form. # | | | |
|---|---|---|---|---|
| Ingredient (g) | 17 | 18 | 19 | 20 |
| Ethanol | 70 | 70 | 70 | 70 |
| Acetone | 30 | 30 | 30 | 30 |
| Shellac | 1 | 1.5 | 3 | 4.5 |
| Stearic acid | 1 | 1.5 | 3 | 4.5 |
| Citric acid | 0.2 | 0.2 | 0.6 | 0.6 |
| ACC | 1 | 1 | 3 | 3 |

Similarly to the previous experiments, the obtained compositions were immersed in water for 30 min. The dried powders were then subjected to XRD analysis, which showed (FIGS. 4A-4D) almost complete retention of ACC. Less than 3% crystallization was observed by XRD analysis.

Example 4

Two-Step (Spray-Drying and Fluid-Bed) Preparation of Encapsulated Stable ACC (Formulations 21-23)

Materials: The materials used were obtained as follows: ACC material from Amorphical; Glyceryl Monostearate (Cutina) from BASF; Stearic acid from Merck, Citric acid from Sigma; Shellac wax free from Fluka, Palm oil from, absolute Ethanol from J. T. Baker, lot 1104004002; Acetone from J. T. Baker, lot 1101810004; compressed nitrogen (200 atm) 99,995 purity from Maxima.

Process Equipment: The equipment used were obtained as follows: Semi analytical balances, Precisa; Aluminum foil bags and sealing machine, Swery Electronics; Dehumidifier S&M DHUM-16 PLUS; Homogenizer ART-Micra D8, No 11000; Buchi Mini Spray-dryer B-290 equipped with cooling block (Dehumidifier B-296), compressor and supplied gas filtering system; Lab scale fluidized bed machine; Balloons with compressed nitrogen (200 atm) 99.995% purity.

ACC Encapsulation Procedure and Composition

Compositions summarized in Table 7 were produced using spray-drying and fluid-bed coating techniques. Table 7 represents a second step encapsulation of Formulation 21 represented in Table 6. This encapsulation was performed by fluidized bed hot melt coating approach with molten encapsulating agent comprising either palm oil or glycerol monostearate (Cutina). The parameters tested for the fluidized bed steps were top/bottom spraying, feed rate, inlet temperature, fluidized air volume and atomization air pressure.

TABLE 6

Encapsulated ACC Formulation obtained by Spray-drying Encapsulation.

| | Ingredient (g) | | | |
|---|---|---|---|---|
| Form. # | ACC | Shellac | Stearic acid | Citric acid | Yield (g/%) |
| 21-1 | 165 | 37.5 | 37.5 | 15 | 218/85 |
| 21-2 | 165 | 37.5 | 37.5 | 15 | 225/88 |

TABLE 7

Encapsulated ACC Formulations obtained by fluid bed coating.

| | Ingredient (g) | | |
|---|---|---|---|
| Form. # | Formulation #21 | Palm oil | Cutina | Yield (g/%) |
| 22 | 200 | 50 | | 208/83 |
| 23 | 200 | | 50 | 220/88 |

Results

Optical Microscope Images of Produced Compositions

Figure 5A:
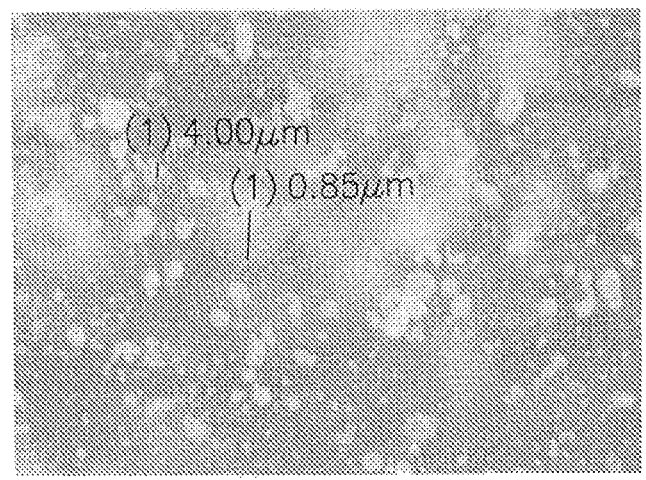
FIG. 5A: optical microscope image of encapsulated ACC composition (Formulation 21).
Figure 5B:
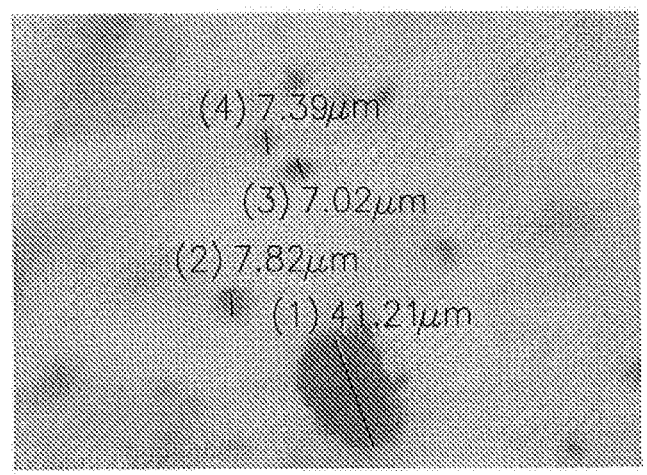
FIG. 5B: optical microscope image of encapsulated ACC composition (Formulation 22).
Figure 5C:
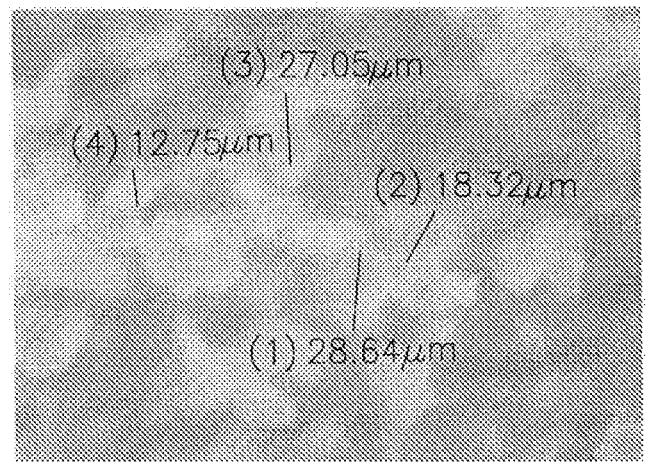
FIG. 5C: optical microscope image of encapsulated ACC composition (Formulation 23).

All processes resulted in free flowing powders. The morphology of produced powders was studied by an optical microscope. FIGS. 5A-5C represent the images of spray-dried composition (Formulation 21, FIG. 5A), fluid beds coated by palm oil (Formulation 22, FIG. 5B) and glyceryl monostearate wax (Formulation 23, FIG. 5C).

As can be seen from the Figures, spherical particles were produced in all steps. The spray-dried particles are polydispersed and include rounded shapes of 3-20 microns. Single particles of 7-8 microns or aggregates of more than 40 µm were found in the samples coated by palm oil. In contrast, samples coated by glyceryl monostearate included aggregates of 30 µm, the aggregates comprising particles of 10-18 microns.

$Ca^{+2}$ Assay Determination in Coated ACC Compositions

The amount of Ca ions in these samples was tested by titration technique. The results are shown in Table 8. The titration method was performed as follows: about 100 mg of Formulations 21-23 was each weighted into a 200 mL beaker, and about 30 mL of absolute Ethanol was added to dissolve the coating. Then, about 20 mL of 4M HCl was added to convert ACC to $Ca^{2+}$. The rest of the procedure was performed according to an analytical standard titration for determining calcium content.

TABLE 8

Calcium assays of samples produced by a one-step or a two-step process.

| Formulation # | Sample weight (mg) | Titration volume (mL) | $Ca^{2+}$ (%) | % from theoretical |
|---|---|---|---|---|
| 21 | 99 | 4.8 | 19.5 | 95.5 |
| 22 (Palm oil) | 114 | 3.7 | 13.0 | 93.0 |
| 23 (Cutina) | 104 | 3.8 | 14.7 | 105.0 |

The data presented in Table 8 is further evidence that the ACC was completely retained in amorphous phase during particle preparation.

Example 5

Stability Tests of Encapsulated Stable ACC Produced by One-Step (Spray-Drying) or Two-Step (Spray-Drying and Fluid Bed) Process Two major effects can deplete the ACC quantity in the encapsulated powder formulations: its dissolution in the yogurt liquid phase, and its recrystallization. Accordingly, the following procedure was developed for analyzing micro-encapsulated ACC stability in yogurt. Encapsulated stable ACC was compared to non-encapsulated stable ACC and crystalline calcium carbonate (CCC). Each type of calcium carbonate was added to a whole yogurt product and was stored for different periods of times, while being stirred. Then, the yogurt was centrifuged and the solid phase was evaluated using Ca titration and XRD. A blank sample of as received yogurt was also tested as a control.

An amount of 600 g of 3% Danone yogurt, produced by Strauss Group Ltd., was mixed with calcium containing formulations to have 5 wt % calcium in 100 g of yogurt. Each of the mixed batches was separated into 12 samples and at each of 6 different periods of time, 2 samples were taken from each hatch. Once sample was used for XRD and the other for Ca titration. The samples were stored at 4° C.—a typical temperature for storing yogurt in a household refrigerator.

Figure 6:
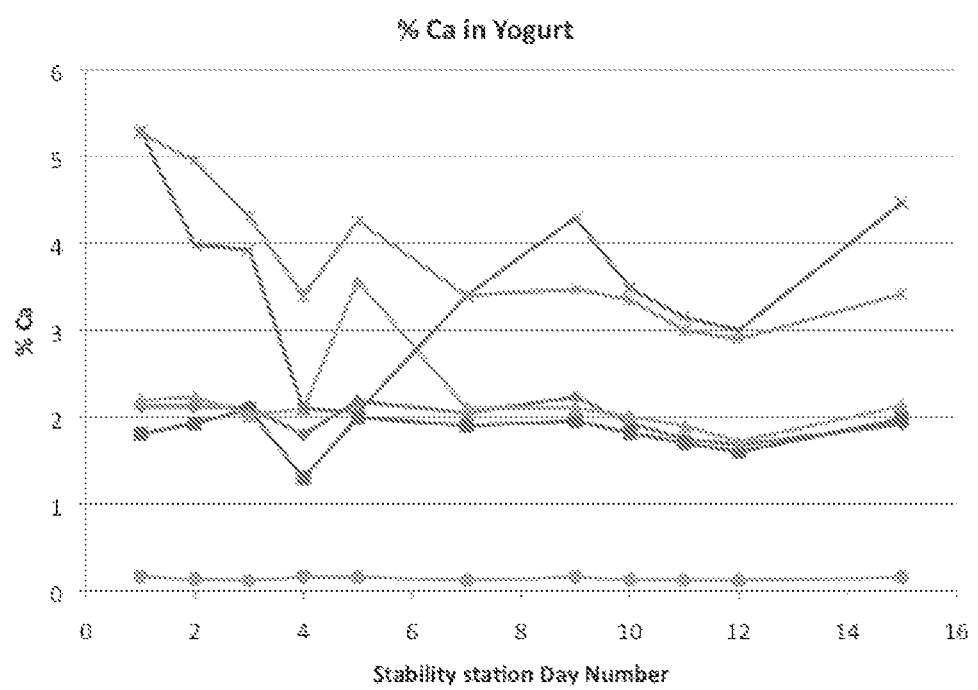
FIG. 6: Dissolution of calcium in yogurt liquid phase from: (♦) Formulation 21, (■) Formulation 22, (▲) Formulation 23, (×) crystalline calcium carbonate (CCC), (*) non-encapsulated ACC and (●) yogurt (control).

At given intervals of time, the stability of the encapsulated ACC was analyzed for the Ca content of the solid phase of the yogurt by Ca titration, initially every day and after the first week every two or three days. About 50 mL (or less) of samples were centrifuged at 4° C. The obtained results were analyzed against the CCC-yogurt and blank yogurt samples (Table 9 and FIG. 6).

The Ca titration was performed as follows. 10 ml of ddW and 1 ml of 4N HCl solution were added to each centrifuged specimen and shaken for ~10 seconds. If residual solids persisted in the solution another 1 ml of 4N HCl were added to the testing vessel. The last step was continued until the disappearance of any solids.

Then 2 ml of 0.1M Mg-EDTA and a small amount (1-2 mg) of the indicator mix (Eriochrom black T+NaCl) were added to each sample. About 10 ml DDW were added until the indicator is completely dissolved. No color is supposed to appear at this stage. 20 ml of ammonia buffer solution ($NH_4Cl$) were then added. The color of the solution was expected to turn purple. After stirring, 0.9 ml of 0.01M EDTA was added to turn the solution's color to blue-dark purple. The solution was then stirred and titrated by a flow of 0.1M EDTA placed in a burette. The titration was completed when the color turned to be clear blue with no reversing of the color.

Figure 7A:
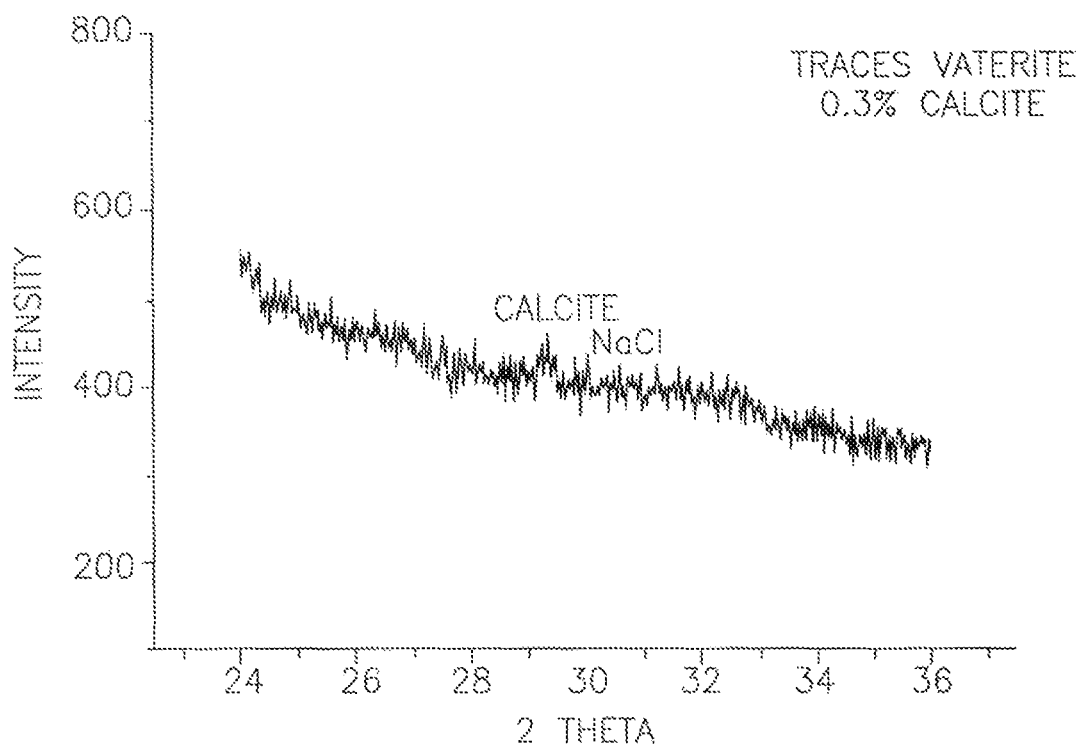
FIG. 7A: XRD pattern of encapsulated ACC composition (Formulation 21) mixed with yogurt; XRD performed on the first day of the experiment.
Figure 7B:
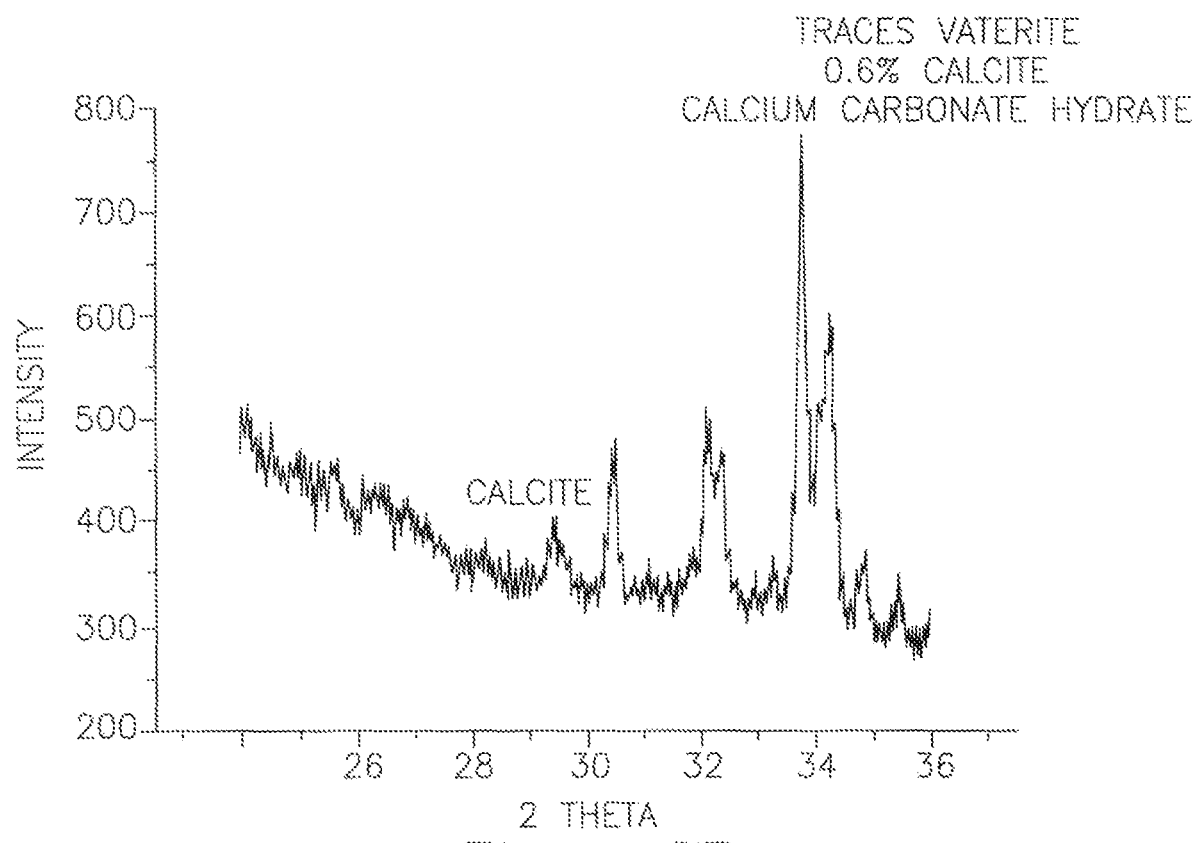
FIG. 7B: XRD pattern of encapsulated ACC composition (Formulation 21) mixed with yogurt; XRD performed on the last day of the experiment.
Figure 8A:
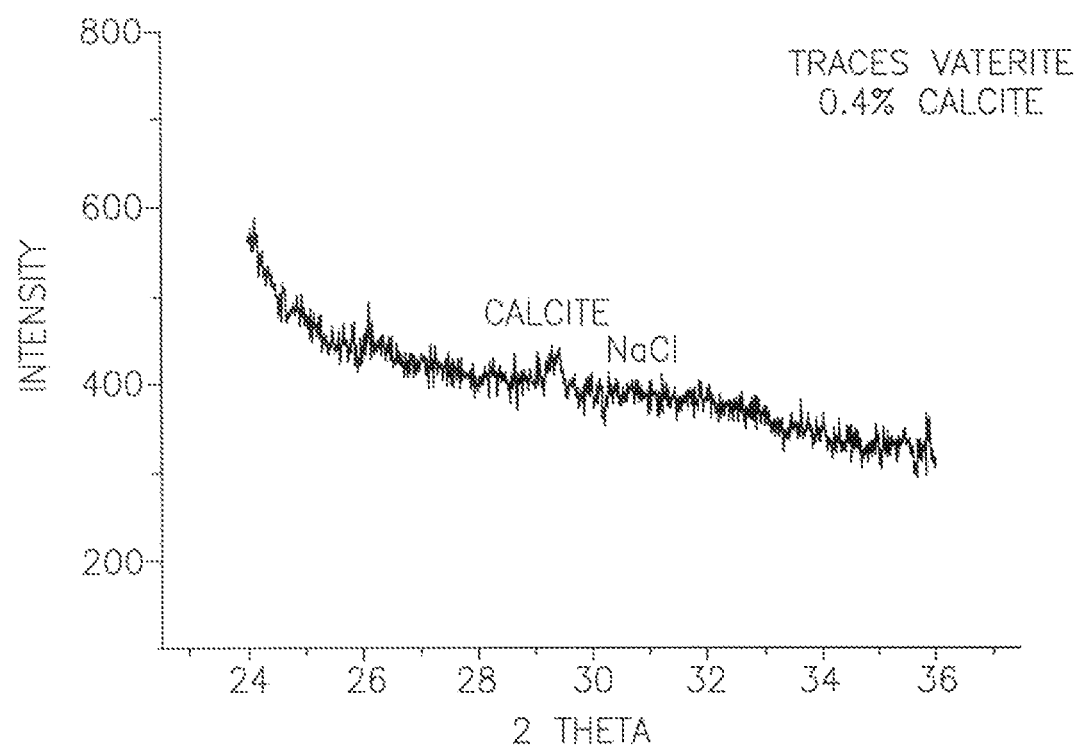
FIG. 8A: XRD pattern of encapsulated ACC composition (Formulation 22) mixed with yogurt; XRD performed on the first day of the experiment.
Figure 8B:
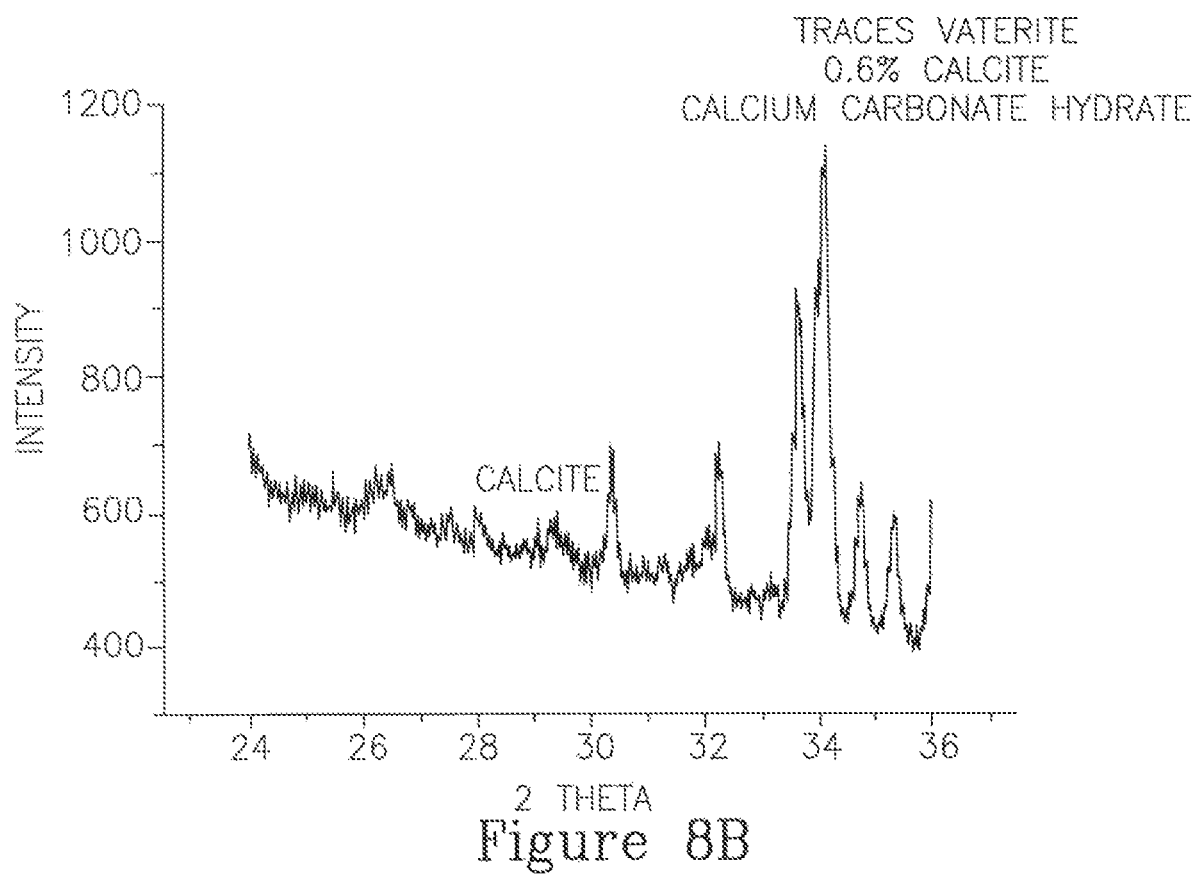
FIG. 8B: XRD pattern of encapsulated ACC composition (Formulation 22) mixed with yogurt; XRD performed on the last day of the experiment.
Figure 9A:
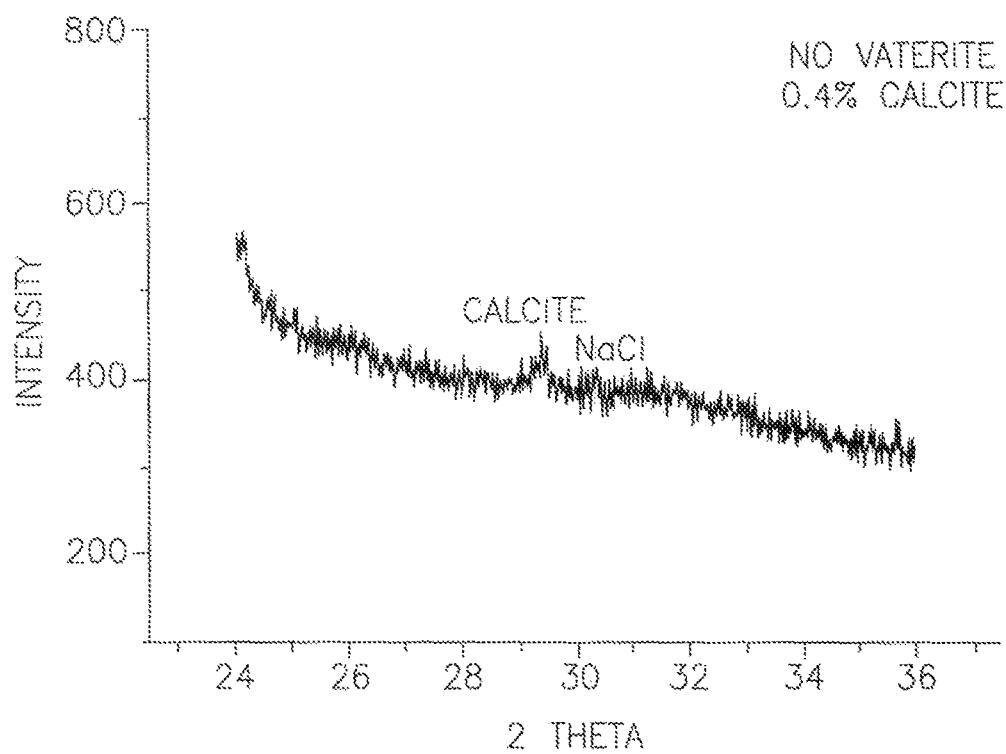
FIG. 9A: XRD pattern of encapsulated ACC composition (Formulation 23) mixed with yogurt; XRD performed on the first day of the experiment.
Figure 9B:
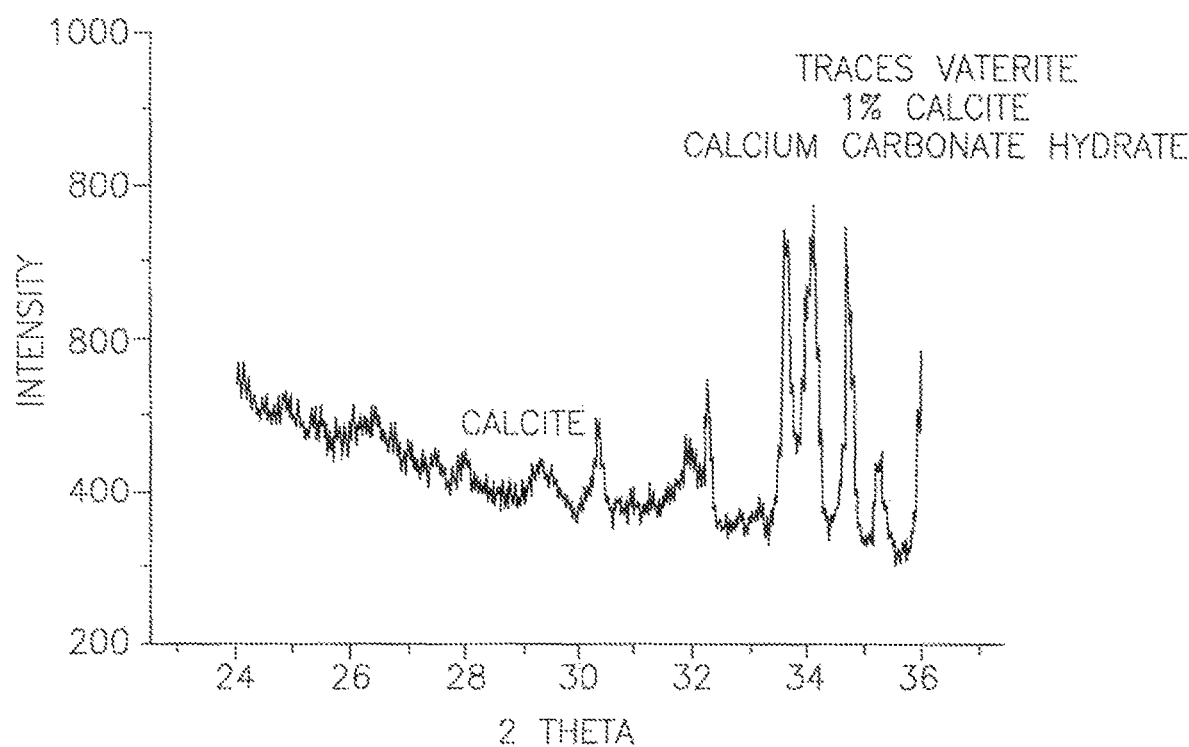
FIG. 9B: XRD pattern of encapsulated ACC composition (Formulation 23) mixed with yogurt; XRD performed on the last day of the experiment.
Figure 10:
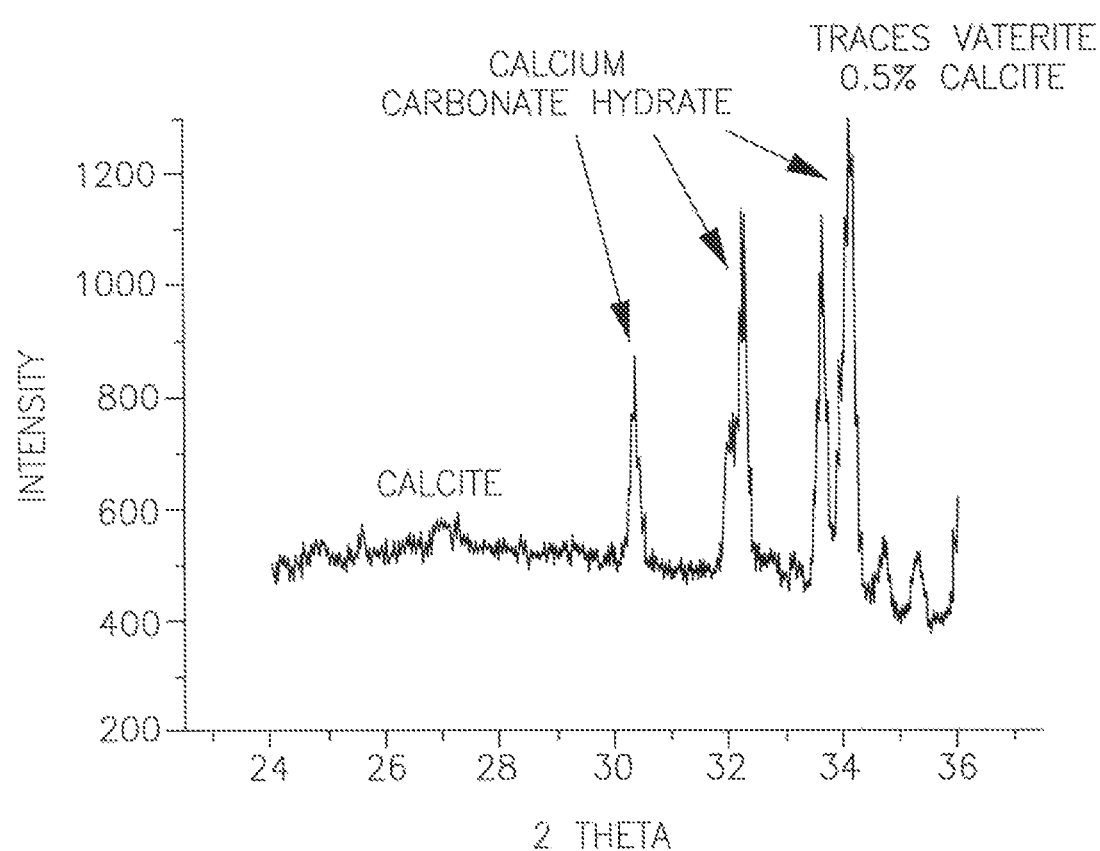
FIG. 10: XRD pattern of the non-encapsulated ACC mixed with yogurt; XRD performed on the first day of the experiment.

The XRD experiments were performed on samples freeze dried for 3-5 days. As a control, encapsulated ACC containing 5% Ca was mixed with yogurt, centrifuged and a sample of the solid phase was freeze dried immediately. The dry encapsulated ACC and yogurt content were then sent to the XRD analysis. The XRD spectra of the encapsulated ACC before and after the stability test are presented in FIGS. 7A and 7B (Formulation 21), FIGS. 8A and 8B (Formulation 22), FIGS. 9A and 9B (Formulation 23) and FIG. 10 represents XRD spectrum of a non-encapsulated ACC mixed with yogurt.

Analysis of the Experimental Results

Calcium content in the solid phase of the yogurt without any additional calcium supplement is about 0.16 wt %. In the control batch, 9 wt % of non-encapsulated CCC was added to yogurt and after 1 day of storing approximately 5 wt % thereof were detected in the solid phase. This level was essentially maintained throughout the 13 days of testing.

In the encapsulated stable ACC, after 1 day only approximately 2 wt % calcium was present in the solid phase of the yogurt. Since the dissolution of the Ca is below the saturation level (4% Ca according to the above control experiment with CCC), it is clear that the encapsulation protected the ACC particles. Thus, in the first day there was dissolution of about 60% of the encapsulated ACC into the aqueous phase of the yogurt. Only particles within the encapsulated matrix that were in direct contact with water due to insufficient encapsulation were immediately dissolved during the first day of the experiment. In contrast, ACC particles that are completely encapsulated did not dissolve and mostly remained in their original amorphous phase due to the barrier formed by the encapsulation matrix. The undissolved ACC maintained between 80 to 90% of its amorphous phase throughout the 13 days of testing.

TABLE 9

| Calcium titration results. | | | | | | | | |
|---|---|---|---|---|---|---|---|---|
| | Day | | | | | | | |
| Form. # | 1 | 2 | 3 | 4 | 6 | 7 | 9 | 13 |
| 21 | 1.72 | 1.57 | 1.58 | 1.62 | 1.6 | 1.54 | 1.64 | 1.66 |
| 22 | 1.94 | 1.86 | 1.88 | 1.91 | 1.8 | 1.69 | 1.62 | 1.83 |
| 23 | 2.13 | 1.96 | 2.06 | 2.12 | 2 | 1.95 | 1.7 | 1.96 |
| Non-encapsulated CCC | 9.08 | 4.95 | 5.8 | 6.12 | 6.2 | 9.03 | 6.04 | 6.59 |
| Non-encapsulated ACC | 3.12 | 2.95 | 3.16 | 3.25 | 3.1 | 2.88 | 2.03 | 3.3 |
| Yogurt (control) | 0.16 | 0.12 | 0.12 | 0.16 | 0.14 | 0.16 | 0.14 | 0.14 |

Example 6

Encapsulation with Ethyl Cellulose Using Pan Coating Process (Formulation 26)

Solution A was prepared with ethyl cellulose (15%) and ethanol (85%). Ethyl cellulose was added slowly to ethanol using high shear homogenizer until ethyl cellulose was completely dissolved and the solution became clear. An amount of 400 g ACC was added to pan coating machine. Then 600 g of Solution A were applied by spraying (via spray nozzle) into the coating machine while the speed of the pan was at maximum until obtaining wet granular consistency. The wet granules were dried by a fluidized bed process. The dry granules were dry milled (for particle size reduction) by a granulation milling machine. The milled powder of ACC-ethyl cellulose powder was placed in a pan coating machine. An amount of 375 g of a Solution B (prepared by mixing 60 g of ethyl cellulose and 700 g of ethanol) was sprayed as coatings over the ACC containing powder.

The obtained granules were dried and milled again. The milling process is critical to achieve small particle size, so if micronized particle size is needed, different dry milling equipment like ball mill/jet mill will be required. Any relevant coating apparatus can be used (like spray-dryer system). Any relevant powder grinding machine can be used.

Example 7

Encapsulation with Ethyl Cellulose-Wax Emulsifiers Using Pan Coating Process (Formulations 27 and 28)

Formulation 27: A solution was prepared containing candelilla wax (80 g), Span60=sorbitan monostearate (40 g), glyceryl stearate (40 g) and ethanol (400 g). The mixture was heated to 80-85 C. An amount of 150 g of the ACC-ethyl cellulose powder of Formulation 26 was placed in a pan coating machine. Then the candelilla wax solution was added very slowly into the middle of the coating pan while the pan speed was at maximum level until obtaining wet granular/dough phase. The wet Formulation was then dried by fluidized bed process and milled using a granulation machine. The milling process is critical to achieve smallest particle size, so if micronized particle size is needed, different dry milling equipment like ball mill/jet mill should be used. Any relevant coating equipment can be used (like spray-dryer system). Any relevant powder grinding machine can be used.

Formulation 28: A Solution of ethyl cellulose (90 g) and ethanol (1 kg) was prepared by adding ethyl cellulose slowly to the ethanol using high shear until all ethyl cellulose dissolved and a clear solution was obtained. Formulation 27 was placed in a pan coating machine. The above solution was sprayed (400 g) over the powder while the pan speed was on maximum. The wet medium was dried by fluidized bed and milled to farm uniform particles by a granulating milling machine. The spraying-drying-milling process was repeated.

Example 8

ACC Coating with Ethyl Cellulose Using Pan Coating (Formulations 29 and 30)

Formulation 29: Solution A was prepared containing ethyl cellulose (175 g) and ethanol (2.1 kg). Ethyl cellulose was added slowly to ethanol using high shear homogenizer until ethyl cellulose was completely dissolved and a clear solution was obtained. An amount of 900 g ACC was placed in a pan coating equipment. Solution A (approximately 420 g) was then sprayed over the ACC while the pan speed was at maximum power. The wet granules-dough formulation was dried by fluidized bed drying technology. The dry media was milled to form uniform particle size by granulation milling machine. The above spraying-drying-milling process was repeated four times until all solution A was consumed.

Formulation 30: A solution was prepared containing Nutraficients food supplement coating 112A280000 White (Colorcon®) (36 g) and ethanol (200 g). (The Colorcon® contains hydroxypropyl methyl cellulose, hydroxypropyl cellulose, talc, and titanium dioxide). The Colorcon® was added slowly to the ethanol using high shear until it was completely dispersed. The dispersion must be white. An amount of 190 g of Formulation 29 was place in the pan coating machine. Then 200 g of the above solution was sprayed on the powder while pan speed was set on maximum. The sprayed formulation was then dried and milled.

Example 9

ACC Coating with Wax and Emulsifiers by Lodige Mixer Type (Formulation 31)

Solution A was prepared containing glyceryl stearate (10 g), beeswax (20 g), candelilla wax (45 g), ethanol (300 g), sorbitan monostearate (10 g), and polyoxyethylene sorbitan monooleate (10 g). All the ingredients were mixed and heated to 80-85° C. An amount of 200 g ACC was placed in a mixer granulator horizontal (Lodige). The above solution (270 g) was added very slowly while the speed of the mixer was set to maximum. The wet formulation was dried by fluidized bed and milling using granulation milling machine.

Solution B was prepared with ethanol (300 g), paraffin wax (40 g), glyceryl stearate (45 g), Sisterna SP01 (E473) (5 g), and polyoxyethylene sorbitan monooleate (5 g). All the ingredients were mixed and heated to 80-85 C. The above granulated powder was placed in a mixer granulator horizontal (Lodige). Solution B was added very slowly while the speed of mixer is set to maximum. The wet mixture was dried by fluidized bed technique. The dried medium was milled by a granulation milling machine.

Example 10

ACC Coating with Ethyl Cellulose, Wax and Emulsifiers Using Pan Coat (Formulations 32, 33 and 34)

Formulation 32: A solution was prepared mixing PEG400 (200 g) and PVA (10 g) and heating to 85-90 C. An amount of 200 g ACC were placed in a mixer granulator horizontal (Lodige). 130 g of the solution was added very slowly while speed of mixer was set to maximum. A second solution was prepared with beeswax (25 g), ethanol (300 g), polyoxyethylene sorbitan monooleate (20 g), and sorbitan monostearate (7 g) and heating the mixture at 80-85° C. An amount of 160 g of the second solution was added very slowly while speed of mixer was set on maximum. The wet formulation was dried partially by fluidized bed technology. A third solution was made of beeswax (35 g), ethanol (500 g), polyoxyethylene sorbitan monooleate (25 g), sorbitan monostearate (10 g), methyl cellulose (20 g), and stearic acid (30 g). Then, 200 g of the third solution was added very slowly to the above dried formulation, while the speed of mixer was set to maximum. The final product looked slightly wet and dough-like.

Formulation 33: Solution A was prepared consisting of ethyl cellulose (60 g) and ethanol (600 g). 400 g of ACC were placed in a pan coating machine. 600 g of Solution A was sprayed over the ACC powder while pan speed was set on maximum. The wet granules-dough consistency mixture was dried by fluidized bed drying technology and milled to form uniform particles by a granulating milling machine. Solution B was prepared by mixing candelilla wax (120 g), ethanol (800 g), ARLACEL60=sorbitan monostearate (60 g), and Span 65=sorbitan tristearate (100 g) and heating at 80-85° C. while stirring. The product was placed in a pan coating machine and 400 g of the solution B were poured very slowly into the middle of the coating pan while the pan speed was set at maximum level until a wet granular/dough consistency was achieved. The mixture was dried by fluidized bed technology and milled to form uniform particles by granulating milling machine. Any relevant coating machine can be used to manufacture the formulations (for example, spray-dryer system).

Formulation 34: An amount of 300 g from the product of Formulation 32 was placed in a pan coating machine. 300 g solution B from Formulation 32 were added very slowly into the middle of the coating pan, while the pan speed was set at maximum level, until a wet granular/dough phase was achieved. The wet phase was dried by fluidized bed technology and milled to form uniform particles by granulating milling machine.

Example 11

ACC Coating with Ethyl Cellulose, Wax, Emulsifiers and Hydrophobic Flavor Using Pan Coating Machine (Formulation 35)

A batch of 50 g from Formulation 33 was placed in a pan coating machine. An amount of 50 g solution as described below was added very slowly into the middle of the coating pan, while the pan speed at maximum level until a wet granular/dough phase is achieved. The solution consisted of Tutti-Frutti flavor (Sypris) (0.7%), beeswax (12%), ethanol (71.3%), sorbitan monostearate (6%), and sorbitan tristearate (10%). The wet consistency was dried by fluidized bed technique and milled to generate uniform particles by granulating milling machine. The dry powder was sieved through 50 mesh sieve. The estimated content of the ACC in this product was in the range of 55 to 60 wt % based on the total added ingredients.

Example 12

ACC Coating with Colorcon® Coating System Using Pan Coating (Formulation 37)

Solution A was prepared consisting of Nutraficients food supplement coating 112A280000 White (Colorcon®) (180 g) and ethanol (1.6 kg). (Colorcon® contains hydroxypropyl methyl cellulose, hydroxypropyl cellulose, talk and titanium dioxide.) A white dispersion was obtained. An amount of 200 g ACC was placed in a pan coating machine. 400 g of Solution A were sprayed over the ACC while pan speed is set to maximum. The wet phase was dried by a fluidized bed technique. The dry formulation was milled to form uniform particle size by granulation milling machine and placed in a coating pan. The spray-dry-milling process was repeated once.

Example 13

Stability Test Procedure for Various Batches in Yogurt

Figure 11:
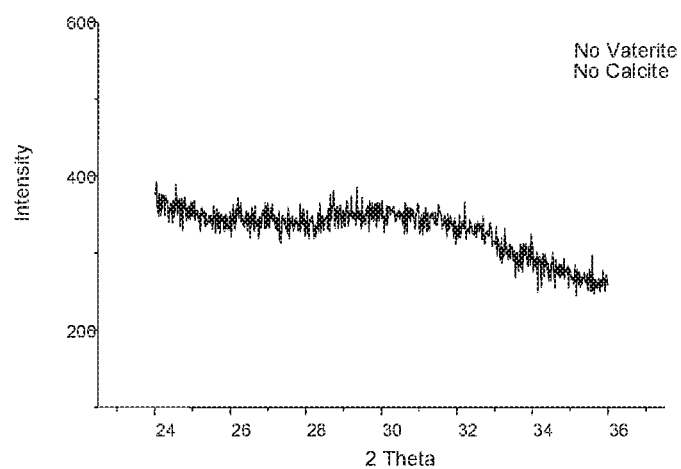
FIG. 11: XRD pattern of encapsulated ACC composition (Formulation 32).
Figure 12A:
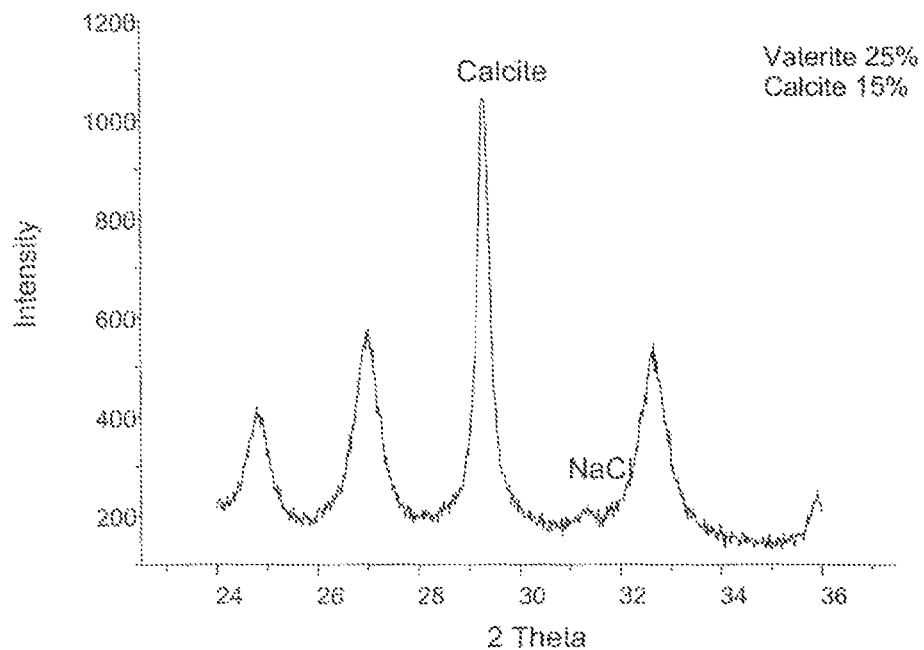
FIG. 12A: XRD pattern of encapsulated ACC composition (Formulation 27) mixed with yogurt; XRD performed after the first week of the experiment.
Figure 12B:
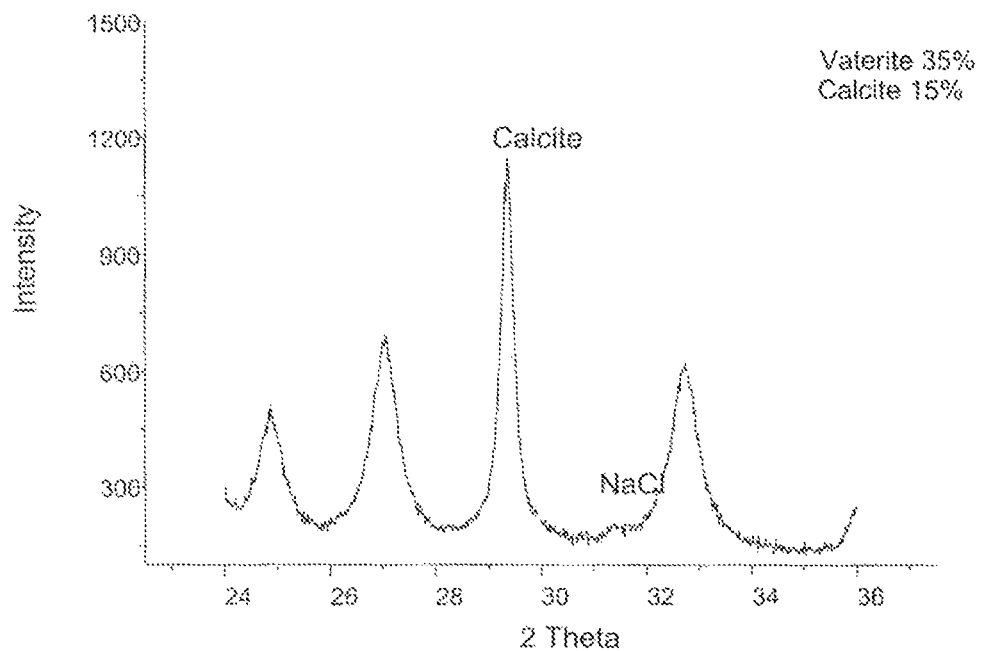
FIG. 12B: XRD pattern of encapsulated ACC composition (Formulation 27) mixed with yogurt; XRD performed after the second week of the experiment.

Formulations 27 and 32 were analyzed for their Ca content by atomic absorption (AA) analysis, and stability of the incorporated ACC was analyzed by Raman and XRD spectroscopies (FIGS. 11 and 12). Selected batches were then tested for 3 week stability in authentic yogurt supernatant solutions. The experiments were performed using the solution of 3% fat yogurt (pH of about 4.2-4.5) of Strauss Group Ltd. separated from the solid suspension by centrifuge.

Every week suspended ACC was collected and analyzed to determine whether or to what extent ACC was still stable or has crystallized. Three or four samples of each encapsulated batch of ACC were made with yogurt solution by mixing 2.5 g gram of the encapsulated formulation in 30 ml of yogurt solution. The samples were stored at 4° C. In a refrigerator during the time of the experiment. At the end of each week, the solutions were filtrated and washed 3 times with ethanol (150 ml) followed by an additional wash with acetone (150 ml) to remove water and coating residues. The remaining filtrate was collected and tested by a polarized microscope, a Raman spectrometer and XRD (FIGS. 12A-12B) to determine the percentage of the ACC in the sample.
Blank Tests Blank (I)—uncoated stable ACC. Uncoated stable ACC was suspended in ethanol/acetone (50/50 by volume) solution and heated to about 65-70° C. for 10 minutes. The suspended ACC was filtrated, dried and Raman spectroscopy tests were performed 3 times in order to collect the data from different sides of the sample. The Raman results show 95.45%, 96.55% and 93.61% retention of the ACC amorphous phase. These results confirm that this procedure doesn't cause significant crystallization of the ACC.

Blank (II)—encapsulated stable ACC. In this procedure, each of the encapsulated ACC Formulations in Table 10 was suspended in ethanol/acetone (50/50 by volume) solution and heated to about 65-70° C. for 10 min. The rest of the analysis was similar to the previous blank sample with the goal to ensure that the coating was removed from the ACC and the spectral analyses were performed only on the ACC without the encapsulation. The Raman analysis in 3 different spots showed 94.35%, 97.42% and 96.11% retention of the ACC amorphous phase.

Comparative test of non-encapsulated stable ACC stability in Yogurt. An amount of 2.5 g of uncoated stable ACC was mixed with 50 ml of yogurt solution that was separated from its solids using centrifuge. Samples from the suspension were taken and dried using compressed air (a procedure that is typically used to test the stability of synthesized ACC). The dry powder was examined by polarized microscope. A sample taken after 3 min was still stable. After 13 min the ACC started crystallizing (about 20% crystallization). After 19 min most of the ACC was crystallized (more than 80% crystallized). As shown in Table 10, which summarizes the stability of all tested encapsulation formulations, the stability value of the non-encapsulated ACC is more the 3 orders of magnitude lower than some of the improved encapsulated formulations.

Summary of stability tests with various batches of encapsulated ACC suspended in yogurt solutions for up to 3 weeks. Table 10 summarizes the results of various batches described in the above examples. Batches that show stability above 15% after 1 week are considered suitable for commercial purposes. Batches that show stability above 30% after 3 weeks are considered particularly suitable for selected commercial purposes.

TABLE 10

Crystal structure assessment of encapsulated ACC following yogurt stability tests.

| Formulation | Sample/Week | XRC % ACC | % Calcite | % Vaterite | Raman % ACC |
|---|---|---|---|---|---|
| 27 | I/I | 60 | 15 | 25 | 58.65 |
|  | I/II | 50 | 15 | 35 | 65 |
|  | I/III | 35 | 20 | 45 | 19-51 |
| 28 | I/I | No further analyses were taken after the first week | | | 22.3 |
|  | I/II | | | | |
|  | I/III | | | | |
| 30 | I/I | No further analyses were taken after the first week | | | 21.14 |
|  | I/II | | | | |
|  | I/III | | | | |
| 26 | I/I | No further analyses were taken after the first week | | | 63.97 |
|  | I/II | | | | |
|  | I/III | | | | |
| 34 | I/I | 71 | 4 | 25 | 78.15 |
|  | I/II | 68 | 4 | 28 | 63.9 |
|  | I/III | | | | |
| 33 | I/I | 69 | 6 | 25 | 72.35 |
|  | I/II | 63 | 7 | 30 | 57.28 |
|  | I/III | | | | |
| 35 | I/I | 93.5 | 0.5 | 6 | 89.28 |
|  | I/II | 74 | 1 | 25 | 93.91 |
|  | I/III | 52.5 | | | |

Example 14

Pan-Coating+Heating (Formulations 38-41)

380 g ACC were inserted into a coating pan. 330 g ethyl cellulose 10% solution (30 g ethyl cellulose+300 g alcohol) was slowly added to the pan and mixed. The content of the pan was then dried using 100° C. blower for 2 hours and the powder was grinded using 70 mesh sieve. A mixture of coating formulation: 600 g alcohol, 30 g bees wax, 70 g candelilla wax, 6 g sorbitan monostearate and 20 g sorbitan tristearate was prepared and heated until boiling (coat #2). Coat #2 was added to the pan and mixed, then dried and the powder was grinded. A mixture of coating formulation: 340 g alcohol, 50 g bees wax and 30 g candelilla wax was prepared and heated until boiling (coat #3). Coat #3 was added to the pan and mixed, then dried grinded and dried again.

TABLE 11

Heat resistant ACC.

| Formulation # | No. of coatings | % calcium | % ACC powder w/w (core) | % ACC (XRD after 2 min in 95° C. water) | % ACC (XRD after 1.5 min MW heating in water) | % crystalized in yogurt (3 weeks) |
|---|---|---|---|---|---|---|
| 38 | 3 | 18 | 60 | 35 | 47.2 | 19.5 |
| 39 | 4 | 14 | 46.6 | 53.5 | 55.6 | 35.5 |
| 40 | 2 | 20 | 66.6 | 44.3 | 54.2 | 23 |
| 41 | 4 | 9 | 30 | 84.6 | — | 28.5 |

The data provided in Table 11 demonstrates that that there is no further improvement on amorphous state at elevated coating layers in yogurt, so it is hypothesized that the success of Formulations 38-41 comes from the use of hydrophobic silica in the core formulation, and from the use of a sub-coating layer of ethyl cellulose.

Composition and Preparation

Formulation 38: 1 sub-coat+2 coatings. 600 g ACC (+6.25% AEROSIL200, a hydrophilic silica) were added to 140 mesh, sieved and grinded. The powder was added to a coating pan. 660 r ethyl cellulose 10% solution (60 g ethyl cellulose+600 g alcohol) were slowly added to the pan and mixed at 300 rpm for 30 min (coat #1). The contents were dried using 100° C. blower for 2 hours. The powder was grinded using 70 mesh sieve. The powder was added to coating pan. In a glass beaker, 300 g alcohol, 40 g carnauba wax and 40 g candelilla wax were mixed (wax mix #1). Ingredients were heated until boiling (coat #2). Wax mix #1 was added to the pan and mixed at 350 rpm for 2 min. The contents were dried using 100° C. blower for 2 hours. The powder was grinded using 70 mesh sieve. In a glass beaker, 350 g alcohol, 40 g carnauba wax and 40 g candelilla wax were mixed (wax mix #2). The ingredients were heated until boiling (coat #3). Wax mix #2 was added to the pan and mixed at 300 rpm for 2 min. The contents were dried using 100° C. Blower for 2 hours. The powder was grind using 100 mesh sieve. The contents were dried using 100° C. Blower for 2 hours.

Formulation 39: 1 sub-coat+3 coatings. 240 g ACC (+10% AEROSIL200) were added to 140 mesh, sieved and grinded. The powder was added to a coating pan. 340 gr ethyl cellulose (10% solution) were slowly added to the pan and mixed at 300 rpm for 30 min (coat #1). The contents were dried using 100° C. blower for 2 hours. In a glass beaker, 250 g alcohol, 40 g rice bran wax and 40 g carnauba wax (wax mix #1). Heat the ingredients until boiling (coat #2). Wax mix #1 was added to the pan and mixed at 300 rpm for 2 min. The contents were dried using 100° C. blower for 2 hours. In a glass beaker, 350 g alcohol, 40 g rice bran wax and 40 g carnauba wax were mixed (wax mix #2). The ingredients are heated until boiling (coat #3). Wax mix #2 was added slowly to the pan and mixed at 300 rpm for 2 min. The contents were dried using 100° C. blower for 2 hours. The powder was grind using 70 mesh sieve. The powder was added to coating pan. In a glass beaker, 150 g alcohol, 10 g rice bran wax and 10 g carnauba wax were mixed (wax mix #3). The ingredients are heated until boiling (coat #4). Wax mix #3 was slowly added to the pan and mixed at 300 rpm for 2 min. The contents were dried using 100° C. blower for 2 hours. The powder was grind using 140 mesh sieve.

Formulation 40: 2 coatings. 250 g ACC (+6.25% AEROSIL200) were added to 140 mesh, sieved and grinded. The powder was added to a coating pan. In a glass beaker, 650 g alcohol, 35 g carnauba wax and 20 g candelilla wax were mixed (wax mix #1). Ingredients were heated until boiling (coat #1). Wax mix #1 was added to the pan and mixed at 350 rpm for 2 min. The contents were dried using 100° C. blower for 3 hours. The powder was grinded using 70 mesh sieve. The powder was added to coating pan. In a glass beaker, 250 g alcohol, 15 g carnauba wax and 10 g candelilla wax were mixed (wax mix #2). The ingredients were heated until boiling (coat #2). Wax mix #2 was slowly added to the pan and mixed at 300 rpm for 2 min. The contents were dried using 100° C. blower for 3 hours. The powder was grind using 100 mesh sieve.

Formulation 41: 1 sub-coat+3 coatings. 350 g ACC (+10% SIPERNAT 50S=hydrophobic silica) were added to 70 mesh sieve and grinded. The powder was added to a coating pan. 770 g ethyl cellulose (10% solution) was added to a pan and mixed at 300 rpm for 30 min (coat #1). The contents were dried using 100° C. blower for 2 hours. In a glass beaker, 300 g alcohol, 15 g span60, 30 g span65 and 35 g candelilla wax were mixed (mix #1). The ingredients were heated until boiling (coat #2). First coating layer: wax mix #1 was added to the pan and mixed at 300 rpm for 2 min. The contents were dried using 85° C. blower for 2 hours. The powder was grinded using 70 mesh sieve. Preparation of second coating formulation: in a glass beaker, 300 g alcohol, 15 g span60, 30 g span65 and 35 g candelilla wax were mixed (mix #2). The ingredients were heated until boiling (coat #3). Second coating layer: wax mix #2 was added to the pan and mix at 300 rpm for 2 min. The contents were dried using 85° C. blower for 2 hours. The powder was winded using 70 mesh sieve. The powder was added to coating pan. Preparation of third coating formulation: In a glass beaker, 250 g alcohol, 25 g beeswax and 25 g candelilla wax were mixed (mix #3). The ingredients were heated until boiling (coat #4). Third coating layer: wax mix #1 was added to the pan and mixed at 300 rpm for 2 min. The contents were dried using 85° C. blower for 2 hours. The powder was grinded using 70 mesh sieve.

This example presents sub-coating+three coating layers and results in a thick, potentially hermetic coating. This example resulted in better heat resistance of the ACC core formulation, i.e. less crystallization of the ACC upon heat treatment. The advantage of multi-layer coating is better protection of ACC from crystallization.

Procedure 1

A laboratory glass was filled with 10 mL of tap water. The water was heated to 95° C. on a hot plate and stirred continuously using a stirrer. At 95° C., 2.5 g encapsulated ACC powder was added and heating and stirring continued for 5 min. The glass was then removed from heat and allowed to cool to about room temperature. Table 12 presents XRD results after filtering and washing.

Procedure 2

A laboratory glass was filled with 10 mL of tap water. 2.5 gr encapsulated ACC powder was added and mixed for 2 min. The glass was heated in a conventional domestic microwave oven at 1,200 Watts for 1.5 min. The water reached 95-100° C. The glass was then removed from MW and allowed to cool to about room temperature. Table 12 presents XRD results after filtering and washing.

TABLE 12

XRD results.

| Formulation # | % ACC ($T_0$) | % ACC (XRD 2 min 95° C.) | Normalized % ACC | % ACC (XRD after 1.5 min Microwave heating) | Normalized % ACC | % crystallization in yogurt (3 weeks) | Normalized % ACC |
|---|---|---|---|---|---|---|---|
| 38 (Sub-coating + 2 layers) | 96.5 | 35 | 36.3% | 47.2 | 48.9% | 19.5 | 20.2% |
| 39 (Sub-coating + 3 layers) | 96.6 | 53.5 | 55.4% | 55.6 | 57.6% | 35.5 | 36.7% |
| 40 (No sub-coating + 2 layers) | 98 | 44.3 | 45.2% | 54.2 | 55.3% | 23 | 23.5% |
| 41 (Sub-coating + 3 layers) | 93.6 | 84.6 | 90.4% | — | — | 28.5 | 30.4% |

Example 15

Heat Resistance of Uncoated Core Composition (Formulation 42)

ACC particles coated by 4 coatings (a sub-coating layer of ethyl cellulose and three wax composition layers, 65% ACC coated by 10.3% ethyl cellulose, 12% candelila wax, 5% sorbitan tristearate, 3% sorbitan monostearate, 2.7% fumed silica, and 2% beeswax) (5%) and sodium hydroxide (1%) were added into 94% yogurt. Yogurt was heated until boiling (95° C.) and continued heating for 10 minutes using mixing with magnetic stirrer. Yogurt hot solution was filtered using 400 mesh sieve. XRD result −35% crystalline, 65% amorphous.

Example 16

Sub-Coating+3 Layers Coating of a Silica-Free Core Formulation (Formulation 44)

The coating process may be done using a coating pan, a horizontal mixer, or other suitable mixing devices. 380 g ACC (without AEROSIL200) were added to a 2 mm sieve and grinded. The powder is added to coating pan. Sub-coating layer: 330 gr ethyl cellulose 10% solution (30 g ethyl cellulose+300 g alcohol) were added to the pan and mix at 300 rpm for 30 min (coat #1). The contents were dried using 100° C. blower for 2 hours. The powder (powder=ACC core formulation+sub-coating layer of ethyl cellulose) was grinded using 70 mesh sieve. The powder was added to coating pan. The second coating layer (preparation of coating hydrophobic solution): in a glass beaker, 600 g alcohol, 30 g beeswax, 70 g candelilla wax, 6 gr sorbitan monostearate, 20 g sorbitan tristearate were mixed. The ingredients were heated until boiling (coat #2). Coat #2 (the hydrophobic solution) was added to the pan and mixed at 350 rpm for 2 min. The contents were dried using 100° C. blower for 2 hours. The powder (core formulation with two coating layers) was grinded using 70 mesh sieve. Preparation of another coating hydrophobic solution for another coating layer: in a glass beaker, 340 g alcohol, 50 g bees wax and 30 g candelilla wax were mixed. The ingredients were heated until boiling (coat #3), then added to the pan and mixed at 300 rpm for 2 min. The contents were dried using 100° C. blower for 2 hours. The powder (ACC core formulation+ sub-coating layer+2 hydrophobic coating layers) was grinded using 70 mesh sieve. The contents were dried using 100° C. blower for 2 hours.

The resulting product was checked for heat stability. A portion of the product was added to boiling water and left for two minutes, result: 95% of the calcium carbonate of the core formulation was crystalized. A portion of the product was put in a microwave at the maximum temperature for two minutes, result: 84% of the calcium carbonate of the core formulation was crystalized.

A possible conclusion is that the addition of silica to the core formulation improves the heat resistance of the ACC powder formulation that is further sub-coated and coated by two coating layers.

Example 17

Sub-Coating+4 Layers Coating (Formulation 45)

105 g ACC and 4% silica were milled by 70 mesh and inserted into a mixer. The particles were sub-coated (cold process) by 99 g of 10% ethyl cellulose solution, then mixed, dried and milled by 70 mesh. $1^{st}$ coating layer: 104 g sub-coated ACC cores were inserted into a mixer, heated, and mixed with candelilla wax 2.3 g, isopropanol 47 g, span 60 1.13 g, span 65 1.84 g, dried and milled by 70 mesh. $2^{nd}$ coating layer: Particles from the previous step were inserted into a mixer, heated, and mixed with candelilla wax 2 g, alcohol 35 g, bees wax 0.7 g, span 60 0.35 g, span 65 0.35 g, dried and milled by 70 mesh. $3^{rd}$ coating layer: Particles from the previous step were inserted into a mixer, heated, and mixed with bees wax 1.55 g, 27 g alcohol, span 60 0.062, span 65 0.155 g, candelilla wax 0.97 g, dried and milled by 60 mesh. $4^{th}$ coating layer: Particles from the previous step were inserted into a mixer, heated, and mixed with bees wax 0.25 g, alcohol 35 g, span 60 0.1 g, span 65 0.25 g, candelilla wax 1.56 g, dried and milled by 40 mesh.

Figure 13:
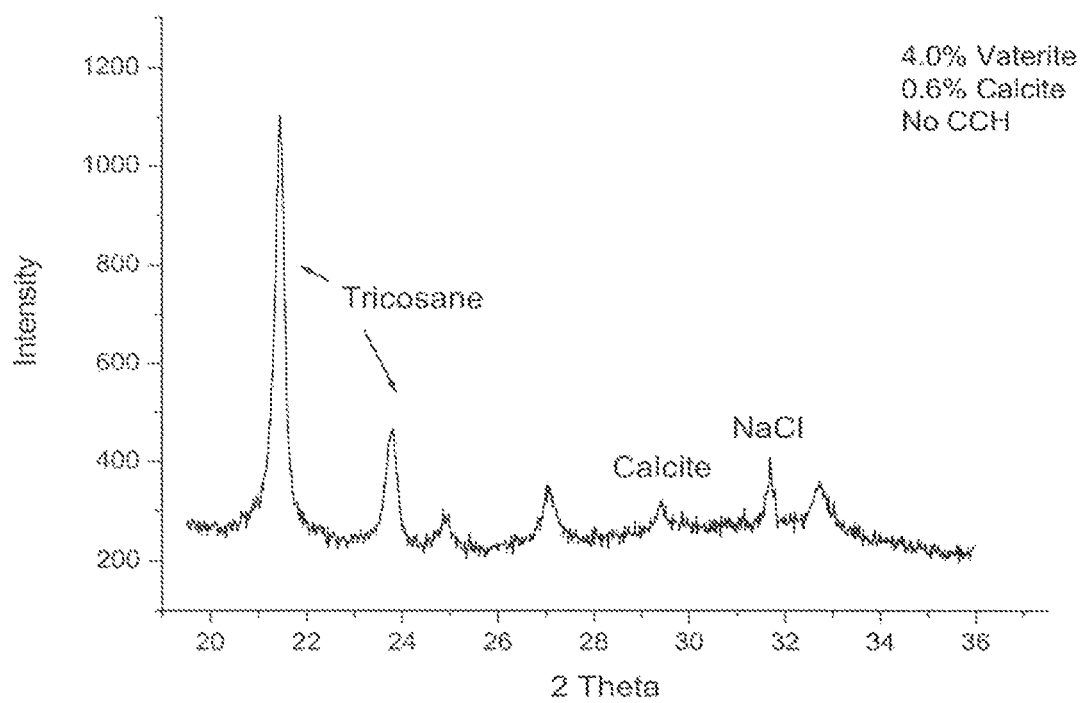
FIG. 13: XRD pattern of encapsulated ACC composition (Formulation 45).

The concentration of calcium in a sample of the final encapsulated ACC product was measured by ICP (inductively Coupled Plasma). The rest is considered to be the encapsulation materials (sub-coating+4 coating layers). XRD of the final encapsulated ACC product was upon completion of coating processes (FIG. 13). Furthermore, Formulation 45 provides satisfactory organoleptic results when inserted to yogurt.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

The invention claimed is:

1. An encapsulated amorphous calcium carbonate (ACC) composition, comprising:
   a plurality of solid encapsulated ACC particles each including:
   i. an ACC core including ACC and at least one agent stabilizing the ACC in amorphous form; and
   ii. an encapsulation matrix completely coating the ACC core and including two coating layers, wherein each one of the two coating layers at least partly coats the ACC core, wherein the two coating layers includes a first inner coating layer that contacts the ACC core and including a film forming polymer and another coating layer including a lipid, and
   iii. optionally the encapsulation matrix further comprises one or more additional coating layers, each of said one or more additional coating layers including an encapsulating agent selected from the group consisting of a film forming polymer and a lipid,
   wherein the encapsulation matrix is a combination of all coating layers, wherein each one of the film forming polymers includes a polymer selected from the group consisting of cellulose, a cellulose derivative, methyl methacrylate, and any combination thereof and the lipid includes a member selected from the group consisting of an edible wax, a fatty acid, a fatty acid ester, an oil, and any combination thereof, and wherein the encapsulation matrix retains at least 20% of the calcium carbonate in amorphous form and undissolved, after the composition is exposed to an aqueous medium for at least one week.

2. The composition of claim 1, wherein the encapsulation matrix substantially retains ACC in amorphous form upon exposure to external temperature of at least 50° C. or to acidic media.

3. The composition of claim 1, wherein the cellulose derivative includes a member selected from the group consisting of ethyl cellulose, methyl cellulose, hydroxypropyl cellulose, hydroxypropyl methyl cellulose, methyl ethyl cellulose, ethyl hydroxyethyl cellulose, carboxymethyl cellulose, and any combination thereof.

4. The composition of claim 1, wherein at least one of:
   the edible wax includes a wax selected from the group consisting of beeswax, candelilla wax, carnauba wax, Japan wax, soy wax, alfa wax, rice-bran wax, bayberry wax, castor wax, montan wax, microcrystalline wax, paraffin wax, and any combination thereof; or
   the fatty acid includes an acid selected from the group consisting of stearic acid, oleic acid, palmitic acid, lauric acid, and any combination thereof; or
   the fatty acid ester includes an ester selected from a glyceride stearate or a sucrose polystearate; or
   the oil includes an oil selected from the group consisting of a vegetable oil, liquid paraffin, a medium-chain triglyceride oil, and any combination thereof.

5. The composition of claim 1, wherein the encapsulation matrix includes at least one agent selected from the group consisting of a natural resin, a biocompatible polymer, a prolamine protein, an agent stabilizing the ACC, a surfactant, a color, and a pigment.

6. The composition of claim 5, wherein at least one of:
   the natural resin includes Shellac;
   the biocompatible polymer includes a polymer selected from the group consisting of polyvinylpyrrolidone (PVP), polyethylene glycol (PEG), polyvinyl alcohol (PVA), and any combination thereof;
   the prolamine protein includes Zein; or
   the surfactant includes a member selected from the group consisting of a polysorbate, a sorbitan ester, a polyoxyethylene fatty acid ester, a sucrose ester of a fatty acid, glycerol monostearate, stearoyl lactylate, lecithin, and any combination thereof.

7. The composition of claim 1, wherein the agent stabilizing the ACC in amorphous form is independently at each occurrence selected from the group consisting of an organic acid, a sulfuric ester of a hydroxyl carboxylic acid, an organoamine compound, an organic compound comprising a hydroxyl, an organophosphorous compound or a salt thereof, a bisphosphonate compound, an organophosphate compound, an organophosphonate compound, an inorganic phosphorous acid, a polyphosphate compound, an organic surfactant, a bio-essential inorganic ion, and any combination thereof.

8. The composition of claim 1, wherein the ACC core and the encapsulation matrix exhibit a weight ratio therebetween of 1:5 to 5:1.

9. The composition of claim 1, wherein the encapsulation matrix includes at least three coating layers.

10. The composition of claim 9, wherein:
    the encapsulation matrix includes an additional coating layer including a film forming polymer, wherein the film forming polymer in each layer may be the same or different; or
    the encapsulation matrix includes an additional coating layer comprising a lipid.

11. The composition of claim 1, wherein the ACC core includes silica.

12. The composition of claim 1, wherein the composition is inert when mixed with a food article.

13. The composition of claim 12, wherein the composition when mixed with the food article, does not alter the taste, color and pH of the food article.

14. The composition of claim 1, wherein the encapsulation matrix retains:
    at least 70% of the calcium carbonate in amorphous form and undissolved, after the composition is exposed to an aqueous medium for at least four days;
    at least 20% of the calcium carbonate in amorphous form after the composition is exposed to an acidic medium for at least one week;
    at least 10% of the calcium carbonate in amorphous form after the composition is exposed to an acidic medium for at least three weeks; or at least 20% of the calcium carbonate in amorphous form after the composition is exposed to an aqueous medium at 95° C. for at least 2 minutes, or after the composition is exposed to 1,200 Watt microwave radiation for at least 1.5 minutes.

15. A food product including the encapsulated ACC composition of claim 1.

16. The food product of claim 15, wherein the food product includes a dairy product.

17. The food product of claim 16, wherein the dairy product includes at least one of fermented milk or being acidic.

18. The food product of claim 16 wherein the food product includes a yogurt, or requires heating at a temperature of at least 50° C. before consumption.

* * * * *